(12) United States Patent
De Matos Gomes

(10) Patent No.: US 11,885,858 B2
(45) Date of Patent: *Jan. 30, 2024

(54) SYSTEMS AND METHODS FOR VOLUMETRIC ACQUISITION IN A SINGLE-SIDED MRI SCANNER

(71) Applicant: PROMAXO, INC., Oakland, CA (US)

(72) Inventor: Muller Francis De Matos Gomes, Hayward, CA (US)

(73) Assignee: Promaxo, Inc., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/938,229

(22) Filed: Oct. 5, 2022

(65) Prior Publication Data
US 2023/0109705 A1    Apr. 13, 2023

Related U.S. Application Data

(63) Continuation of application No. 17/438,898, filed as application No. PCT/US2020/024778 on Mar. 25, 2020, now Pat. No. 11,506,737.
(Continued)

(51) Int. Cl.
*G01R 33/38* (2006.01)
*G01R 33/383* (2006.01)
(Continued)

(52) U.S. Cl.
CPC ..... *G01R 33/3808* (2013.01); *G01R 33/3415* (2013.01); *G01R 33/381* (2013.01);
(Continued)

(58) Field of Classification Search
CPC ............ G01R 33/3808; G01R 33/3415; G01R 33/381; G01R 33/383; G01R 33/385;
(Continued)

(56) References Cited

U.S. PATENT DOCUMENTS 8,461,836 B2    6/2013   Blank et al.
D895,803 S      9/2020   Nacev et al.
(Continued)

FOREIGN PATENT DOCUMENTS

CN    103885017 A    6/2014
CN    103983929 A    8/2014
(Continued)

OTHER PUBLICATIONS

English translation of WO96/10755A1 provided by Espacenet. 2023 (Year: 2023).*
(Continued)

*Primary Examiner* — Rishi R Patel
(74) *Attorney, Agent, or Firm* — Wilson Sonsini Goodrich & Rosati

(57) ABSTRACT

A method for performing magnetic resonance imaging is provided. The method includes providing a magnetic resonance imaging system comprising: a radio frequency receive system comprising a radio frequency receive coil, and a housing, wherein the housing comprises a permanent magnet for providing an inhomogeneous permanent gradient field, a radio frequency transmit system, and a single-sided gradient coil set. The method also includes placing the receive coil proximate a target subject; applying a sequence of chirped pulses via the transmit system; applying a multi-slice excitation along the inhomogeneous permanent gradient field; applying a plurality of gradient pulses via the gradient coil set orthogonal to the inhomogeneous permanent gradient field; acquiring a signal of the target subject via the receive system, wherein the signal comprises at least two chirped pulses; and forming a magnetic resonance image of the target subject.

17 Claims, 22 Drawing Sheets

Related U.S. Application Data

(60) Provisional application No. 62/823,511, filed on Mar. 25, 2019.

(51) Int. Cl.

| | | |
|---|---|---|
| *G01R 33/385* | (2006.01) | |
| *G01R 33/483* | (2006.01) | |
| *G01R 33/46* | (2006.01) | |
| *G01R 33/3415* | (2006.01) | |
| *G01R 33/381* | (2006.01) | |
| *A61B 5/00* | (2006.01) | |

(52) U.S. Cl.
CPC ......... *G01R 33/383* (2013.01); *G01R 33/385* (2013.01); *G01R 33/4616* (2013.01); *G01R 33/4835* (2013.01); *A61B 5/4381* (2013.01)

(58) Field of Classification Search
CPC ............ G01R 33/4835; G01R 33/4616; G01R 33/34076; G01R 33/341; G01R 33/3802; G01R 33/445; G01R 33/56563; A61B 5/4381; A61B 5/055; A61B 5/004
See application file for complete search history.

(56) References Cited

U.S. PATENT DOCUMENTS

| | | | |
|---|---|---|---|
| D942,012 S | 1/2022 | Nacev et al. | |
| 11,506,737 B2 * | 11/2022 | Gomes ................. | G01R 33/341 |
| D980,981 S | 3/2023 | Nacev et al. | |
| 11,609,291 B2 | 3/2023 | Nacev et al. | |
| 11,656,303 B2 | 5/2023 | Nacev et al. | |
| 2004/0155659 A1 | 8/2004 | Prado | |
| 2008/0180099 A1 | 7/2008 | Fautz et al. | |
| 2008/0182524 A1 | 7/2008 | Graesslin et al. | |
| 2008/0197845 A1 | 8/2008 | Trequattrini et al. | |
| 2008/0204020 A1 | 8/2008 | Chamberlain et al. | |
| 2012/0010497 A1 | 1/2012 | Ehman et al. | |
| 2014/0225610 A1 | 8/2014 | Popescu | |
| 2014/0361769 A1 * | 12/2014 | Hardie ................ | G01R 33/3692 324/322 |
| 2016/0139222 A1 * | 5/2016 | Frydman ............ | G01R 33/4833 324/309 |
| 2018/0335489 A1 | 11/2018 | Stainsby et al. | |
| 2018/0356480 A1 | 12/2018 | Weinberg et al. | |
| 2019/0383891 A1 | 12/2019 | Iwasawa et al. | |
| 2020/0003856 A1 | 1/2020 | Constable et al. | |
| 2020/0110144 A1 | 4/2020 | Frydman et al. | |
| 2022/0113361 A1 | 4/2022 | Nacev et al. | |
| 2022/0146613 A1 | 5/2022 | Gomes | |

FOREIGN PATENT DOCUMENTS

| | | | | |
|---|---|---|---|---|
| CN | 104965184 A | 10/2015 | | |
| CN | 105004748 A | 10/2015 | | |
| JP | 2014151207 A | 8/2014 | | |
| WO | WO-9610755 A1 * | 4/1996 | ......... | G01R 33/4835 |
| WO | 2018069050 A1 | 4/2018 | | |
| WO | 2018106760 A1 | 6/2018 | | |
| WO | WO-2020168233 A1 | 8/2020 | | |
| WO | WO-2020172672 A1 | 8/2020 | | |
| WO | WO-2020172673 A1 | 8/2020 | | |
| WO | 2020198396 A1 | 10/2020 | | |
| WO | WO-2020198395 A1 | 10/2020 | | |

OTHER PUBLICATIONS

International Search Report and Written Opinion for International PCT Application No. PCT/US2020/024778, dated Jul. 2, 2020.
He et al., The Novel Design of a Single-Sided MRI Probe for Assessing Burn Depth, Sensors (Mar. 6, 2017), 17(526):1-11.
Supplementary European Search Report for corresponding European Patent Application No. 20778407.5, dated Nov. 28, 2022.
King et al., Ultrafast Multidimensional Laplace NMR Using a Single-Sided Magnet, Angewandte Chemie, Wiley-VCH (Mar. 9, 2016), 128(9):5124-5127.
Blümich et al., Mobile single-sided NMR, Progress In Nuclear Magnetic Resonance Spectroscopy (May 1, 2008), 52(4):197-269.
Ciobanu et al. fMRI contrast at high and ultrahigh magnetic fields: Insight from complementary methods. NeuroImage 113 (2015) 37-43.
U.S. Appl. No. 17/438,898 Notice of Allowance dated Jul. 7, 2022.
U.S. Appl. No. 17/438,898 Office Action dated Mar. 16, 2022.
Wu et al. Simultaneous Multislice Multiband Parallel Radiofrequency Excitation with Independent Slice-Specific Transmit B1 Homogenization. Magnetic Resonance in Medicine 70: 630-638 (2013).
Ben-Eliezer et al. Fully refocused multi-shot spatiotemporally encoded MRI: robust imaging in the presence of metallic implants. Magn Reson Mater Phy 2012: 25: 433-442.
Ben-Eliezer et al. Spatiotemporal encoding as a robust basis for fast three-dimensional in vivo MRI. NMR Biomed 2011; 24: 1191-1201.
Feinberg et al. Ultra-Fast MRI of the Human Brain with Simultaneous Multi-Slice Imaging. J Magn Reson. Apr. 2013 ; 229: 90-100.

* cited by examiner

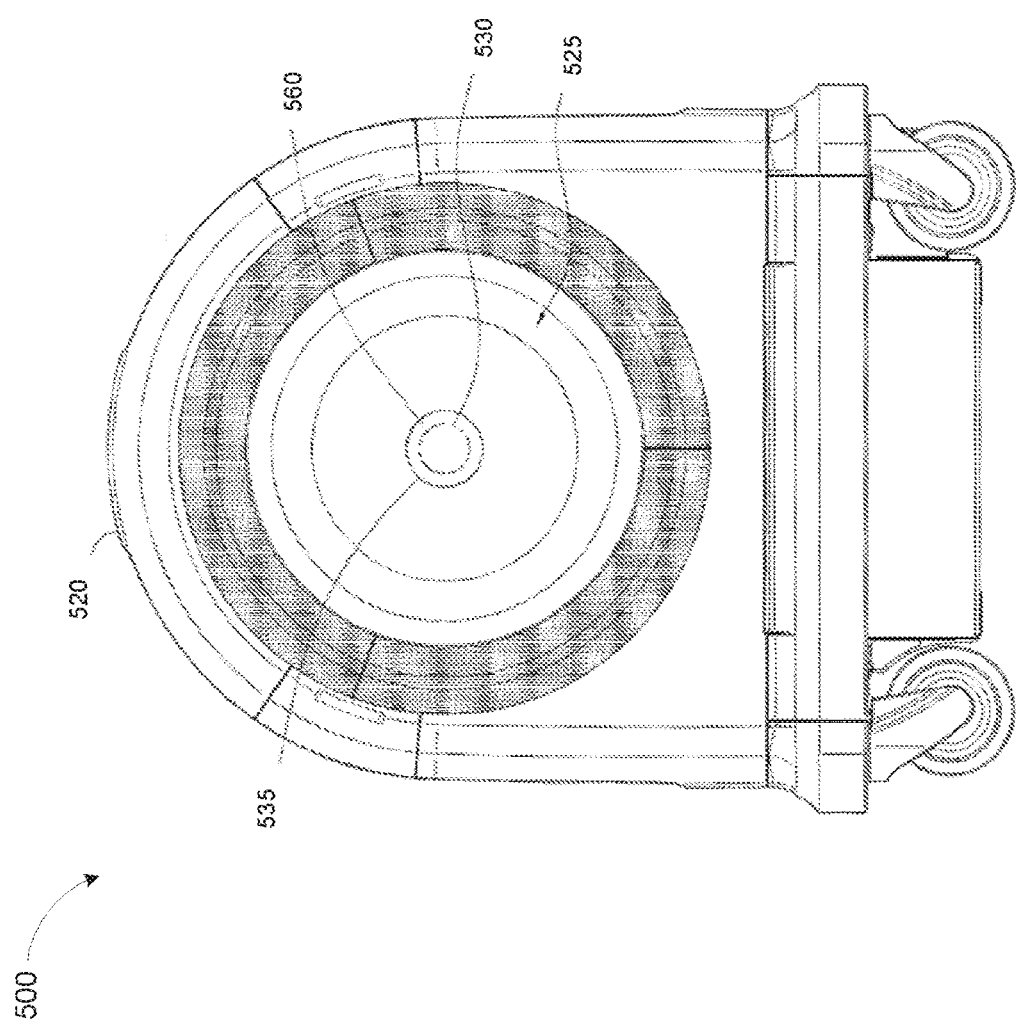

SYSTEMS AND METHODS FOR VOLUMETRIC ACQUISITION IN A SINGLE-SIDED MRI SCANNER

CROSS-REFERENCE TO RELATED APPLICATIONS

The present application is a continuation application claiming priority under 35 U.S.C. § 120 to U.S. patent application Ser. No. 17/438,898, entitled "SYSTEMS AND METHODS FOR VOLUMETRIC ACQUISITION IN A SINGLE-SIDED MRI SCANNER," filed Sep. 13, 2021, which is a U.S. National Stage Entry under 35 U.S.C. § 371 of International PCT Application No. PCT/US2020/024778, entitled "SYSTEMS AND METHODS FOR VOLUMETRIC ACQUISITION IN A SINGLE-SIDED MRI SYSTEM," filed Mar. 25, 2020, which claims the benefit of priority under 35 U.S.C. § 119(e) to U.S. Provisional Application No. 62/823,511, entitled "SYSTEMS AND METHODS FOR VOLUMETRIC ACQUISITION IN A SINGLE-SIDED MRI SYSTEM", filed on Mar. 25, 2019, which are each incorporated by reference herein in their respective entireties.

BACKGROUND

The embodiments disclosed herein are generally directed towards systems and methods for effectively collecting nuclear magnetic resonance spectra and magnetic resonance images in inhomogeneous fields.

Several methods exist for collecting nuclear magnetic resonance (NMR) spectra and magnetic resonance (MR) images in inhomogeneous fields. Typically, the inhomogeneity of the field is a nuisance to be avoided. Rarely is the inhomogeneous field a source of spatial information. Relevant methods for imaging in inhomogeneous fields include use of wide bandwidth pulses and multi-slice excitation. Both however deal with the challenge of imaging in an inhomogeneous permanent field. Therefore, there is a need for improved methods using wide bandwidth pulses and multi-slice excitation for collecting NMR spectra and MR images in inhomogeneous fields.

SUMMARY

In accordance with various embodiments, a method for performing magnetic resonance imaging is provided. The method includes providing a magnetic resonance imaging system comprising a radio frequency receive system comprising a radio frequency receive coil, and a housing, wherein the housing comprises a permanent magnet for providing an inhomogeneous permanent gradient field, a radio frequency transmit system, and a single-sided gradient coil set. The method further comprises placing the receive coil proximate a target subject; applying a sequence of chirped pulses via the transmit system; applying a multi-slice excitation along the inhomogeneous permanent gradient field; applying a plurality of gradient pulses via the gradient coil set orthogonal to the inhomogeneous permanent gradient field; acquiring a signal of the target subject via the receive system, wherein the signal comprises at least two chirped pulses; and forming a magnetic resonance image of the target subject.

In accordance with various embodiments, a method for performing magnetic resonance imaging is provided. The method includes providing an imaging system comprising a radio frequency receive coil, and a permanent magnet for providing a permanent gradient field. The method further comprises placing the receive coil proximate a target subject; applying a sequence of chirped pulses having a wide bandwidth; applying a multi-slice excitation along the permanent gradient field, wherein the multi-slice excitation includes exciting multiple slices along an axis of the permanent gradient field, wherein each of the multiple slices has a bandwidth that is similar to the wide bandwidth of the chirped pulses; applying a phase encoding field along two orthogonal directions perpendicular to the axis of the permanent gradient field; and acquiring a magnetic resonance image of the target subject.

In accordance with various embodiments, a method for performing magnetic resonance imaging is provided. The method includes providing a permanent gradient magnetic field; placing a receive coil proximate a target subject; applying a sequence of chirped pulses having a wide bandwidth; selecting a slice selection gradient having the same wide bandwidth; applying a multi-slice excitation technique along an axis of the permanent gradient magnetic field; applying a plurality of gradient pulses orthogonal to the permanent gradient magnetic field; acquiring a signal of the target subject via the receive coil; and forming a magnetic resonance image of the target subject.

In accordance with various embodiments, a magnetic resonance imaging system is provided. The system includes a radio frequency receive system comprising a radio frequency receive coil configured to be placed proximate a target subject. The receive system is configured to deliver a signal of a target subject for forming a magnetic resonance image of the target subject, wherein the signal comprises at least two chirped pulses. The system includes a housing, wherein the housing comprises a permanent magnet for providing an inhomogeneous permanent gradient field. The imaging system is configured to apply a multi-slice excitation along the inhomogeneous permanent gradient field, a radio frequency transmit system configured to deliver a sequence of chirped pulses, and a single-sided gradient coil set configured to deliver a plurality of gradient pulses orthogonal to the inhomogeneous permanent gradient field.

In accordance with various embodiments, a non-transitory computer-readable medium in which a program is stored for causing a computer to perform a method for performing magnetic resonance imaging is provided. The method includes providing a magnetic resonance imaging system. The system includes a radio frequency receive system comprising a radio frequency receive coil, and a housing. The housing includes a permanent magnet for providing an inhomogeneous permanent gradient field, a radio frequency transmit system, and a single-sided gradient coil set. The method further includes placing the receive coil proximate a target subject; applying a sequence of chirped pulses via the transmit system; applying a multi-slice excitation along the inhomogeneous permanent gradient field; applying a plurality of gradient pulses via the gradient coil set orthogonal to the inhomogeneous permanent gradient field; acquiring a signal of the target subject via the receive system, wherein the signal comprises at least two chirped pulses; and forming a magnetic resonance image of the target subject.

In accordance with various embodiments, a non-transitory computer-readable medium in which a program is stored for causing a computer to perform a method for performing magnetic resonance imaging is provided. The method includes providing an imaging system comprising a radio frequency receive coil, and a permanent magnet for providing a permanent gradient field. The method further includes placing the receive coil proximate a target subject; applying a sequence of chirped pulses having a wide bandwidth; applying a multi-slice excitation along the permanent gradient field, wherein the multi-slice excitation includes exciting multiple slices along an axis of the permanent gradient field, wherein each of the multiple slices has a bandwidth that is similar to the wide bandwidth of the chirped pulses; applying a phase encoding field along two orthogonal directions perpendicular to the axis of the permanent gradient field; and acquiring a magnetic resonance image of the target subject.

In accordance with various embodiments, a non-transitory computer-readable medium in which a program is stored for causing a computer to perform a method for performing magnetic resonance imaging is provided. The method includes providing a permanent gradient magnetic field; placing a receive coil proximate a target subject; applying a sequence of chirped pulses having a wide bandwidth; selecting a slice selection gradient having the same wide bandwidth; applying a multi-slice excitation technique along an axis of the permanent gradient magnetic field; applying a plurality of gradient pulses orthogonal to the permanent gradient magnetic field; acquiring a signal of the target subject via the receive coil; and forming a magnetic resonance image of the target subject.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 5 is a schematic front view of a magnetic resonance imaging system 500, according to various embodiments.

Figure 1:
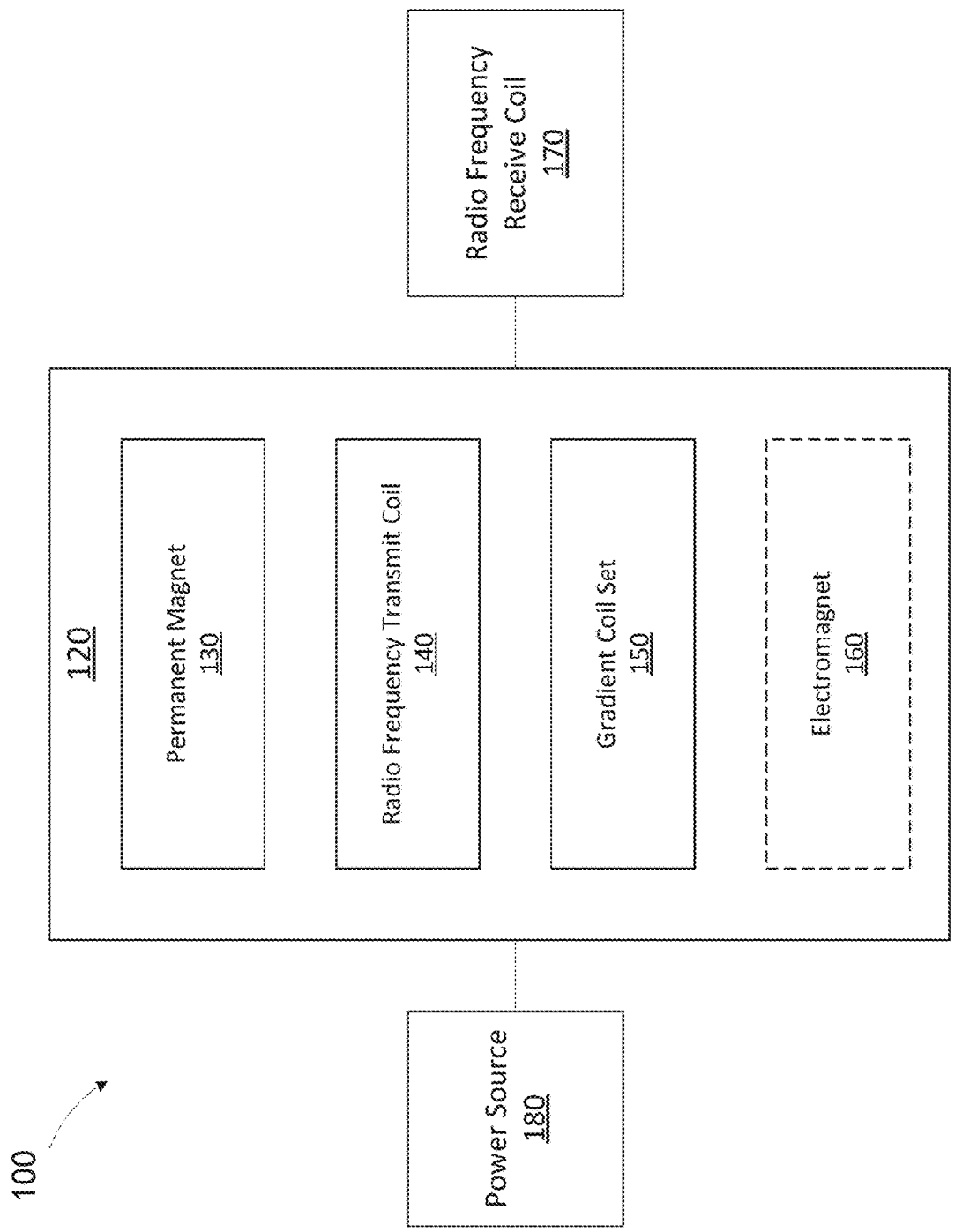
FIG. 1 is a schematic illustration of a magnetic resonance imaging system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

The following description of various embodiments is exemplary and explanatory only and is not to be construed as limiting or restrictive in any way. Other embodiments, features, objects, and advantages of the present teachings will be apparent from the description and accompanying drawings, and from the claims.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Unless defined otherwise, all technical and scientific terms used herein have the same meaning as commonly understood by one of ordinary skill in the art to which this invention belongs.

All publications mentioned herein are incorporated herein by reference for the purpose of describing and disclosing devices, compositions, formulations and methodologies which are described in the publication and which might be used in connection with the present disclosure.

As used herein, the terms "comprise", "comprises", "comprising", "contain", "contains", "containing", "have", "having" "include", "includes", and "including" and their variants are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus.

As discussed herein, and in accordance with various embodiments, the various systems, and various combinations of features that make up the various system embodiments, can include a magnetic resonance imaging system. In accordance with various embodiments, the magnetic resonance imaging system is a single-sided magnetic resonance imaging system that comprises a magnetic resonance imaging scanner or a magnetic resonance imaging spectrometer. In accordance with various embodiments, the magnetic resonance imaging system can include a magnet assembly for providing a magnetic field required for imaging an anatomical portion of a patient. In accordance with various embodiments, the magnetic resonance imaging system can be configured for imaging in a region of interest which resides outside of the magnet assembly.

Typical magnet resonant assemblies used in modern magnetic resonance imaging systems include, for example, a birdcage coil configuration. A typical birdcage configuration includes, for example, a radio frequency transmission (transmit) coil that can include two large rings placed on opposite sides of the imaging region (i.e., the region of interest where the patient resides) that are each electrically connected by one or more rungs. Since the imaging signal improves the more the coil surrounds the patient, the birdcage coil is typically configured to encompass a patient so that the signal produced from within the imaging region, i.e., the region of interest where the anatomical target portion of the patient resides, is sufficiently uniform. To improve patient comfort and reduce burdensome movement limitations of the current magnetic resonance imaging systems, the disclosure as described herein generally relates to a magnetic resonance imaging system that includes a single-sided magnetic resonance imaging system and its applications.

As described herein, the disclosed single-sided magnetic resonance imaging system can be configured to image the patient from one side while providing access to the patient from both sides. This is possible due to the single-sided magnetic resonance imaging system that contains an access aperture (also referred to herein as "aperture", "hole" or "bore"), which is configured to project magnetic fields in the region of interest which resides completely outside of the magnet assembly and the magnetic resonance imaging system. Since not being completely surrounded by the electromagnetic field producing materials and imaging system components as in current state of the art systems, the novel single-sided configuration as described herein offer less restriction in patient movement while reducing unnecessary burden during situating and/or removing of the patient from the magnetic resonance imaging system. In accordance with various embodiments as described herein, the patient would not feel entrapped in the disclosed magnetic resonance imaging system with the placement of the magnet assembly on the side of the patient during imaging. The configuration that enables single-sided or imaging from a side is made possible by the disclosed system components as discussed herein.

System Embodiments

In accordance with various embodiments, the various systems, and various combinations of features that make up the various system components and embodiments of the disclosed magnetic resonance imaging system are disclosed herein.

In accordance with various embodiments, a magnetic resonance imaging system is disclosed herein. In accordance with various embodiments, the system includes a housing having a front surface, a permanent magnet for providing a static magnetic field, an access aperture (also referred to herein as "aperture", "hole" or "bore") within the permanent magnet assembly, a radio frequency transmit coil, and a single-sided gradient coil set. In accordance with various embodiments, the radio frequency transmit coil and the single-sided gradient coil set are positioned proximate to the front surface. In accordance with various embodiments, the system includes an electromagnet, a radio frequency receive coil, and a power source. In accordance with various embodiments, the power source is configured to flow current through at least one of the radio frequency transmit coil, the single-sided gradient coil set, or the electromagnet to generate an electromagnetic field in a region of interest. In accordance with various embodiments, the region of interest resides outside the front surface.

In accordance with various embodiments, the radio frequency transmit coil and the single-sided gradient coil set are located on the front surface. In accordance with various embodiments, the front surface is a concave surface. In accordance with various embodiments, the permanent magnet has an aperture through center of the permanent magnet. In accordance with various embodiments, the static magnetic field of the permanent magnet ranges from 1 mT to 1 T. In accordance with various embodiments, the static magnetic field of the permanent magnet ranges from 10 mT to 195 mT.

In accordance with various embodiments, the radio frequency transmit coil includes a first ring and a second ring that are connected via one or more capacitors and/or one or more rungs. In accordance with various embodiments, the radio frequency transmit coil is non-planar and oriented to partially surround the region of interest. In accordance with various embodiments, the single-sided gradient coil set is non-planar and oriented to partially surround the region of interest. In accordance with various embodiments, the single-sided gradient coil set is configured to project a magnetic field gradient to the region of interest. In accordance with various embodiments, the single-sided gradient coil set includes one or more first spiral coils at a first position and one or more second spiral coils at a second position, the first position and the second position being located opposite each other about a center region of the single-sided gradient coil set. In accordance with various embodiments, the single-sided gradient coil set has a rise time less than 10 µs.

In accordance with various embodiments, the electromagnet is configured to alter the static magnetic field of the permanent magnet within the region of interest. In accordance with various embodiments, the electromagnet has a magnetic field strength from 10 mT to 1 T. In accordance with various embodiments, the radio frequency receive coil is a flexible coil configured to be affixed to an anatomical portion of a patient for imaging within the region of interest. In accordance with various embodiments, the radio frequency receive coil is in one of a single-loop coil configuration, figure-8 coil configuration, or butterfly coil configuration, wherein the coil is smaller than the region of interest. In accordance with various embodiments, the radio frequency transmit coil and the single-sided gradient coil set are concentric about the region of interest. In accordance with various embodiments, the magnetic resonance imaging system is a single-sided magnetic resonance imaging system that comprises a bore having an opening positioned about a center region of the front surface.

In accordance with various embodiments, a magnetic resonance imaging system is disclosed herein. In accordance with various embodiments, the system includes a housing having a concave front surface, a permanent magnet for providing a static magnetic field, a radio frequency transmit coil, and at least one gradient coil set. In accordance with various embodiments, the radio frequency transmit coil and the at least one gradient coil set are positioned proximate to the concave front surface. In accordance with various embodiments, the radio frequency transmit coil and the at least one gradient coil set are configured to generate an electromagnetic field in a region of interest. In accordance with various embodiments, the region of interest resides outside the concave front surface. In accordance with various embodiments, the system includes a radio frequency receive coil for detecting signal in the region of interest.

In accordance with various embodiments, the radio frequency transmit coil and the single-sided gradient coil set are located on the concave front surface. In accordance with various embodiments, the static magnetic field of the permanent magnet ranges from 1 mT to 1 T. In accordance with various embodiments, the static magnetic field of the permanent magnet ranges from 10 mT to 195 mT. In accordance with various embodiments, the radio frequency transmit coil comprises a first ring and a second ring that are connected via one or more capacitors and/or one or more rungs. In accordance with various embodiments, the radio frequency transmit coil is non-planar and oriented to partially surround the region of interest. In accordance with various embodiments, the at least one gradient coil set is non-planar, single-sided, and oriented to partially surround the region of interest. In accordance with various embodiments, the at least one gradient coil set is configured to project magnetic field gradient in the region of interest.

In accordance with various embodiments, the at least one gradient coil set comprises one or more first spiral coils at a first position and one or more second spiral coils at a second position, the first position and the second position being located opposite each other about a center region of the at least one gradient coil set. In accordance with various embodiments, the at least one gradient coil set has a rise time less than 10 µs. In accordance with various embodiments, the permanent magnet has an aperture through center of the permanent magnet. In accordance with various embodiments, the system further includes an electromagnet configured to alter the static magnetic field of the permanent magnet within the region of interest. In accordance with various embodiments, the electromagnet has a magnetic field strength from 10 mT to 1 T. In accordance with various embodiments, the radio frequency receive coil is a flexible coil configured to be affixed to an anatomical portion of a patient for imaging within the region of interest. In accordance with various embodiments, the radio frequency receive coil is in one of a single-loop coil configuration, figure-8 coil configuration, or butterfly coil configuration, where the coil is smaller than the region of interest.

In accordance with various embodiments, the radio frequency transmit coil and the at least one gradient coil set are concentric about the region of interest. In accordance with various embodiments, the magnetic resonance imaging system is a single-sided magnetic resonance imaging system that comprises a magnetic resonance imaging scanner or a magnetic resonance imaging spectrometer.

FIG. 1 is a schematic illustration of a magnetic resonance imaging system 100, in accordance with various embodiments. The system 100 includes a housing 120. As shown in FIG. 1, the housing 120 includes a permanent magnet 130, a radio frequency transmit coil 140, a gradient coil set 150, an optional electromagnet 160, a radio frequency receive coil 170, and a power source 180. In accordance with various embodiments, the system 100 can include various electronic components, such as for example, but not limited to a varactor, a PIN diode, a capacitor, or a switch, including a micro-electro-mechanical system (MEMS) switch, a solid state relay, or a mechanical relay. In accordance with various embodiments, the various electronic components listed above can be configured with the radio frequency transmit coil 140.

Figure 2B:
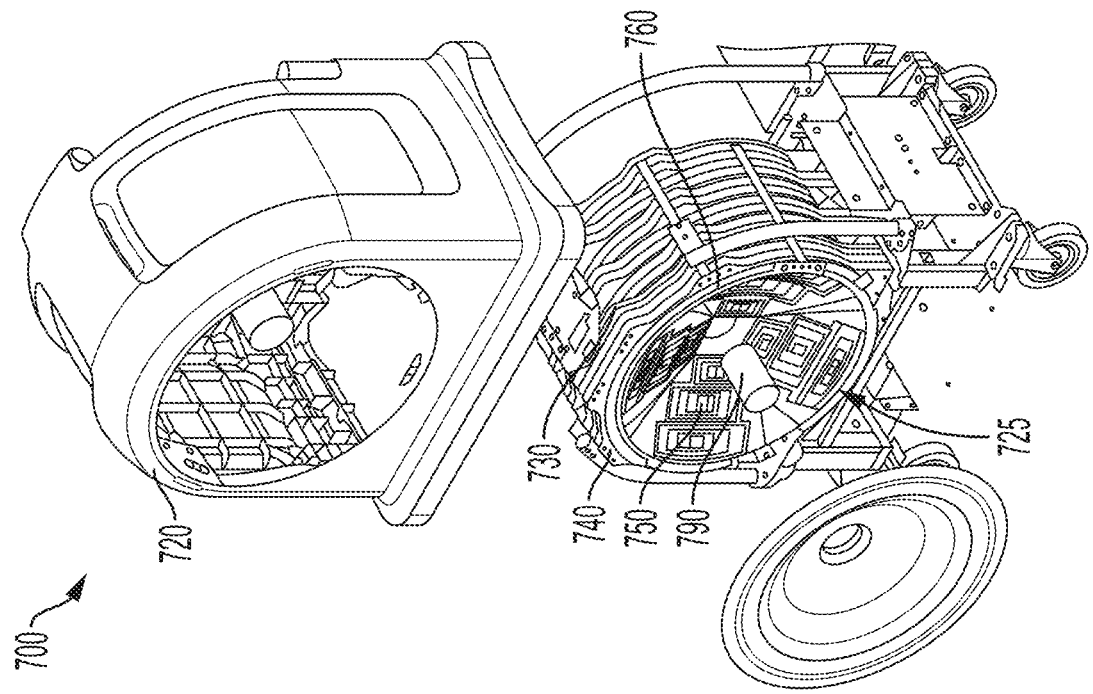
FIG. 2B illustrates an exploded view of the magnetic resonance imaging system shown in FIG. 2A.
Figure 2A:
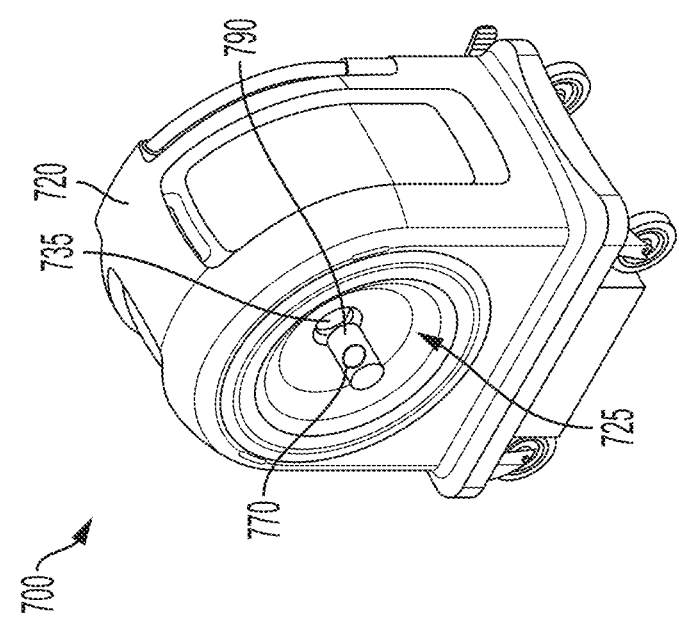
FIG. 2A is a schematic illustration of a magnetic resonance imaging system, in accordance with various embodiments.
Figure 2D:
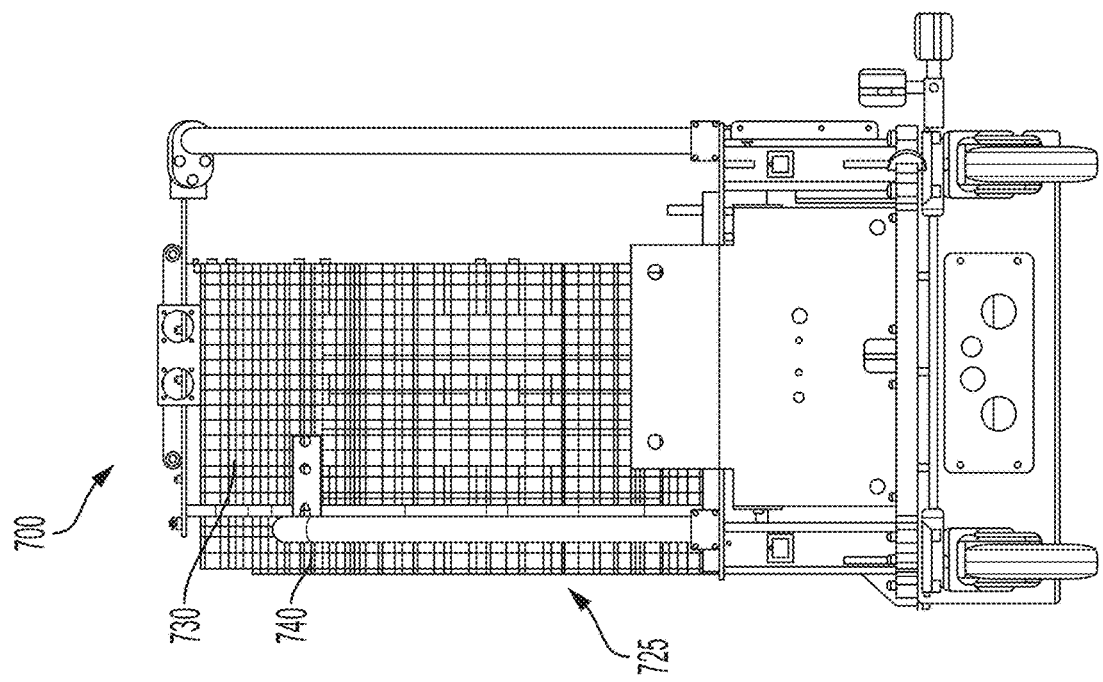
FIG. 2D is a schematic side view of the magnetic resonance imaging system shown in FIG. 2A, in accordance with various embodiments.
Figure 2C:
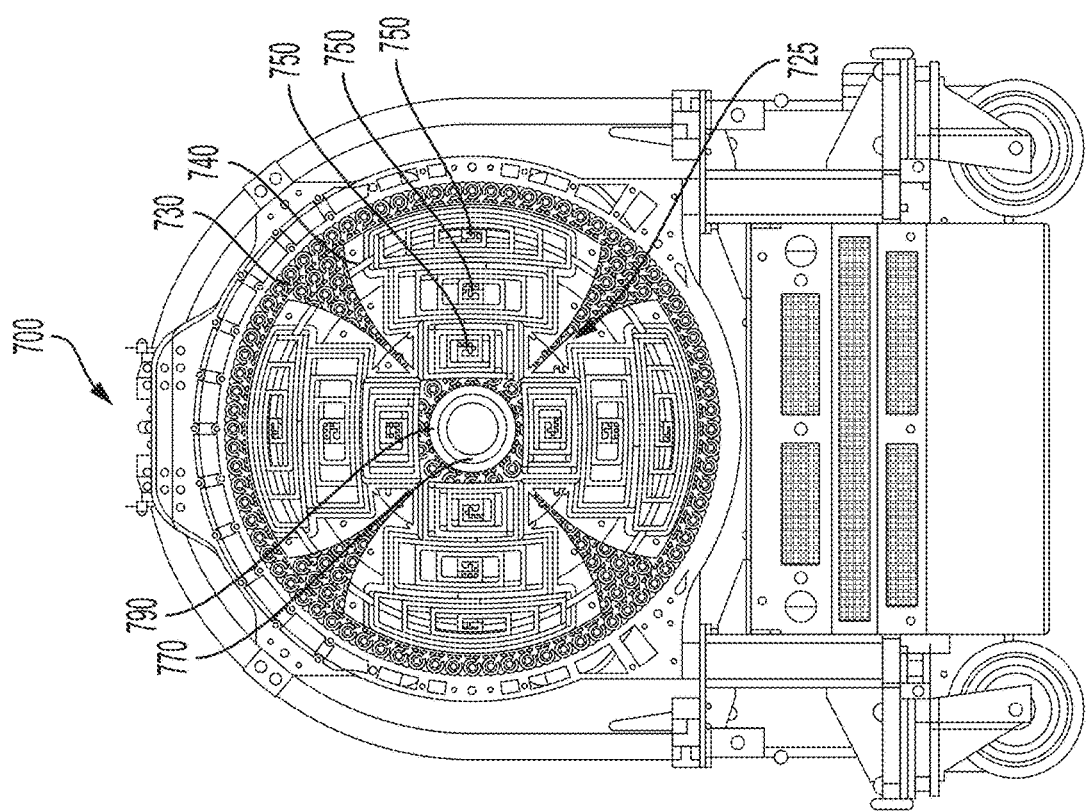
FIG. 2C is a schematic front view of the magnetic resonance imaging system shown in FIG. 2A, in accordance with various embodiments.

FIG. 2A is a schematic illustration of a magnetic resonance imaging system 200, in accordance with various embodiments. FIG. 2B illustrates an exploded view of the magnetic resonance imaging system 200. FIG. 2C is a schematic front view of the magnetic resonance imaging system 200, in accordance with various embodiments. FIG. 2D is a schematic side view of the magnetic resonance imaging system 200, in accordance with various embodiments. As shown in FIGS. 2A and 2B, the magnetic resonance imaging system 200 includes a housing 220. The housing 220 includes a front surface 225. In accordance with various embodiments, the front surface 225 can be a concave front surface. In accordance with various embodiments, the front surface 225 can be a recessed front surface.

As shown in FIGS. 2A and 2B, the housing 220 includes a permanent magnet 230, a radio frequency transmit coil 240, a gradient coil set 250, an optional electromagnet 260, and a radio frequency receive coil 270. As shown in FIGS. 2C and 2D, the permanent magnet 230 can include a plurality of magnets disposed in an array configuration. The plurality of magnets of the permanent magnet 230 are illustrated to cover an entire surface as shown in the front view of FIG. 2C and illustrated as bars in a horizontal direction as shown in the side view of FIG. 2D. As shown in FIG. 2A, the main permanent magnet might include an access aperture 235 for accessing the patient from multiple sides of the system.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Permanent Magnet

As discussed herein, and in accordance with various embodiments, the various systems, and various combinations of features that make up the various system embodiments, can include a permanent magnet.

In accordance with various embodiments, the permanent magnet 230 provides a static magnetic field in a region of interest 290 (also referred to herein as "given field of view"). In accordance with various embodiments, the permanent magnet 230 can include a plurality of cylindrical permanent magnets in parallel configuration as shown in FIGS. 2C and 2D. In accordance with various embodiments, the permanent magnet 230 can include any suitable magnetic materials, including but not limited, to rare-earth based magnetic materials, such as for example, Nd-based magnetic materials, and the like. As shown in FIG. 2A, the main permanent magnet might include an access aperture 235 for accessing the patient from multiple sides of the system.

In accordance with various embodiments, the static magnetic field of the permanent magnet 230 may vary from about 50 mT to about 60 mT, about 45 mT to about 65 mT, about 40 mT to about 70 mT, about 35 mT to about 75 mT, about 30 mT to about 80 mT, about 25 mT to about 85 mT, about 20 mT to about 90 mT, about 15 mT to about 95 mT and about 10 mT to about 100 mT to a given field of view. The magnetic field may also vary from about 10 mT to about 15 mT, about 15 mT to about 20 mT, about 20 mT to about 25 mT, about 25 mT to about 30 mT, about 30 mT to about 35 mT, about 35 mT to about 40 mT, about 40 mT to about 45 mT, about 45 mT to about 50 mT, about 50 mT to about 55 mT, about 55 mT to about 60 mT, about 60 mT to about 65 mT, about 65 mT to about 70 mT, about 70 mT to about 75 mT, about 75 mT to about 80 mT, about 80 mT to about 85 mT, about 85 mT to about 90 mT, about 90 mT to about 95 mT, and about 95 mT to about 100 mT. In accordance with various embodiments, the static magnetic field of the permanent magnet 230 may also vary from about 1 mT to about 1 T, about 10 mT to about 195 mT, about 15 mT to about 900 mT, about 20 mT to about 800 mT, about 25 mT to about 700 mT, about 30 mT to about 600 mT, about 35 mT to about 500 mT, about 40 mT to about 400 mT, about 45 mT to about 300 mT, about 50 mT to about 200 mT, about 50 mT to about 100 mT, about 45 mT to about 100 mT, about 40 mT to about 100 mT, about 35 mT to about 100 mT, about 30 mT to about 100 mT, about 25 mT to about 100 mT, about 20 mT to about 100 mT, and about 15 mT to about 100 mT.

In accordance with various embodiments, the permanent magnet 230 can include a bore 235 in its center. In accordance with various embodiments, the permanent magnet 230 may not include a bore. In accordance with various embodiments, the bore 235 can have a diameter between 1 inch and 20 inches. In accordance with various embodiments, the bore 235 can have a diameter between 1 inch and 4 inches, between 4 inches and 8 inches, and between 10 inches and 20 inches. In accordance with various embodiments, the given field of view can be a spherical or cylindrical field of view, as shown in FIGS. 2A and 2B. In accordance with various embodiments, the spherical field of view can be between 2 inches and 20 inches in diameter. In accordance with various embodiments, the spherical field of view can have a diameter between 1 inch and 4 inches, between 4 inches and 8 inches, and between 10 inches and 20 inches. In accordance with various embodiments, the cylindrical field of view is approximately between 2 inches and 20 inches in length. In accordance with various embodiments, the cylindrical field of view can have a length between 1 inch and 4 inches, between 4 inches and 8 inches, and between 10 inches and 20 inches.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Radio Frequency Transmit Coil

As discussed herein, and in accordance with various embodiments, the various systems, and various combinations of features that make up the various system embodiments, can also include a radio frequency transmit coil.

Figure 3:
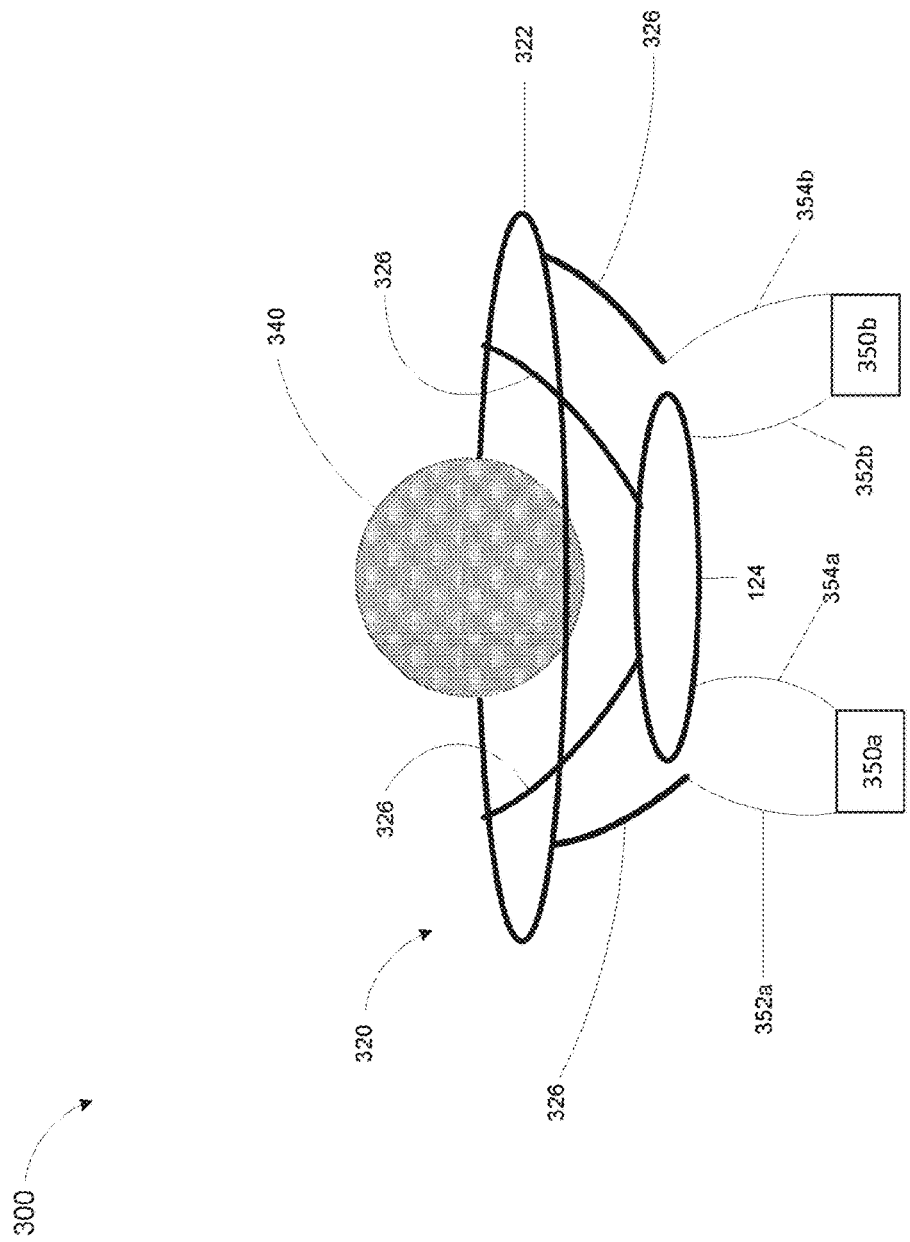
FIG. 3 is a schematic view of an implementation of a magnetic imaging apparatus, according to various embodiments.

FIG. 3 is a schematic view of an implementation of a magnetic imaging apparatus 300, according to various embodiments. As shown in FIG. 3, the apparatus 300 includes a radio frequency transmit coil 320 that projects the RF power outwards away from the coil 320. The coil 320 has two rings 322 and 324 that are connected by one or more rungs 326. As shown in FIG. 3, the coil 320 is also connected to a power source 350a and/or a power source 350b (collectively referred to herein as "power source 350"). In accordance with various embodiments, power sources 350a and 350b can be configured for power input and/or signal input, and can generally be referred to as coil input. In accordance with various embodiments, the power source 350a and/or 350b are configured to provide contact via electrical contacts 352a and/or 352b (collectively referred to herein as "electrical contact 352"), and electrical contacts 354a and/or 354b (collectively referred to herein as "electrical contact 354b") by attaching the electrical contacts 352 and 354 to one or more rungs 326. The coil 320 is configured to project a uniform RF field within a field of view 340. In accordance with various embodiments, the field of view 340 is a region of interest for magnetic resonance imaging (i.e., imaging region) where a patient resides. Since the patient resides in the field of view 340 away from the coil 320, the apparatus 300 is suitable for use in a single-sided magnetic resonance imaging system. In accordance with various embodiments, the coil 320 can be powered by two signals that are 90 degrees out of phase from each other, for example, via quadrature excitation.

In accordance with various embodiments, the coil 320 includes the ring 322 and the ring 324 that are positioned co-axially along the same axis but at a distance away from each other, as shown in FIG. 3. In accordance with various embodiments, the ring 322 and the ring 324 are separated by a distance ranging from about 0.1 m to about 10 m. In accordance with various embodiments, the ring 322 and the ring 324 are separated by a distance ranging from about 0.2 m to about 5 m, about 0.3 m to about 2 m, about 0.2 m to about 1 m, about 0.1 m to about 0.8 m, or about 0.1 m to about 1 m, inclusive of any separation distance therebetween. In accordance with various embodiments, the coil 320 includes the ring 322 and the ring 324 that are positioned non-co-axially but along the same direction and separated at a distance ranging from about 0.2 m to about 5 m. In accordance with various embodiments, the ring 322 and the ring 324 can also be tilted with respect to each other. In accordance with various embodiments, the tilt angle can be from 1 degree to 90 degrees, from 1 degree to 5 degrees, from 5 degrees to 10 degrees, from 10 degrees to 25 degrees, from 25 degrees to 45 degrees, and from 45 degrees to 90 degrees.

In accordance with various embodiments, the ring 322 and the ring 324 have the same diameter. In accordance with various embodiments, the ring 322 and the ring 324 have different diameters and the ring 322 has a larger diameter than the ring 324, as shown in FIG. 3. In accordance with various embodiments, the ring 322 and the ring 324 have different diameters and the ring 322 has a smaller diameter than the ring 324. In accordance with various embodiments, the ring 322 and the ring 324 of the coil 320 are configured to create the imaging region in the field of view 340 containing a uniform RF power profile within the field of view 340, a field of view that is not centered within the RF-TX coil and is instead projected outwards in space from the coil itself.

In accordance with various embodiments, the ring 322 has a diameter between about 10 μm and about 10 m. In accordance with various embodiments, the ring 322 has a diameter between about 0.001 m and about 9 m, between about 0.01 m and about 8 m, between about 0.03 m and about 6 m, between about 0.05 m and about 5 m, between about 0.1 m and about 3 m, between about 0.2 m and about 2 m, between about 0.3 m and about 1.5 m, between about 0.5 m and about 1 m, or between about 0.01 m and about 3 m, inclusive of any diameter therebetween.

In accordance with various embodiments, the ring 324 has a diameter between about 10 μm and about 10 m. In accordance with various embodiments, the ring 324 has a diameter between about 0.001 m and about 9 m, between about 0.01 m and about 8 m, between about 0.03 m and about 6 m, between about 0.05 m and about 5 m, between about 0.1 m and about 3 m, between about 0.2 m and about 2 m, between about 0.3 m and about 1.5 m, between about 0.5 m and about 1 m, or between about 0.01 m and about 3 m, inclusive of any diameter therebetween.

In accordance with various embodiments, the ring 322 and the ring 324 are connected by one or more rungs 326, as shown in FIG. 3. In accordance with various embodiments, the one or more rungs 326 are connected to the ring 322 and 324 so as to form a single electrical circuit loop (or single current loop). As shown in FIG. 3, for example, one end of the one or more rungs 326 is connected to the electrical contact 352 of the power source 350 and another end of the one or more rungs 326 be connected to the electrical contact 354 so that the coil 320 completes an electrical circuit.

In accordance with various embodiments, the ring 322 is a discontinuous ring and the electrical contact 352 and the electrical contact 354 can be electrically connected to two opposite ends of the ring 322 to form an electrical circuit powered by the power source 350. Similarly, in accordance with various embodiments, the ring 324 is a discontinuous ring and the electrical contact 352 and the electrical contact 354 can be electrically connected to two opposite ends of the ring 324 to form an electrical circuit powered by the power source 350.

In accordance with various embodiments, the rings 322 and 324 are not circular and can instead have a cross section that is elliptical, square, rectangular, or trapezoidal, or any shape or form having a closed loop. In accordance with various embodiments, the rings 322 and 324 may have cross sections that vary in two different axial planes with the primary axis being a circle and the secondary axis having a sinusoidal shape or some other geometric shape. In accordance with various embodiments, the coil 320 may include more than two rings 322 and 324, each connected by rungs that span and connect all the rings. In accordance with various embodiments, the coil 320 may include more than two rings 322 and 324, each connected by rungs that alternate connection points between rings. In accordance with various embodiments, the ring 322 may contain a physical aperture for access. In accordance with various embodiments, the ring 322 may be a solid sheet without a physical aperture.

In accordance with various embodiments, the coil 320 generates an electromagnetic field (also referred to herein as "magnetic field") strength between about 1 μT and about 10 mT. In accordance with various embodiments, the coil 320 can generate a magnetic field strength between about 10 μT and about 5 mT, about 50 μT and about 1 mT, or about 100 μT and about 1 mT, inclusive of any magnetic field strength therebetween.

In accordance with various embodiments, the coil 320 generates an electromagnetic field that is pulsed at a radio frequency between about 1 kHz and about 2 GHz. In accordance with various embodiments, the coil 320 generates a magnetic field that is pulsed at a radio frequency between about 1 kHz and about 1 GHz, about 10 kHz and about 800 MHz, about 50 kHz and about 300 MHz, about 100 kHz and about 100 MHz, about 10 kHz and about 10 MHz, about 10 kHz and about 5 MHz, about 1 kHz and about 2 MHz, about 50 kHz and about 150 kHz, about 80 kHz and about 120 kHz, about 800 kHz and about 1.2 MHz, about 100 kHz and about 10 MHz, or about 1 MHz and about 5 MHz, inclusive of any frequencies therebetween.

In accordance with various embodiments, the coil 320 is oriented to partially surround the region of interest. In accordance with various embodiments, the ring 322, the ring 324, and the one or more rungs 326 are non-planar to each other. Said another way, the ring 322, the ring 324, and the one or more rungs 326 form a three-dimensional structure that surrounds the region of interest where a patient resides. In accordance with various embodiments, the ring 322 is closer to the region of interest than the ring 324, as shown in FIG. 3. In accordance with various embodiments, the region of interest has a size of about 0.1 m to about 1 m. In accordance with various embodiments, the region of interest is smaller than the diameter of the ring 322. In accordance with various embodiments, the region of interest is smaller than both the diameter of the ring 324 and the diameter of the ring 322, as shown in FIG. 3. In accordance with various embodiments, the region of interest has a size that is smaller than the diameter of the ring 322 and larger than the diameter of the ring 324.

In accordance with various embodiments, the ring 322, the ring 324, or the rungs 326 include the same material. In accordance with various embodiments, the ring 322, the ring 324, or the rungs 326 include different materials. In accordance with various embodiments, the ring 322, the ring 324, or the rungs 326 include hollow tubes or solid tubes. In accordance with various embodiments, the hollow tubes or solid tubes can be configured for air or fluid cooling. In accordance with various embodiments, each of the ring 322 or the ring 324 or the rungs 326 includes one or more electrically conductive windings. In accordance with various embodiments, the windings include litz wires or any electrical conducting wires. These additional windings could be used to improve performance by lowering the resistance of the windings at the desired frequency. In accordance with various embodiments, the ring 322, the ring 324, or the rungs 326 include copper, aluminum, silver, silver paste, or any high electrical conducting material, including metal, alloys or superconducting metal, alloys or non-metal. In accordance with various embodiments, the ring 322, the ring 324, or the rungs 326 may include metamaterials.

In accordance with various embodiments, the ring 322, the ring 324, or the rungs 326 may contain separate electrically non-conductive thermal control channels designed to maintain the temperature of the structure to a specified setting. In accordance with various embodiments, the thermal control channels can be made from electrically conductive materials and integrated as to carry the electrical current.

In accordance with various embodiments, the coil 320 includes one or more electronic components for tuning the magnetic field. The one or more electronic components can include a varactor, a PIN diode, a capacitor, or a switch, including a micro-electro-mechanical system (MEMS) switch, a solid state relay, or a mechanical relay. In accordance with various embodiments, the coil can be configured to include any of the one or more electronic components along the electrical circuit. In accordance with various embodiments, the one or more components can include mu metals, dielectrics, magnetic, or metallic components not actively conducting electricity and can tune the coil. In accordance with various embodiments, the one or more electronic components used for tuning includes at least one of dielectrics, conductive metals, metamaterials, or magnetic metals. In accordance with various embodiments, tuning the electromagnetic field includes changing the current or by changing physical locations of the one or more electronic components. In accordance with various embodiments, the coil is cryogenically cooled to reduce resistance and improve efficiency. In accordance with various embodiments, the first ring and the second ring comprise a plurality of windings or litz wires.

In accordance with various embodiments, the coil 320 is configured for a magnetic resonance imaging system that has a magnetic field gradient across the field of view. The field gradient allows for imaging slices of the field of view without using an additional electromagnetic gradient. As disclosed herein, the coil can be configured to generate a large bandwidth by combining multiple center frequencies, each with their own bandwidth. By superimposing these multiple center frequencies with their respective bandwidths, the coil 320 can effectively generate a large bandwidth over a desired frequency range between about 1 kHz and about 2 GHz. In accordance with various embodiments, the coil 320 generates a magnetic field that is pulsed at a radio frequency between about 10 kHz and about 800 MHz, about 50 kHz and about 300 MHz, about 100 kHz and about 100 MHz, about 10 kHz and about 10 MHz, about 10 kHz and about 5 MHz, about 1 kHz and about 2 MHz, about 50 kHz and about 150 kHz, about 80 kHz and about 120 kHz, about 800 kHz and about 1.2 MHz, about 100 kHz and about 10 MHz, or about 1 MHz and about 5 MHz, inclusive of any frequencies therebetween.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Gradient Coil Set

As discussed herein, and in accordance with various embodiments, the various systems, and various combinations of features that make up the various system embodiments, can also include a gradient coil set.

Figure 4:
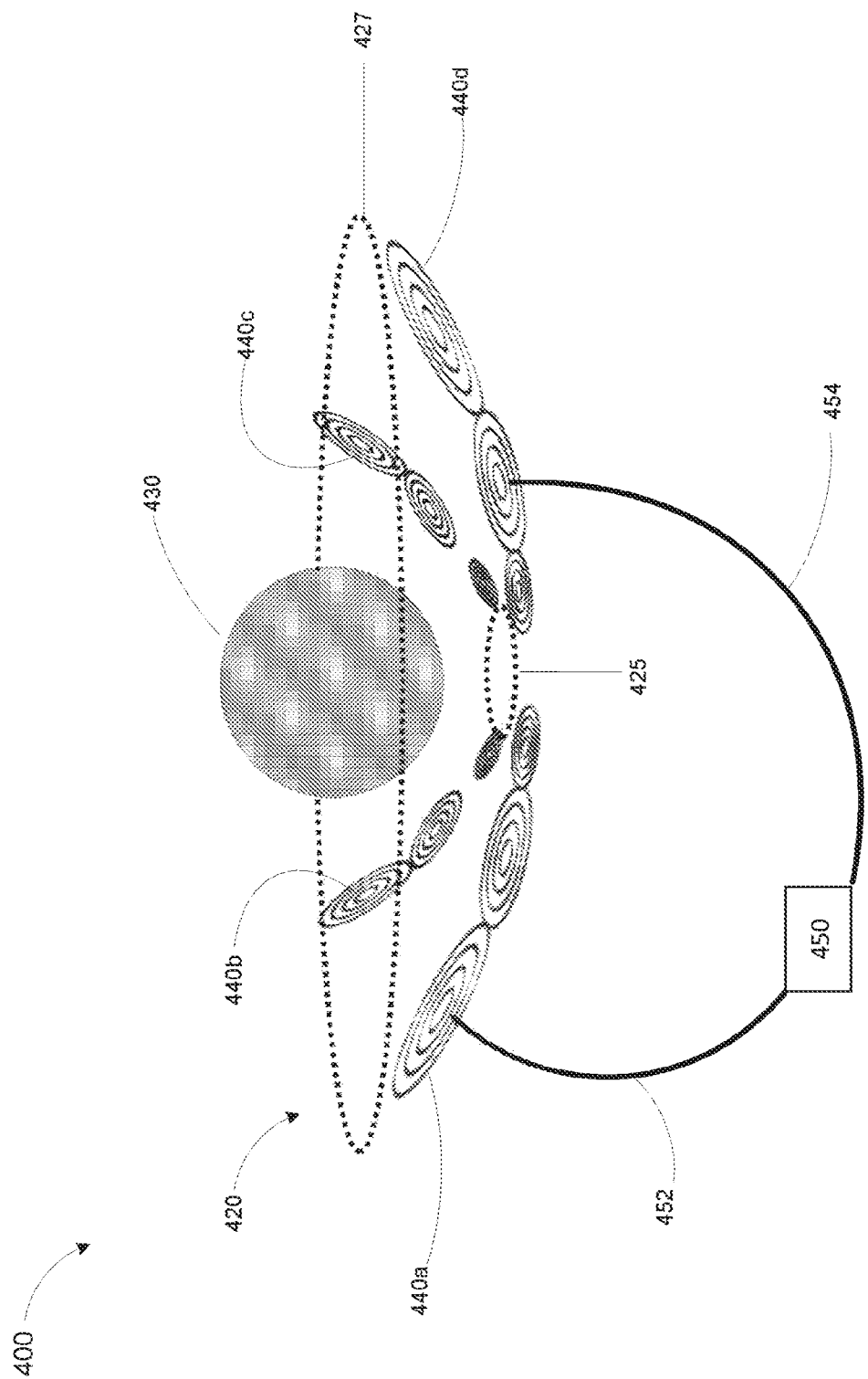
FIG. 4 is a schematic view of an implementation of a magnetic imaging apparatus, according to various embodiments.

FIG. 4 is a schematic view of an implementation of a magnetic imaging apparatus 400, according to various embodiments. As shown in FIG. 4, the apparatus 400 includes a gradient coil set 420 (also referred to herein as single-sided gradient coil set 420) that is configured to project a gradient magnetic field outwards away from the coil set 420 and within a field of view 430. In accordance with various embodiments, the field of view 430 is a region of interest for magnetic resonance imaging (i.e., imaging region) where a patient resides. Since the patient resides in the field of view 430 away from the coil set 420, the apparatus 400 is suitable for use in a single-sided MRI system.

As shown in the figure, the coil set 420 includes variously sized spiral coils in various sets of spiral coils 440a, 440b, 440c, and 440d (collectively referred to as "spiral coils 440"). Each set of the spiral coils 440 include at least one spiral coil and FIG. 4 is shown to include 3 spiral coils. In accordance with various embodiments, each spiral coil in the spiral coils 440 has an electrical contact at its center and an electrical contact output on the outer edge of the spiral coil so as to form a single running loop of electrically conducting material spiraling out from the center to the outer edge, or vice versa. In accordance with various embodiments, each spiral coil in the spiral coils 440 has a first electrical contact at a first position of the spiral coil and a second electrical contact at a second position the spiral coil so as to form a single running loop of electrically conducting material from the first position to the second position, or vice versa.

As shown in FIG. 4, the coil set 420 also includes an aperture 425 at its center where the spiral coils 440 are disposed around the aperture 425. The aperture 425 itself does not contain any coil material within it for generating magnetic material. The coil set 420 also includes an opening 427 on the outer edge of the coil set 420 to which the spiral coils 440 can be disposed. Said another way, the aperture 425 and the opening 427 define the boundaries of the coil set 420 within which the spiral coils 440 can be disposed. In accordance with various embodiments, the coil set 420 forms a bowl shape with a hole in the center.

In accordance with various embodiments, the spiral coils 440 form across the aperture 425. For example, the spiral coils 440a are disposed across from the spiral coils 440c with respect to the aperture 425. Similarly, the spiral coils 440b are disposed across from the spiral coils 440d with respect to the aperture 425. In accordance with various embodiments, the spiral coils 440 in the coil set 420 shown in FIG. 4 are configured to create spatial encoding in the magnetic gradient field within the field of view 430.

As shown in FIG. 4, the coil set 420 is also connected to a power source 450 via electrical contacts 452 and 454 by attaching the electrical contacts 452 and 454 to one or more of the spiral coils 440. In accordance with various embodiments, the electrical contact 452 is connected to one of the spiral coils 440, which is then connected to other spiral coils 440 in series and/or in parallel, and one other spiral coil 440 is then connected to the electrical contact 454 so as to form an electrical current loop. In accordance with various embodiments, the spiral coils 440 are all electrically connected in series. In accordance with various embodiments, the spiral coils 440 are all electrically connected in parallel. In accordance with various embodiments, some of the spiral coils 440 are electrically connected in series while other spiral coils 440 are electrically connected in parallel. In accordance with various embodiments, the spiral coils 440*a* are electrically connected in series while the spiral coils 440*b* are electrically connected in parallel. In accordance with various embodiments, the spiral coils 440*c* are electrically connected in series while the spiral coils 440*d* are electrically connected in parallel. The electrical connections between each spiral coil in the spiral coils 440 or each set of spiral coils 440 can be configured as needed to generate the magnetic field in the field of view 430.

In accordance with various embodiments, the coil set 420 includes the spiral coils 440 spread out as shown in FIG. 4. In accordance with various embodiments, each of the sets of spiral coils 440*a*, 440*b*, 440*c*, and 440*d* are configured in a line from the aperture 425 to the opening 427 so that each set of spiral coils is set apart from another by an angle of 90°. In accordance with various embodiments, 440*a* and 440*b* are set at 45° from one another, and 440*c* and 440*d* are set at 45° from one another, while 440*c* is set 135° on the other side of 440*b* and 440*d* is set 135° on the other side of 440*a*. In essence, any of the sets of spiral coils 440 can be configured in any arrangement for any number "n" of sets of spiral coils 440.

In accordance with various embodiments, the spiral coils 440 have the same diameter. In accordance with various embodiments, each of the sets of spiral coils 440*a*, 440*b*, 440*c*, and 440*d* have the same diameter. In accordance with various embodiments, the spiral coils 440 have different diameters. In accordance with various embodiments, each of the sets of spiral coils 440*a*, 440*b*, 440*c*, and 440*d* have different diameters. In accordance with various embodiments, the spiral coils in each of the sets of spiral coils 440*a*, 440*b*, 440*c*, and 440*d* have different diameters. In accordance with various embodiments, 440*a* and 440*b* have the same first diameter and 440*c* and 440*d* have the same second diameter, but the first diameter and the second diameter are not the same.

In accordance with various embodiments, each spiral coil in the spiral coils 440 has a diameter between about 10 µm and about 10 m. In accordance with various embodiments, each spiral coil in the spiral coils 440 has a diameter between about 0.001 m and about 9 m, between about 0.005 m and about 8 m, between about 0.01 m and about 6 m, between about 0.05 m and about 5 m, between about 0.1 m and about 3 m, between about 0.2 m and about 2 m, between about 0.3 m and about 1.5 m, between about 0.5 m and about 1 m, or between about 0.01 m and about 3 m, inclusive of any diameter therebetween.

In accordance with various embodiments, the spiral coils 440 are connected to form a single electrical circuit loop (or single current loop). As shown in FIG. 4, for example, one spiral coil in the spiral coils 440 is connected to the electrical contact 452 of the power source 450 and another spiral coil be connected to the electrical contact 454 so that the spiral coils 440 completes an electrical circuit.

In accordance with various embodiments, the coil set 420 generates an electromagnetic field strength (also referred to herein as "electromagnetic field gradient" or "gradient magnetic field") between about 1 µT and about 10 T. In accordance with various embodiments, the coil set 420 can generate an electromagnetic field strength between about 100 µT and about 1 T, about 1 mT and about 500 mT, or about 10 mT and about 100 mT, inclusive of any magnetic field strength therebetween. In accordance with various embodiments, the coil set 420 can generate an electromagnetic field strength greater than about 1 µT, about 10 µT, about 100 µT, about 1 mT, about 5 mT, about 10 mT, about 20 mT, about 50 mT, about 100 mT, or about 500 mT.

In accordance with various embodiments, the coil set 420 generates an electromagnetic field that is pulsed at a rate with a rise-time less than about 100 µs. In accordance with various embodiments, the coil set 420 generates an electromagnetic field that is pulsed at a rate with a rise-time less than about 1 µs, about 5 µs, about 10 µs, about 20 µs, about 30 µs, about 40 µs, about 50 µs, about 100 µs, about 200 µs, about 500 µs, about 1 ms, about 2 ms, about 5 ms, or about 10 ms.

In accordance with various embodiments, the coil set 420 is oriented to partially surround the region of interest in the field of view 430. In accordance with various embodiments, the spiral coils 440 are non-planar to each other. In accordance with various embodiments, the sets of spiral coils 440*a*, 440*b*, 440*c*, and 440*d* are non-planar to each other. Said another way, the spiral coils 440 and each of the sets of spiral coils 440*a*, 440*b*, 440*c*, and 440*d* form a three-dimensional structure that surrounds the region of interest in the field of view 430 where a patient resides.

In accordance with various embodiments, the spiral coils 440 include the same material. In accordance with various embodiments, the spiral coils 440 include different materials. In accordance with various embodiments, the spiral coils in set 440*a* include the same first material, the spiral coils in set 440*b* include the same second material, the spiral coils in set 440*c* include the same third material, the spiral coils in set 440*d* include the same fourth material, but the first, second, third and fourth materials are different materials. In accordance with various embodiments, the first and second materials are the same material, but that same material is different from the third and fourth materials, which are the same. In essence, any of the spiral coils 440 can be of the same material or different materials depending on the configuration of the coil set 420.

In accordance with various embodiments, the spiral coils 440 include hollow tubes or solid tubes. In accordance with various embodiments, the spiral coils 440 include one or more windings. In accordance with various embodiments, the windings include litz wires or any electrical conducting wires. In accordance with various embodiments, the spiral coils 440 include copper, aluminum, silver, silver paste, or any high electrical conducting material, including metal, alloys or superconducting metal, alloys or non-metal. In accordance with various embodiments, the spiral coils 440 include metamaterials.

In accordance with various embodiments, the coil set 420 includes one or more electronic components for tuning the magnetic field. The one or more electronic components can include a PIN diode, a mechanical relay, a solid state relay, or a switch, including a micro-electro-mechanical system (MEMS) switch. In accordance with various embodiments, the coil can be configured to include any of the one or more electronic components along the electrical circuit. In accordance with various embodiments, the one or more components can include mu metals, dielectrics, magnetic, or metallic components not actively conducting electricity and can tune the coil. In accordance with various embodiments, the one or more electronic components used for tuning includes at least one of conductive metals, metamaterials, or magnetic metals. In accordance with various embodiments, tuning the electromagnetic field includes changing the current or by changing physical locations of the one or more electronic components. In some implementations, the coil is cryogenically cooled to reduce resistance and improve efficiency.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Electromagnet

As discussed herein, and in accordance with various embodiments, the various systems, and various combinations of features that make up the various system embodiments, can also include an electromagnet.

FIG. 5 is a schematic front view of a magnetic resonance imaging system 500, according to various embodiments. In accordance with various embodiments, the system 500 can be any magnetic resonance imaging system, including for example, a single-sided magnetic resonance imaging system that comprises a magnetic resonance imaging scanner or a magnetic resonance imaging spectrometer, as disclosed herein.

As shown in FIG. 5, the system 500 includes a housing 520 that can house various components, including, for example but not limited to, magnets, electromagnets, coils for producing radio frequency fields, various electronic components, for example but not limited to, for controlling, powering, and/or monitoring of the system 500. In accordance with various embodiments, the housing 520 can house, for example, the permanent magnet 230, the radio frequency transmit coil 240, and/or the gradient coil set 250 within the housing 520. In accordance with various embodiments, the system 500 also includes a bore 535 in its center. As shown in FIG. 5, the housing 520 also includes a front surface 525 of the system 500. In accordance with various embodiments, the front surface 525 can be curved, flat, concave, convex, or otherwise have a straight or curvilinear surface. In accordance with various embodiments, the magnetic resonance imaging system 500 can be configured to provide a region of interest in field of view 530.

As shown in FIG. 5, the system 500 includes an electromagnet 560 disposed proximate to the front surface 525 of the system 500. In accordance with various embodiments, the electromagnet 560 is disposed proximate to the center of the front surface 525 on the front side of the system 500. In accordance with various embodiments, the electromagnet 560 can be a solenoid coil configured to create a field that either adds or subtracts from the magnetic field, for example, of the permanent magnet 230. In accordance with various embodiments, this field can create a prepolarizing field for enhancing the signal or contrast from the nuclear magnetic resonance.

As shown in FIG. 5, the given field of view 530 resides at the center of the front surface 525 of the system 500. In accordance with various embodiments, the electromagnet 560 is disposed within the given field of view 530. In accordance with various embodiments, the electromagnet 560 is disposed concentrically with the given field of view 530. In accordance with various embodiments, the electromagnet 560 can be inserted in the bore 535. In accordance with various embodiments, the electromagnet 560 can be placed proximate to the bore 535. For example, the electromagnet 560 can be placed in front, back or middle of the bore 535. In accordance with various embodiments, the electromagnet 560 can be placed proximate to, or at the entrance of the bore 535.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Radio Frequency Receive Coil

As discussed herein, and in accordance with various embodiments, the various systems, and various combinations of features that make up the various system embodiments, can also include a radio frequency receive coil.

Typical MR systems create a uniform field within the imaging region. This uniform field then generates a narrow band of magnetic resonance frequencies that can then be captured by a receive coil, amplified, and digitized by a spectrometer. Since frequencies are within a narrow well-defined bandwidth, hardware architecture is focused on creating a statically tuned RF-RX coil with an optimal coil quality factor. Many variations in coil architectures have been created that explore large single volume coils, coil arrays, parallelized coil arrays, or body specific coil arrays. However, these structures are all predicated on imaging a specific frequency close to the region of interest at high field strengths and small as possible within a magnetic bore.

In accordance with various embodiments, an MRI system is provided that can include a unique imaging region that can be offset from the face of a magnet and therefore unobstructed as compared to traditional scanners. In addition, this form factor can have a built-in magnetic field gradient that creates a range of field values over the region of interest. Lastly, this system can operate at a lower magnetic field strength as compared to typical MRI systems allowing for a relaxation on the RX coil design constraints and allowing for additional mechanisms like robotics to be used with the MRI.

The unique architecture of the main magnetic field of the MRI system, in accordance with various embodiments, can create a different set of optimization constraints. Because the imaging volume now extends over a broader range of magnetic resonance frequencies, the hardware can be configured to be sensitive to and capture the specific frequencies that are generated across the field of view. This frequency spread is usually much larger than a single receive coil tuned to a single frequency can be sensitive to. In addition, because the field strength can be much lower than traditional systems, and because signal intensity can be proportional to the field strength, it is generally considered to be beneficial to maximize the signal to noise ratio of the receive coil network. Methods are therefore provided, in accordance with various embodiments, to acquire the full range of frequencies that are generated within the field of view without loss of sensitivity.

In accordance with various embodiments, several methods are provided that can enable imaging within the MRI system. These methods can include combining 1) a variable tuned RF-RX coil; 2) a RF-RX coil array with elements tuned to frequencies that are dependent upon the spatial inhomogeneity of the magnetic field; 3) a ultralow-noise pre-amplifier design; and 4) an RF-RX array with multiple receive coils designed to optimize the signal from a defined and limited field of view for a specific body part. These methods can be combined in any combination as needed.

In accordance with various embodiments, a variable tuned RF-RX coil can comprise one or more electronic components for tuning the electromagnetic receive field. In accordance with various embodiments, the one or more electronic components can include at least one of a varactor, a PIN diode, a capacitor, an inductor, a MEMS switch, a solid state relay, or a mechanical relay. In accordance with various embodiments, the one or more electronic components used for tuning can include at least one of dielectrics, capacitors, inductors, conductive metals, metamaterials, or magnetic metals. In accordance with various embodiments, tuning the electromagnetic receive field includes changing the current or by changing physical locations of the one or more electronic components. In accordance with various embodiments, the coil is cryogenically cooled to reduce resistance and improve efficiency.

Figure 6A:
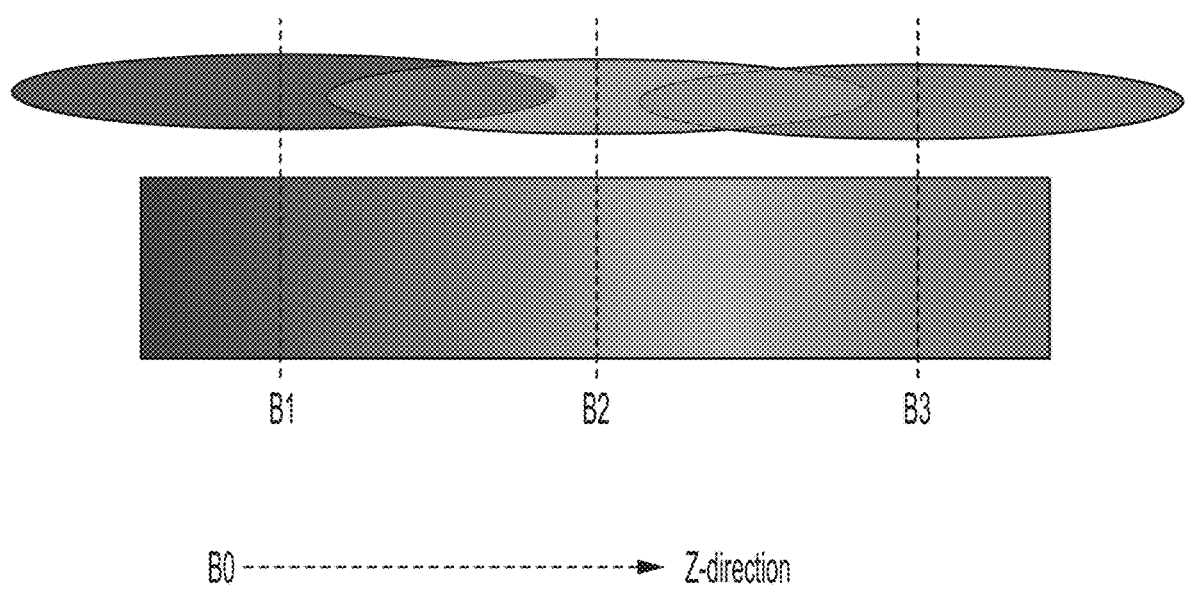
FIG. 6A is an example schematic illustration of a radio frequency receive coil (RF-RX) array including individual coil elements, in accordance with various embodiments.

In accordance with various embodiments, the RF-RX array can be comprised of individual coil elements that are each tuned to a variety of frequencies. The appropriate frequency can be chosen, for example, to match the frequency of the magnetic field located at the specific spatial location where the specific coil is located. Because the magnetic field can vary as a function of space, as shown in FIG. 6A, the field and frequency of the coil can be adjusted to approximately match the spatial location. Here the coils can be designed to image the field locations B1, B2, and B3, which are physically separated along a single axis.

For this low field system, in accordance with various embodiments, a low-noise preamplifier can be designed and configured to leverage the low signal environment of the MRI system. This low noise amplifier can be configured to utilize components that do not generate significant electronic and voltage noise at the desired frequencies (for example, <3 MHz and >2 MHz). Typical junction field effect transistor designs (J-FET) generally do not have the appropriate noise characteristics at this frequency and can create high frequency instabilities at the GHz range that can bleed into, although several decades of dB lower, into the measured frequency range. Since the gain of the system can preferably be, for example, >80 dB overall, any small instabilities or intrinsic electrical noise can be amplified and degrade signal integrity.

Figure 6B:
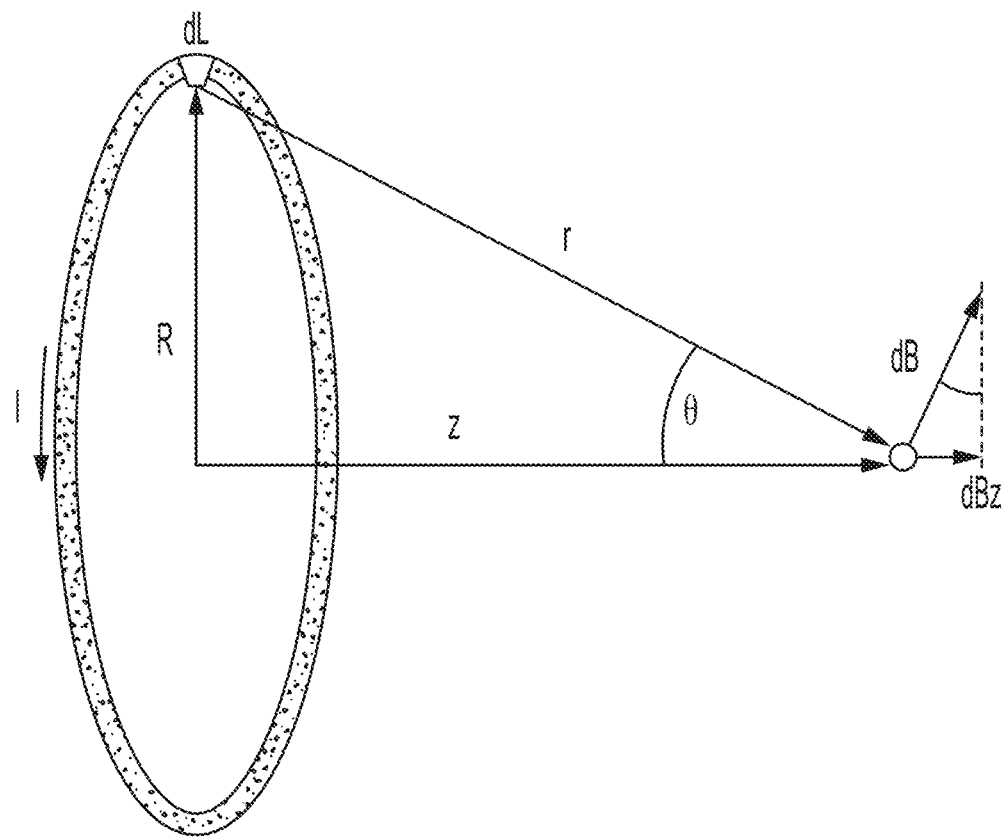
FIG. 6B is an example illustration of a loop coil along with example calculations for a loop coil magnetic field, in accordance with various embodiments.
Figure 6C:
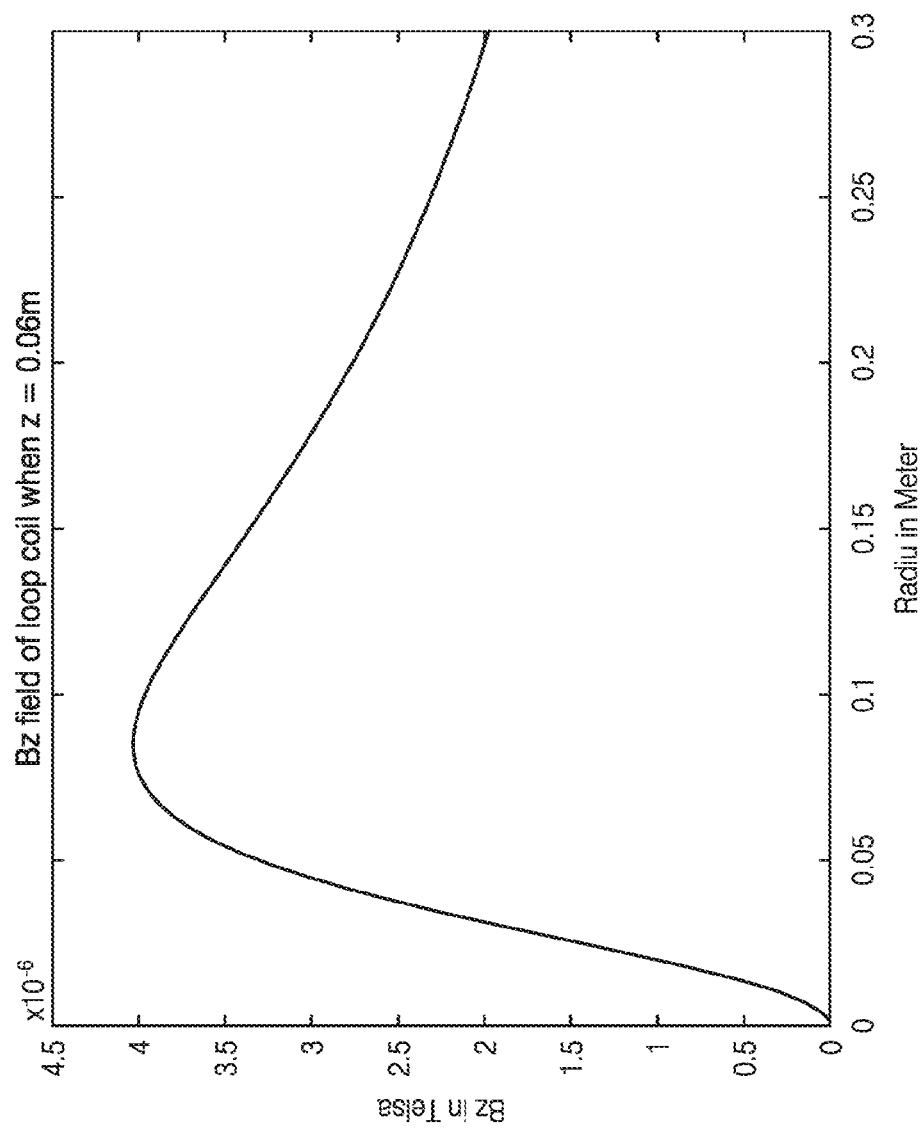
FIG. 6C is an example X-Y chart illustrating the magnetic field as a function of radius of a loop coil, in accordance with various embodiments disclosed herein.
Figure 6D:
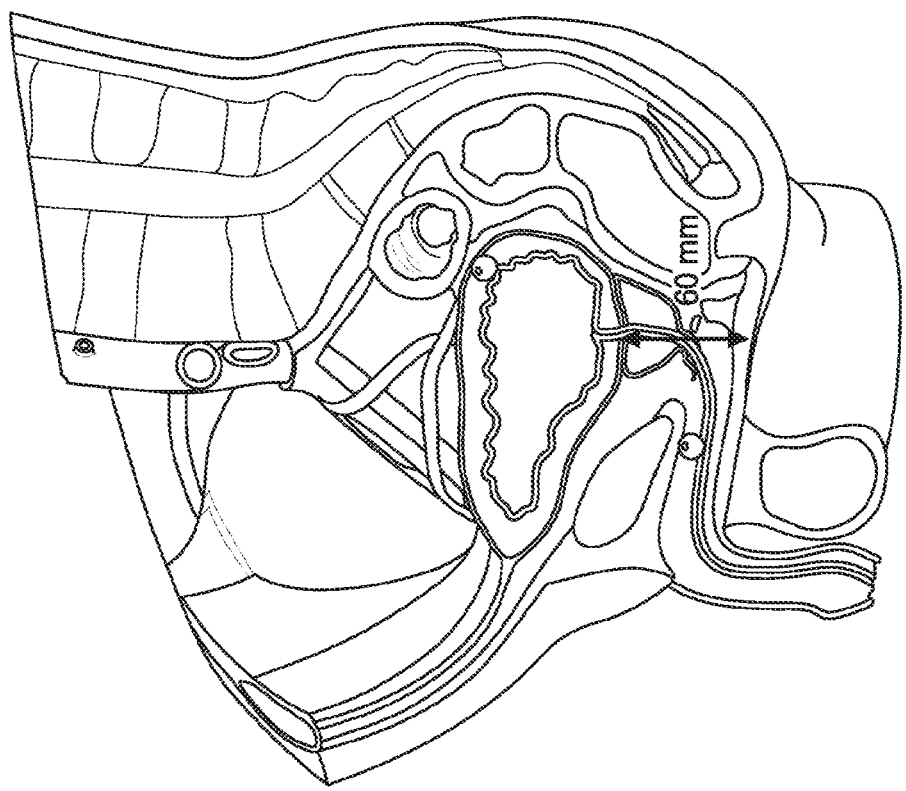
FIG. 6D is a cross-sectional illustration of a portion of the human body, namely in the area of the prostate.

Referring to FIG. 6B, RF-RX coils can be designed to image specific limited field of views based upon the target anatomy. The prostate, for example, is about 60 millimeters deep within the human body (see FIG. 6D), so to design a RX coil for prostate imaging, the coil should be configured to enable imaging 60 mm deep inside human body. According to Biot-Savart law, the magnetic field of a loop coil can be calculated by the following equation, $$Bz = \frac{\mu_0}{4\pi} * \frac{2\pi * R^2 * I}{(z^2 + R^2)^{\frac{3}{2}}}$$

where $\mu_0 = 4\pi*10-7$ H/m is the vacuum permeability, R is the radius of the loop coil, z is distance along the center line of the coil from its center, and I is the current on the coil (see FIG. 6B). Assuming I=1 Ampere, with the goal of locating a figure of magnetic field (Bz) at z=60 mm, the maximum position is when R is 85 mm according to the chart shown in FIG. 6C.

Based upon the geometrical constraints of the body, the loop coil can be set up at the space between the human legs upon the torso. As such, it is extremely difficult, if not impossible, to fit a 170-mm diameter coil there. According to FIG. 6C, the Bz field value is proportional to the radius of the loop when R is less than 85 mm. As such, it is advantageous that the coil be as large as it can be. For example, the largest loop coil that can be placed between people is about 10 mm large.

As the size of the coil is limited by the space between legs, the magnetic field of a 10-mm diameter coil is generally not capable of reaching the depth of prostate. Therefore, single coil may not be enough for prostate imaging thus, in this case, multiple coils could prove beneficial in getting signal from different directions. In various embodiments of the MRI system, the magnetic field is provided in the z-direction and RF coils are sensitive to x- and y-direction. In this example case, a loop coil in x-y plane would not collect RF signal from a human since it is sensitive to z-direction, while a butterfly coil can be used in this case. Then based on the location and orientation, RF coil could be a loop coil or butterfly coil. In addition, a coil can be placed in under the body and there is no limitation for its size.

As for the needs of multiple RX coils, in various embodiments, decoupling between them can prove beneficial for various embodiments of an MRI system RX coil array. In those cases, each coil can be de-coupled with the other coils, and the decoupling techniques can include, for example, 1) geometry decoupling, 2) capacitive/inductive decoupling, and 3) low-/high impedance pre-amplifier coupling.

The MRI system, in accordance with various embodiments, can have a variant magnetic field from the magnet, and its strength can vary linearly along the z direction. The RX coils can be located in different positions in z-direction, and each coil can be tuned to different frequencies, which can depend on the location of the coils in the system.

Based upon the simplicity of single coil loops, these coils can be constructed from simple conductive traces that can be pre-tuned to a desired frequency and printed, for example, on a disposable substrate. This cheaply fabricated technology can allow a clinician to place the RX coil (or coil array) upon the body at the region of interest for a given procedure and dispose of the coil afterwards. For example, and in accordance with various embodiments, the RX coils can be surface coils, which can be affixed to, e.g., worn or taped to, a patient's body. For other body parts, e.g. an ankle or a wrist, the surface coil might be a single-loop configuration, figure-8 configuration, or butterfly coil configuration wrapped around the region of interest. For regions that require significant penetration depth, e.g. the torso or knee, the coil might consist of a Helmholtz coil pair. The main restriction to the receive coil is similar to other MRI systems: the coil must be sensitive to a plane that is orthogonal to the main magnetic field, B0, axis.

In accordance with various embodiments, the coils might be inductively coupled to another loop that is electrically connected to the receive preamplifier. This design would allow for easier and unobstructed access of the receive coils.

In accordance with various embodiments, the size of coils can be limited by the structure of human body. For example, the coils' size should be positioned and configured to fit in the space between human legs when imaging the prostate.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Programmable Logic Controller

As discussed herein, and in accordance with various embodiments, the various systems, and various combinations of features that make up the various system embodiments, can also include a programmable logic controller (PLC). PLCs are industrial digital computers which can be designed to operate reliably in harsh usage environments and conditions. PLCs can be designed to handle these types of conditions and environments, not just in the external housing, but in the internal components and cooling arrangements as well. As such, PLCs can be adapted for the control of manufacturing processes, such as assembly lines, or robotic devices, or any activity that requires high reliability control and ease of programming and process fault diagnosis.

In accordance with various embodiments, the system can contain a PLC that can control the system in pseudo real-time. This controller can manage the power cycling and enabling of the gradient amplifier system, the radio frequency transmission (transmit) system, the frequency tuning system, and sends a keep alive signal (e.g., a message sent by one device to another to check that the link between the two is operating, or to prevent the link from being broken) to the system watchdog. The system watchdog can continually look for a strobe signal supplied by the computer system. If the computer threads stall, a strobe is missed that can trigger the watchdog to enter a fault condition. If the watchdog enters a fault condition, the watchdog can operated to depower the system.

The PLC can generally handle low level logic functions on incoming and outgoing signals into system. This system can monitor the subsystem health and control when subsystems needed to be powered or enabled. The PLC can be designed in different ways. One design example includes a PLC with one main motherboard with four expansion boards. Due to the speed of the microcontroller on the PLC, subsystems can be managed in pseudo real-time, while real-time applications can be handled by the computer or spectrometer on the system.

The PLC can serve many functional responsibilities including, for example, powering on/off the gradient amplifiers (discussed in greater detail herein) and the RF amplifier (discussed in greater detail herein), enabling/disabling the gradient amplifiers and the RF amplifier, setting the digital and analog voltages for the RF coil tuning, and strobing the system watchdog.

As discussed above, it should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Robot

As discussed herein, and in accordance with various embodiments, the various systems, and various combinations of features that make up the various system embodiments, can also include a robot.

In some medical procedures, such as a prostate biopsy, it is typical for the patient to endure a lengthy procedure in an uncomfortable prone position, which often includes remaining motionless in one specific body position during the entire procedure. In such long procedures, if a metallic ferromagnetic needle is used for the biopsy with guidance from an MRI system, the needle may experience attraction force from the strong magnets of the MRI system, and thus may cause it to deviate from its path during the length of the procedure. Even in the case of using a non-magnetic needle, the local field distortions can cause distortions in the magnetic resonance images, and therefore, the image quality surrounding the needle may result in a poor quality. To avoid such distortions, pneumatic robots with complex compressed air mechanism have been designed to work in conjunction with conventional MRI systems. Even then, access to target anatomy remains challenging due to the form factor of currently available MRI systems.

The various embodiments presented herein include improved MRI systems that are configured to use for guiding in medical procedures, including, for example, robot-assisted, invasive medical procedures. The technologies, methods and apparatuses disclosed herein relate to a guided robotic system using magnetic resonance imaging as a guidance to automatically guide a robot (generally referred to herein as "a robotic system") in medical procedures. In accordance with various embodiments, the disclosed technologies combine a robotic system with magnetic resonance imaging as guidance. In accordance with various embodiments, the robotic system disclosed herein is combined with other suitable imaging techniques, for example, ultrasound, x-ray, laser, or any other suitable diagnostic or imaging methodologies.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Spectrometer

As discussed herein, and in accordance with various embodiments, the various systems, and various combinations of features that make up the various system embodiments, can also include a spectrometer.

A spectrometer can operate to control all real-time signaling used to generate images. It creates the RF transmit (RF-TX) waveform, gradient waveforms, frequency tuning trigger waveform, and blanking bit waveforms. These waveforms are then synchronized with the RF receiver (RF-RX) signals. This system can generate frequency swept RF-TX pulses and phase cycled RF-TX pulses. The swept RF-TX pulses allow for an inhomogeneous B1+ field (RF-TX field) to excite a sample volume more effectively and efficiently. It can also digitize multiple RF-RX channels with the current configuration set to four receiver channels. However, this system architecture allows for an easy system scale-up to increase the number of transmit and receive channels to a maximum of 32 transmit channels and 16 receive channels without having to change the underlying hardware or software architecture.

The spectrometer can serve many functional responsibilities including, for example, generating and synchronizing the RF-TX (discussed in greater detail herein) waveforms, X-gradient waveforms, Y-gradient waveforms, blanking bit waveforms, frequency tuning trigger waveform and RF-RX windows, and digitizing and signal processing the RF-RX data using, for example, quadrature demodulation followed by a finite impulse response filter decimation such as, for example, a cascade integrating comb (CIC) filter decimation.

The spectrometer can be designed in different ways. One design example includes a spectrometer with three main components: 1) a first software design radio (SDR 1) operating with Basic RF-TX daughter cards and Basic RF-RX daughter cards; 2) a second software design radio (SDR 2) operating with LFRF TX daughter cards and Basic RF-RX daughter cards; and 3) a clock distribution module (octoclock) that can synchronize the two devices.

SDRs are the real-time communication device between the transmitted signals and received MRI signals. They can communicate over 10 Gbit optical fiber to the computer using a Small Form-factor Pluggable Plus transceiver (SFP+) communication protocol. This communication speed can allows the waveforms to be generated with high fidelity and high reliability.

Each SDR can include a motherboard with an integrated field-programmable gate array (FPGA), digital to analog converters, analog to digital converters, and four module slots for integrating different daughtercards. Each of these daughtercards can function to change the frequency response of the associated TX or RX channel. In accordance with various embodiments, the system can utilizes many variations daughtercards including, for example, a Basic RF version, and a low frequency (LF) RF version. The Basic RF daughtercards can be used for generating and measuring RF signals. The LF RF version can be used for generating gradient, trigger and blanking bit signals.

The octoclock can be used to synchronize a multi-channel SDR system to a common timing source while providing high-accuracy time and frequency reference distribution. It can do so, for example, with 8-way time and frequency distribution (1 PPS and 10 MHz). An example of an octoclock is the Ettus Octoclock CDA, which can distribute a common clock to up to eight SDRs to ensure phase coherency between the two or more SDR sources.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

RF AMP/Gradient AMP

As discussed herein, and in accordance with various embodiments, the various systems, and various combinations of features that make up the various system embodiments, can also include a radio frequency amplifier (RF amplifier) and a gradient amplifier.

A RF amplifier is a type of electronic amplifier that can converts a low-power radio-frequency signal into a higher power signal. In operation, the RF amplifier can accept signals at low amplitudes and provide, for example, up to 60 dB of gain with a flat frequency response. This amplifier can accept three phase AC input voltage and can have a 10% max duty cycle. The amplifier can be gated by a 5V digital signal so that unwanted noise is not generated when the MRI is receiving signal.

In operation, a gradient amplifier can increase the energy of the signal before it reaches the gradient coils such that the field strength can be intense enough to produce the variations in the main magnetic field for localization of the later received signal. The gradient amplifier can have two active amplification channels that can be controlled independently. Each channel can send out current to either the X or Y channel respectively. The third axis of spatial encoding is generally handled by a permanent gradient in the main magnetic field (B0). With varying combinations of pulse sequences, the signal can be localized in three dimensions and reconstructed to create an object.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Display/GUI

As discussed herein, and in accordance with various embodiments, the various systems, and various combinations of features that make up the various system embodiments, can also include a display in the form of, for example, a graphical user interface (GUI). In accordance with various embodiments, the GUI can take any contemplated form necessary to convey the information necessary to run magnetic resonance imaging procedures.

Further, it should be appreciated that the display may be embodied in any of a number of other forms, such as, for example, a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose display device as may be desirable or appropriate for a given application or environment.

The GUI is a system of interactive visual components for computer software. A GUI can display objects that convey information, and represent actions that can be taken by the user. The objects change color, size, or visibility when the user interacts with them. GUI objects include, for example, icons, cursors, and buttons. These graphical elements are sometimes enhanced with sounds, or visual effects like transparency and drop shadows.

A user can interact with a GUI using an input device, which can include, for example, alphanumeric and other keys, mouse, a trackball or cursor direction keys for communicating direction information and command selections to a processor and for controlling cursor movement on the display. An input device may also be the display configured with touchscreen input capabilities. This input device typically has two degrees of freedom in two axes, a first axis (i.e., x) and a second axis (i.e., y), that allows the device to specify positions in a plane. However, it should be understood that input devices allowing for 3 dimensional (x, y and z) cursor movement are also contemplated herein.

In accordance with various embodiments, the touchscreen, or touchscreen monitor, can serves as the primary human interface device that allows a user to interact with the MRI. The screen can have a projected capacitive touch sensitive display with an interactive virtual keyboard. The touchscreen can have several functions including, for example, displaying the graphical user interface (GUI) to the user, relaying user input to the system's computer, and starting or stopping a scan.

In accordance with various embodiments, GUI views can be typically screens displayed (Qt widgets) to the user with appropriate buttons, edit fields, labels, images, etc. These screens can be constructed using a designer tool such as, for example, the Qt designer tool, to control placement of widgets, their alignment, fonts, colors, etc. A user interface (UI) sub controller can possess modules configured to control the behavior (display and responses) of the respective view modules.

Several application utilities (App Util) modules can performs specific functions. For example, S3 modules can handle data communication between the system and, for example, Amazon Web Services (AWS). Event Filters can be present to ensure valid characters are displayed on screen when user inputs are required. Dialog messages can be used to show various status, progress messages or require user prompts. Moreover, a system controller module can be utilized to handle coordination between the sub controller modules, and key data processing blocks in the system, the pulse sequence generator, pulse interpreter, spectrometer and reconstruction.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Processing Module

As discussed herein, and in accordance with various embodiments, the various workflows or methods, and various combinations of steps that make up the various workflow or method embodiments, can also include a processing module.

In accordance with various embodiments, a processing module serves many functions. For example, a processing module can generally operate to receive signal data acquired during the scan, process the data, and reconstruct those signals to produce an image that can be viewed (for example, via a touchscreen monitor that displays a GUI to the user), analyzed and annotated by system users. Generally, to create an image, an NMR signal must be localized in three-dimensional space. Magnetic gradient coils localize the signal and are operated before or during the RF acquisition. By prescribing a RF and gradient coil application sequence, called a pulse sequence, the signals acquired correspond to a specific magnetic field and RF field arrangement. Using mathematical operators and image reconstruction techniques, arrays of these acquired signals can be reconstructed into an image. Usually these images are generated from simple linear combinations of magnetic field gradients. In accordance with various embodiments, the system can operate to reconstruct the acquired signals from a-priori knowledge of, for example, the gradient fields, RF fields, and pulse sequences.

In accordance with various embodiments, the processing module can also operate to compensate for patient motion during a scan procedure. Motion (e.g., beating heart, breathing lungs, bulk patient movement) is one of the most common sources of artifacts in MRI, with such artifacts affecting image quality by leading to misinterpretations in the images and a subsequent loss in diagnostic quality. Therefore, motion compensation protocols can help address these issues at minimal cost in time, spatial resolution, temporal resolution, and signal-to-noise ratio.

In accordance with various embodiments, the processing module might include artificial intelligence machine learning modules designed to denoise the signal and improve the image signal-to-noise ratio.

In accordance with various embodiments, the processing module can also operate to assist clinicians in planning a path for subsequent patient intervention procedures, such as biopsy. In accordance with various embodiments, a robot can be provided as part of the system to perform the intervention procedure. The processing module can communicate instructions to the robot, based on image analysis, to properly access, for example, the appropriate region of the body requiring a biopsy.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described below. It should further be noted that exemplary description of specific features are used, largely for informational purposes, and not in any way to limit the design, subfeature, and functionality of the specifically described feature.

Chirped Magnetic Resonance Imaging Module

For wide bandwidth pulses, two recognized ways to increase the bandwidth of a radio frequency (RF) pulse beyond the limits of the Fourier relationship between its length and bandwidth are composite pulses and adiabatic pulses. Adiabatic pulses, in particular, can be used in imaging with the typical goals of compensating for RF field imperfections and compensating for permanent magnetic field gradients. An example of a relevant adiabatic pulse is a chirp pulse. Known uses of the chirp pulse serve to encode spatial information using the permanent gradient as well as a pulsed electromagnetic gradient.

The disclosed systems and methods in accordance with various embodiments as described herein relate to improved approaches to collect NMR spectra and MR images in inhomogeneous fields using wide bandwidth pulses, via an RF chirp pulse.

For multi-slice excitation methods for imaging inhomogeneous fields, if the bandwidth of an RF pulse cannot be increased or should not be increased (e.g., via wide band pulses), methods exists for collecting information from the entire imaging volume. A relevant way is to tune the resonance frequency of the RF coil to a different frequency when a user wants to measure a different part of space. This allows one to sample the entire imaging field of view even if the bandwidth of the RF pulses are narrower than the frequency range of the entire field of view. As a result, of this multi-slice excitation method, one can image a three-dimensional (3D) volume by exciting multiple slices along one axis and then phase encode along the other two axes. Using readout pulses in a system with a strong permanent gradient is inadvisable because the axis of the readout will be tilted by the permanent gradient. The problem with such techniques is that each slice must be measured one at a time and the thinness of each slice results in the ignoring of the slice selection axis, thus resulting in the projection of a 3D voxel onto a 2D plane, with the axes of the 2D plane being phase encoded. Therefore, having to phase encode both axes while also collecting each slice one by one severely slows the rate of image acquisition.

The disclosed systems and methods in accordance with various embodiments as described herein relate to improved approaches to collect NMR spectra and MR images in inhomogeneous fields using multi-slice excitation methods with a faster rate of image acquisition than currently exists in the art.

In accordance with various embodiments, inhomogeneity can be considered the degree of lack of homogeneity, for example the fractional deviation of the local magnetic field from the average value of the field.

In accordance with various embodiments, a pulse sequence diagram illustrates the steps of basic hardware activity that are incorporated into a pulse sequence using multiple lines, each representing a different component. For example, the radio frequency transmitter component can be represented on the top line of a pulse sequence diagram, slice selection gradient on the second line, phase encoding gradient on the third line, and frequency encoding gradient/readout gradient on the fourth or bottom line.

Figure 7A:
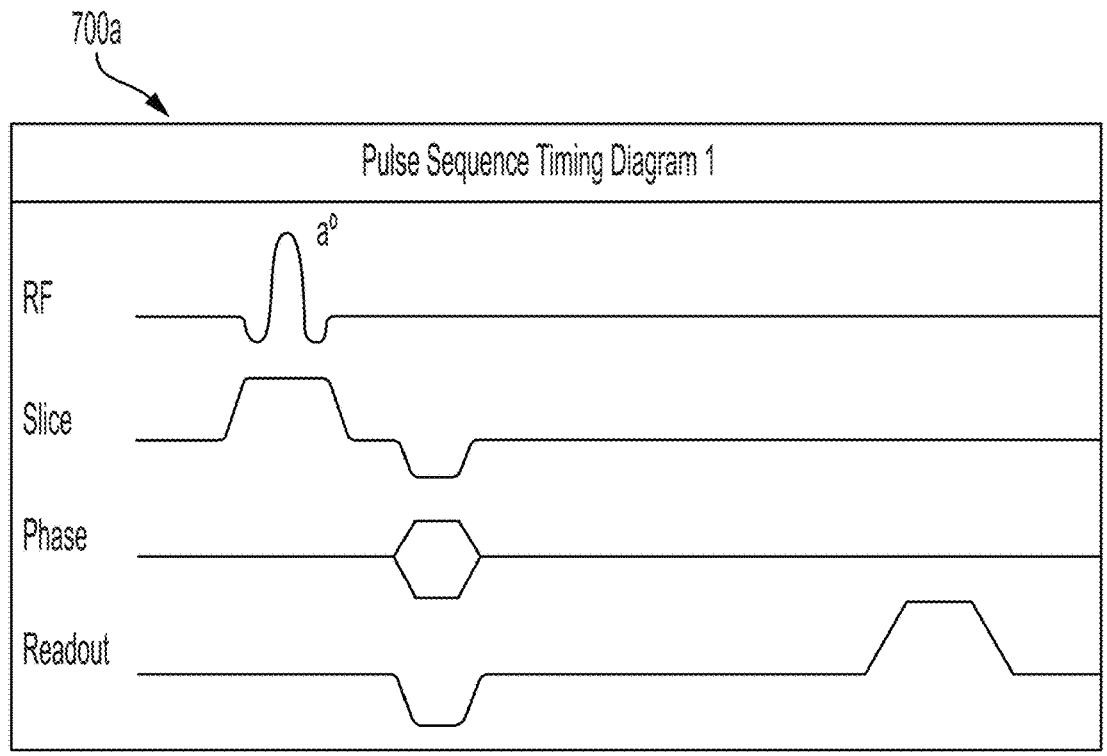
FIG. 7A is an example schematic pulse sequence diagram for a two-dimensional pulse sequence, in accordance with various embodiments.

FIG. 7A is an example schematic pulse sequence diagram 700a for a two-dimensional (2D) pulse sequence, in accordance with various embodiments. For pulse sequence diagrams of a 2D-pulse sequence, as shown in FIG. 7A, slice selection and signal detection are repeated in duration, relative timing and amplitude, each time the sequence is repeated. Durations of the slice selection pulses may range from 70 microseconds to 10 milliseconds while the amplitude of the slice selection pulses may be modified to reach flip angles 1 to 180 degrees. The duration of the acquisition window will vary depending on the strength of the readout gradient applied during it. Acquisition durations may range from 10 microseconds to 10 milliseconds, with the number of points acquired during this time ranging from 16 to 512. For each executed sequence, a single-phase encoding component is present. A deviation above or below the horizontal line generally indicates a gradient pulse. Pulse diagrams can indicate simultaneous component activities such as the RF pulse and slice selection gradient as non-zero deviations from both lines at the same horizontal position. Simple deviations from zero show constant amplitude gradient pulse. Gradient amplitudes that change during the measurement, e.g. phase encoding are represented on the diagram.

Figure 7B:
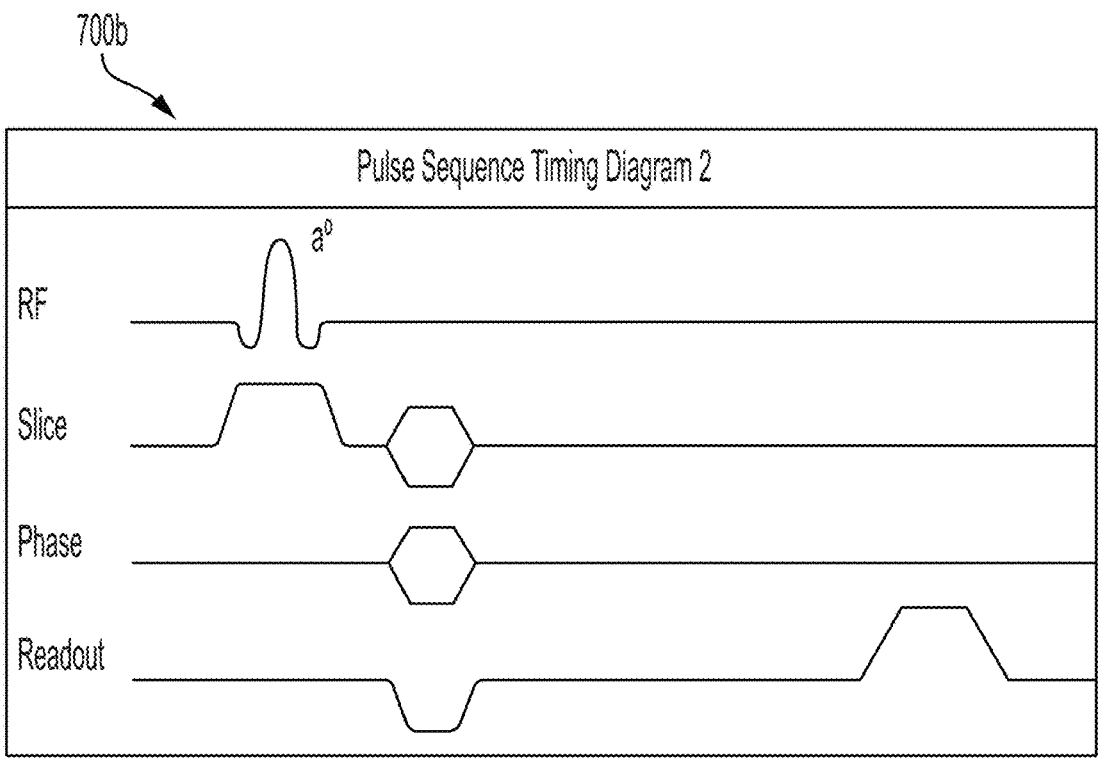
FIG. 7B is an example schematic pulse sequence diagram for a three-dimensional pulse sequence, in accordance with various embodiments.

FIG. 7B is an example schematic pulse sequence diagram 700b for a three-dimensional pulse sequence, in accordance with various embodiments. As illustrated in FIG. 7B, a 3D-pulse sequence 700b shown includes volume excitation and signal detection that are repeated in duration, relative timing and amplitude, each time the sequence is repeated. In the case of a 3D-pulse sequence, two-phase encoding components are present, one in the phase encoding direction and the other in slice selection direction (irrespectively incremented in amplitude) in each time the sequence is executed.

It is well known that inhomogeneities of the static magnetic field, e.g., permanent gradient field, which is also referred to herein as inhomogeneous permanent gradient field, produced by the scanner as well as by object susceptibility, is difficult to avoid in magnetic resonance imaging (MRI). Typically, the inhomogeneity of the field is a nuisance to be avoided and rarely is the inhomogeneous field a source of spatial information. The large value of gyromagnetic coefficient can cause a significant frequency shift in field inhomogeneity of even a few parts per million, which in turn causes distortions in both geometry and intensity of the magnetic resonance (MR) images. Manufacturers will always strive to homogenize the magnetic field as much as possible, especially at the core of the scanner. Even with an ideal magnet, inhomogeneity remains to some degree, which can also be caused by the susceptibility of the imaging object. The geometrical distortion (displacement of the pixel locations) is important e.g., for some cases as stereotactic surgery. The second problem is the undesired changes in the intensity or brightness of pixels, which may cause problems in determining different tissues and reduce the maximum achievable image resolution.

Relevant methods for imaging in inhomogeneous fields include use of wide bandwidth pulses and multi-slice excitation. Both however deal with the challenge of imaging in an inhomogeneous permanent field. Wide bandwidth pulses, for example, affect a wide range of frequencies. Bandwidths of the wide bandwidth pulses may range from about 1 kHz to about 1 MHz. In accordance with various embodiments, the bandwidth may range from 1 kHz to 10 kHz, 10 kHz to 40 kHz, 40 kHz to 100 kHz, 100 kHz to 400 kHz, and 400 kHz to 1 MHz, or any ranges of bandwidth thereof. Examples of RF pulses that can have such bandwidths include chirped pulses, adiabatic half passage pulses and composite hard pulses. If a field is inhomogeneous, then increasing the bandwidth of a pulse means that the RF pulse may affect more of a sample. There are many ways to increase the bandwidth of an RF pulse beyond the limits of the Fourier relationship between its length and bandwidth. Two notable ways are composite pulses and adiabatic pulses.

Composite pulses are conventional RF pulses appended to one another in an order, often with phase shifts between the appended pulses. By combining RF pulses in this way, it is possible to compensate for their imperfections. Doing so also makes the bandwidth of the composite pulse greater than the bandwidth of the pulses used to make it. This makes composite pulses ideal for use in inhomogeneous magnetic fields.

Adiabatic pulses excite, invert or refocus magnetization by a different means than conventional RF pulses. Instead of abruptly changing the effective magnetic field experienced by the magnetization, adiabatic pulses instead change the effective field gradually, dragging the magnetization along with the field as it changes. The effective field is changed by altering the frequency of the RF pulse. The duration of these pulses can range from 100 microseconds to 20 milliseconds. The magnetization will tend to be aligned with the direction of the effective field, until the RF pulse is on resonance with the magnetization, where the adiabatic condition will be violated, allowing for adiabatic excitation. In the case of adiabatic inversion, the magnetization will always follow the direction of the effective field. This allows for RF pulses with much wider bandwidths than conventional RF pulses, among other advantages. One can implement adiabatic pulses in oil well logging to excite a wide bandwidth, since oil well logging can occur in inhomogeneous fields. One can also implement adiabatic pulses in imaging, usually to compensate for RF field imperfections but also to compensate for permanent magnetic field gradients.

One example of use of an adiabatic pulse to compensate for a permanent gradient is multi-scan extension of cross-term spatiotemporal encoding (xSPEN), a pulse sequence using a type of adiabatic pulse referred to as a chirp pulse. The chirp pulse is one where different wavelengths or colors are not distributed uniformly over the temporal envelope of the pulse. As a result, this pulse affects different parts of space at different times, creating signals that refocus at different points along the acquisition. Exploiting these characteristics of a chirp pulse can allow for the encoding of spatial information using the permanent gradient and a pulsed gradient.

For multi-slice excitation methods for imaging inhomogeneous fields, if the bandwidth of an RF pulse cannot be increased or should not be increased (e.g., via wide band pulses), methods exists for collecting information from the entire imaging volume. A relevant way is to tune the resonance frequency of the RF coil to a different frequency when a user wants to measure a different part of space. This allows one to sample the entire imaging field of view even if the bandwidth of the RF pulses are narrower than the frequency range of the entire field of view. As a result of this multi-slice excitation method, one can image a 3D volume by exciting multiple slices along one axis and then phase encoding along the other two axes, which is necessary to phase encode along both axes due to the strong gradient present in the magnetic field generally produced by such multi-slice excitation methods. Phase encoding along two axes is done by applying a magnetic field gradient along two orthogonal axes when not acquiring signal. By arraying the gradient strength or duration during this phase encoding step, it is possible to encode images along two additional dimensions, with the third being encoded during the signal acquisition step. The problem with such techniques is that each slice must be measured one at a time and the thinness of each slice results in the ignoring of the slice selection axis, thus resulting in the projection of a 3D voxel onto a 2D plane, with the axes of the 2D plane being phase encoded. Therefore, having to phase encode both axes while also collecting each slice one by one severely slows the rate of image acquisition.

In accordance with various embodiments, the technologies described herein are directed to collect NMR spectra and MR images in inhomogeneous fields using multi-slice excitation methods with a faster rate of image acquisition than currently exists in the art. Therefore, Applicant has recognized that solutions are lacking for implementing wide bandwidth pulses (e.g., adiabatic pulses) via chirp pulses for scanner types that seek to avoid utilizing a pulse gradient to encode the requisite spatial information. Applicant has further recognized that solutions are lacking for implementing multi-slice excitation methods in scanners that result in a faster rate of image acquisition than currently exists in the art.

If the permanent gradient in a single sided MRI can be made linear or at least bijective (e.g., one-to-one correspondence between data sets), then the information from that gradient can be used to encode spatial information. To use the permanent gradient as an encoding gradient, a spin echo must be acquired in the field produced by that gradient. A Fourier transform or nonlinear reconstruction of the time domain data of this spin echo can then be used to generate a 1 dimensional profile of the object or patient along the direction of the gradient of the permanent field. For this to be useful, a significant fraction of the magnetization within that gradient must be accessible to RF pulses.

In accordance with various embodiments, a scanner is provided that has a permanent gradient, specially optimized using small magnet elements arranged in a pattern to create a weak enough gradient to allow for a wide RF bandwidth excitation up to about 200 kHz but strong enough for spatial encoding in the permanent magnet direction. The scanner can also have an RF coil that has multiple legs to increase overall field strength that allows for strong and uniform excitation of a wide range of bandwidth with adiabatic pulses. This allows Promaxo to use a unique MRI pulse sequence for 3D encoding.

The basis of the pulse sequence used, in accordance with various embodiments herein, is that the slice select gradient, which is permanent, is also used as a readout gradient. In other words, the information about the slice axis is not projected onto a 2D plane. This is advantageous particularly for scanners that use permanent gradients primarily, as using pulsed readout gradients will likely distort the image. The axes besides the slice select axis must be phase encoded for good image fidelity.

There are many ways to implement the pulse sequence in accordance with various embodiments herein. These include the use of a wide bandwidth pulse, via an adiabatic pulse such as, for example, a chirped pulse for excitation and refocusing. Chirped pulses, for example, can be used for increasing the bandwidth. By using, for example, a chirp pulse, a wide bandwidth can be excited and the frequencies within that bandwidth can contain spatial information along one axis.

Figure 8:
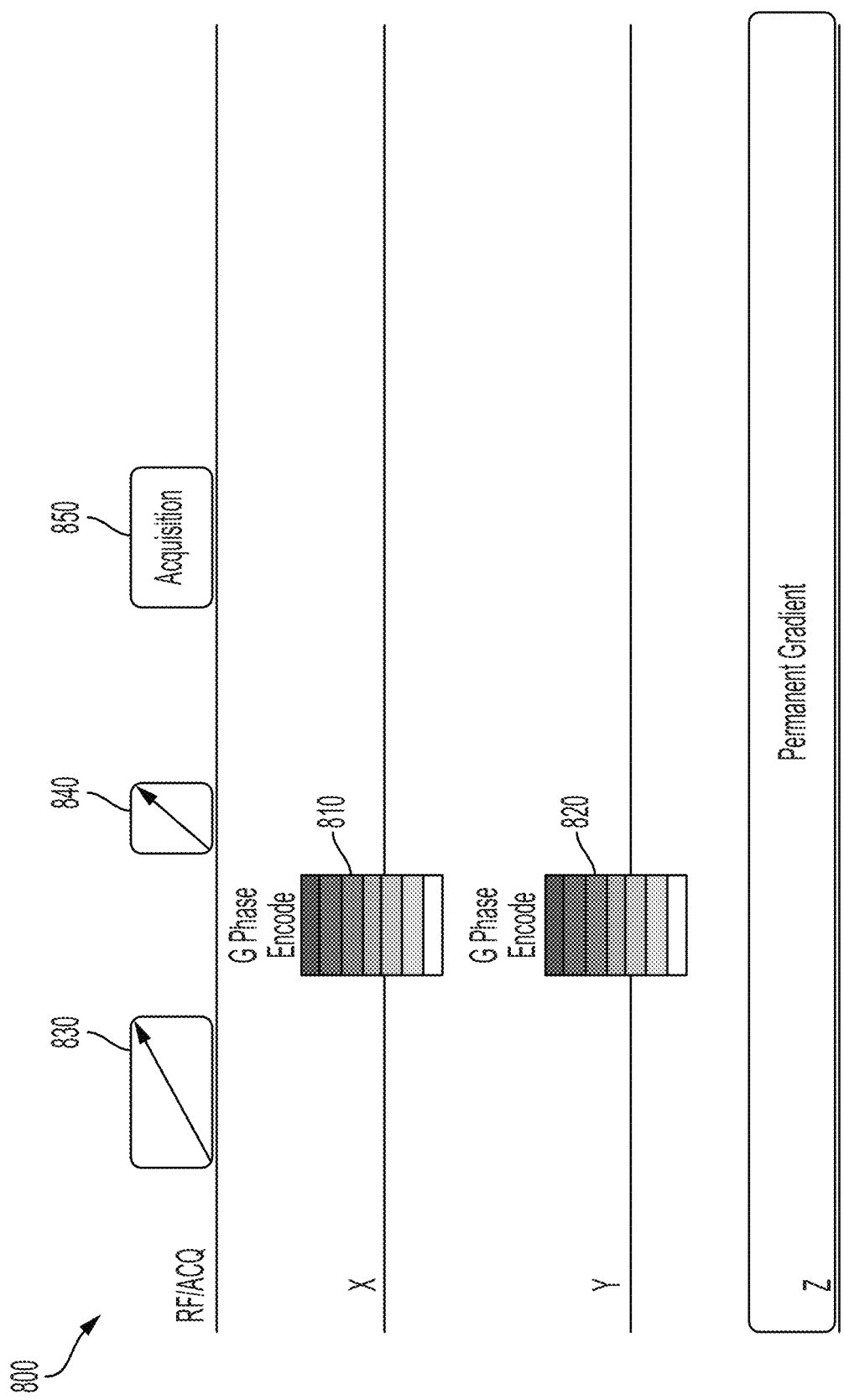
FIG. 8 is a schematic pulse sequence diagram for a system with chirped pulses and a permanent slice selection gradient, in accordance with various embodiments.

FIG. 8 is a schematic pulse sequence diagram 800 for a system with chirped pulses and a permanent slice selection gradient, in accordance with various embodiments. As illustrated in FIG. 8, an approach for using wide band pulses (e.g., chirped pulses) for collecting magnetic resonance images or spectra using a single sided MRI is provided, in accordance with various embodiments. For example, if a permanent magnetic gradient field, such as an inhomogeneous magnetic field is along an axis in the z direction, two phase encodes 810 and 820 can be used in the x and y-axes, as shown in the pulse diagram 800. In the example illustrated in FIG. 8, a single echo can be used. Additionally, the pulse diagram 800 includes two chirped pulses 830 and 840 that can be used and calibrated such that all magnetization refocuses at the same moment, e.g., at the precise time period, during an acquisition 850. As such, the second pulse 840 can be half the length of the first pulse 830 as illustrated in pulse diagram 800, if both pulses have the same or substantially similar bandwidth, in accordance with various embodiments.

The bandwidth of these pulses may range from 1 kHz to 10 kHz, 10 kHz to 40 kHz, 40 kHz to 100 kHz, 100 kHz to 400 kHz, and 400 kHz to 1 MHz, or any ranges of bandwidth thereof. The magnetization affected by the chirped pulse can be, for example, phase encoded along two orthogonal axes or along just one axis for 2D images. In various embodiments, the entire imaging volume is encoded at once. In various embodiments, portions of the imaging volume are encoded one at a time. The signal that this produces is encoded along z for the readout and x and y for phase encodes. Doing so allows one to image an entire volume more quickly. The slice thickness of the volume can be increased with post processing to increase the signal to noise ratio.

Therefore, in view of the above, Applicant has discovered a way to collect NMR spectra and MR images in inhomogeneous fields using a specific wide-band pulse (e.g., chirp pulse) in combination with multi-slice excitation methods in specific MRI scanners (e.g., single-sided MRIs) with a faster rate of image acquisition without the need for a pulsed gradient. This method allows for imaging an entire volume much more quickly than would otherwise be possible with a multi-slice acquisition. In addition, by using the slice select gradient as a readout, no information along the z-axis is lost. In view of the technologies disclosed in accordance with various embodiments, the disclosed implementation methods overcome existing challenges in combining the two methods. For example, some of the overcome challenges may include difficulty in implementing chirp pulses for imaging while compensating for their unusual behavior, designing a permanent field that is useful for imaging, interleaving the data slices excited by the chirp pulse for efficient signal averaging, and/or collapsing 3 dimensional data into a series of 2 dimensional slices efficiently when the third dimension is directly measured.

The speedup can be best appreciated by calculating how many slices are needed to image a normal field of view. For example, in accordance with various embodiments, the field of view (also referred to herein as region of interest) in the scanner discussed herein is a 4 to 12 inch diameter sphere. The example scanner can be capable of producing conventional slice selection pulses with a thickness ranging from 0.5 to 5 mm, which means that, for example, approximately 34 slices would be selected to cover the entire field of view. The same scanner is also able to produce chirped pulses that excite slices with thickness of one inch, meaning that only four slices are needed to cover the whole field of view, provided that the slice direction is treated as a readout as well. That would be a speedup of approximately 8.5, with possible limitations on speedup primarily due to the hardware of the scanner. With wide bandwidth receive and transmit coils, equal to the bandwidth of the field of view, it is possible to select the entire imaging volume with one slice.

Figure 9:
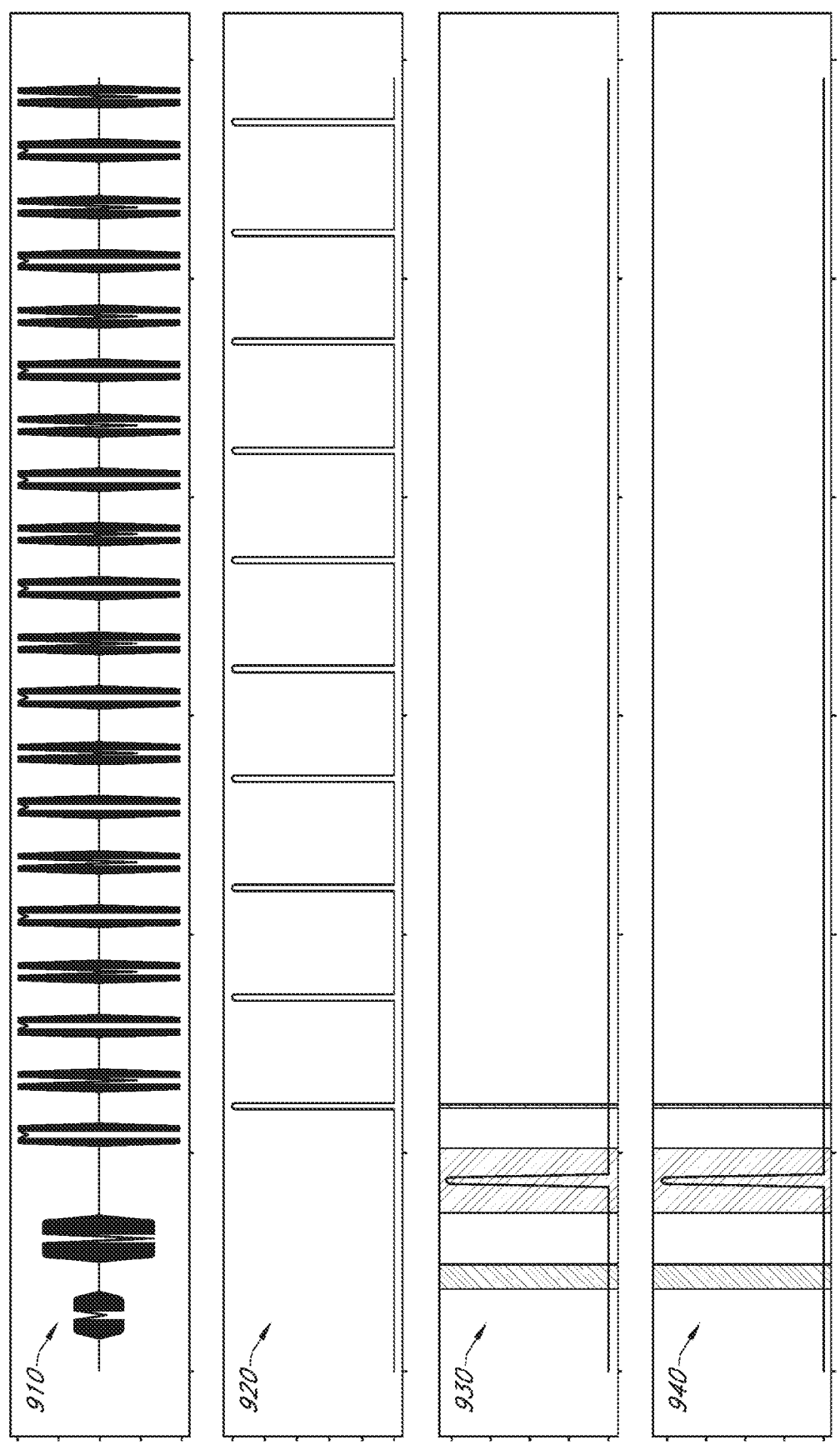
FIG. 9 illustrates example pulse sequences, in accordance with various embodiments.

FIG. 9 illustrates example pulse sequences, in accordance with various embodiments. As illustrated in FIG. 9, some example of the digital waveforms generated by a system computer and sent to the software design radio (SDR). A signal sequence 910 shown in the top channel is the radio frequency transmit (RFTx) channel, which has all the waveforms sent to a transmit system (TX) segment of the RF system. In this example, all pulses in the RFTx channel are chirped pulses, with identical bandwidths, but differing durations. In accordance with various embodiments, the pulses generated are not mixed with a carrier wave in this iteration, meaning that their center frequency is 0 Hz. Once generated, the pulses are mixed with a carrier wave in the SDR, changing their center frequency to the frequency needed to meet the Larmor frequency of the system, in accordance with various embodiments.

As illustrated in FIG. 9, a signal sequence 920 is the radio frequency receive (RFRx) channel. Unlike the RFTx channel, this channel is not converted into an analog signal. Instead, this channel is a series of instructions for the SDR for when to digitize the analog signal it is receiving from the receive system (RX) section of the RF system. In accordance with various embodiments, the SDR is always receiving some signal from the RX section, but only the signal collected when the RFRx channel is set to 1 is relevant for imaging.

Further illustrated in FIG. 9, signal sequences 930 and 940 shown in the bottom two channels are the gradient channels. In accordance with various embodiments, these signal sequences 930 and 940 correspond to the waveforms that are sent to the gradient coils, after being amplified by a gradient amplifier. The gradients are responsible for encoding spatial information in the signal collected, in accordance with various embodiments.

Figure 10:
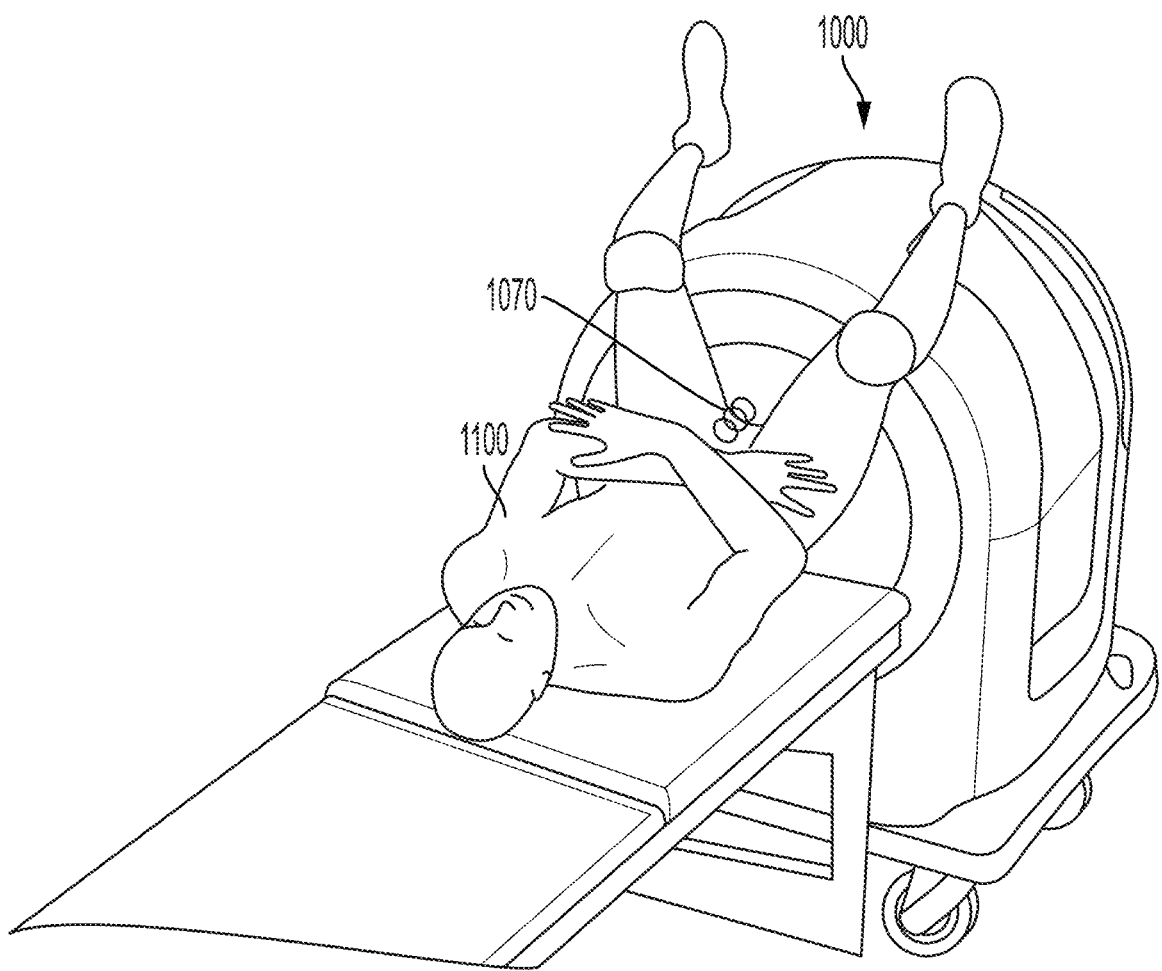
FIG. 10 illustrates an example position of patient for imaging in a magnetic resonance imaging system, according to various embodiments.

FIG. 10 illustrates an example position of patient for imaging in a magnetic resonance imaging system 1000, according to various embodiments. As illustrated in FIG. 10, the receive (Rx) coil 1070 can be placed on a patient 1100. In accordance with various embodiments, the receive coil 1070 can be one of a single-loop coil configuration, figure-8 coil configuration, or butterfly coil configuration. As illustrated in FIG. 10, the receive coil 1070 is a 3-loop coil that is placed on an anatomical portion of the patient 1100. In accordance with various embodiments, the signal acquired by the receive coil 1070 can be sent to the RX section of the RF system.

In accordance with various embodiments, a method for performing a chirped MRI scan includes the following steps. In a first step, the patient is positioned so that the relevant part of their body is placed in the field of view. Then, a receive coil or coil array is placed on the patient. Different parts of the body can require different receive coil arrays. In accordance with various embodiments, the design of these arrays varies. In accordance with various embodiments, some designs have all coils with the same tune, which is changed with the tuning box. In accordance with various embodiments, others have an array of coils where each has a separate, static tune. Regardless of the design, the receive coils are placed so that their spatial sensitivity overlaps with the frequencies that they are sensitive to. Once the patient and the receive coils are positioned, a signal is acquired to confirm their placement. Signal is acquired by sending out two pulses from the SDR to the TX section of the RF system. These two pulses are both chirped pulses, designed to induce a signal in the patient which will be picked up by the receive coils on their body. These signals are then sent from the receive coils to the RX section of the RF system. If a signal is detected, the scan proceeds to its next step. In the next phase, an image is taken of the patient to confirm that they have been placed in the correct position. To collect an image, a sequence of chirped pulses are applied to the patient. These pulses are sent through the TX section of the RF system. In between applications of these chirped pulses, signal is acquired from the receive coils, through the RX section of the RF system. Also, gradient pulses are sent to the system to encode spatial information to the signal. Once the position of the patient is confirmed, a full image is taken. The full image is collected in a manner similar to the image used to confirm the position of the patient. The only difference is that the full image will be higher resolution and so will take longer to acquire.

In accordance with various embodiments, a magnetic resonance imaging system is provided. In accordance with various embodiments, the system includes a radio frequency receive system comprising a radio frequency receive coil configured to be placed proximate a target subject. In accordance with various embodiments, the receive system is configured to deliver a signal of a target subject for forming a magnetic resonance image of the target subject, wherein the signal comprises at least two chirped pulses. In accordance with various embodiments, the system includes a housing, wherein the housing comprises a permanent magnet for providing an inhomogeneous permanent gradient field. In accordance with various embodiments, the imaging system is configured to apply a multi-slice excitation along the inhomogeneous permanent gradient field, a radio frequency transmit system configured to deliver a sequence of chirped pulses, and a single-sided gradient coil set configured to deliver a plurality of gradient pulses orthogonal to the inhomogeneous permanent gradient field.

In accordance with various embodiments, the system further includes a power source, wherein the power source is configured to flow current through at least one of the radio frequency transmit system, and the single-sided gradient coil set, to generate an electromagnetic field in a region of interest, wherein the region of interest encompasses the target subject. In accordance with various embodiments, the region of interest has a diameter of 4 to 12 inches.

In accordance with various embodiments, the imaging system is configured to apply a multi-slice excitation comprising exciting multiple slices along an axis of the inhomogeneous permanent gradient field, wherein each of the multiple slices has a bandwidth that is similar to the broad bandwidth of the chirped pulses. In accordance with various embodiments, the chirped pulses comprise identical bandwidths and differing durations. In accordance with various embodiments, the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

In accordance with various embodiments, the chirped pulses are configured to produce a 1-dimensional signal along an axis of the inhomogeneous permanent gradient field. In accordance with various embodiments, the 1-dimensional signal is the first 1-dimensional signal, and the gradient pulses are configured to produce a second 1-dimensional signal and a third 1-dimensional signal that are orthogonal to each other and to the axis of the inhomogeneous permanent gradient field.

In accordance with various embodiments, the gradient pulses are configured for encoding spatial information to the signal. In accordance with various embodiments, the combination of the inhomogeneous permanent gradient field and the chirped pulses are configured for slice selection in the inhomogeneous permanent gradient and a frequency encoding gradient. In accordance with various embodiments, the target subject is an anatomical portion of a body.

In accordance with various embodiments, the receive coil includes an array of receive coils and each of the array of receive coils is configured for specific anatomical portion of a body. In accordance with various embodiments, the chirped pulses induce a signal in the target subject, and the receive coil is configured to receive the signal. In accordance with various embodiments, each of the at least two chirped pulses are split into two components that are 90 degrees out of phase. In accordance with various embodiments, the transmit system further comprises two separate ports configured to generate the at least two chirped pulses.

In accordance with various embodiments, the magnetic resonance imaging system further includes a signal conditioning box and a control system, wherein the signal conditioning box is configured to turn the control system on and off with a blanking signal. In accordance with various embodiments, the magnetic resonance imaging system further includes a radio frequency amplifier, the amplifier enabled and disabled when the control system is turned on and off with the blanking signal.

In accordance with various embodiments, the radio frequency transmit system includes a transmit coil that is non-planar and oriented to partially surround the region of interest.

In accordance with various embodiments, the magnetic resonance imaging system further includes a tuning box, wherein the tuning box is configured to alter the frequency response of the transmit coil.

In accordance with various embodiments, the gradient coil set is non-planar and oriented to partially surround the region of interest, and wherein the gradient coil set is configured to project a magnetic field gradient to the region of interest.

In accordance with various embodiments, the receive coil is a flexible coil configured to be affixed to an anatomical portion of a patient for imaging within the region of interest.

In accordance with various embodiments, the receive coil is in one of a single-loop coil configuration, figure-8 coil configuration, or butterfly coil configuration, wherein the receive coil is smaller than the region of interest. In accordance with various embodiments, the transmit coil and the gradient coil set are concentric about the region of interest.

Figure 11:
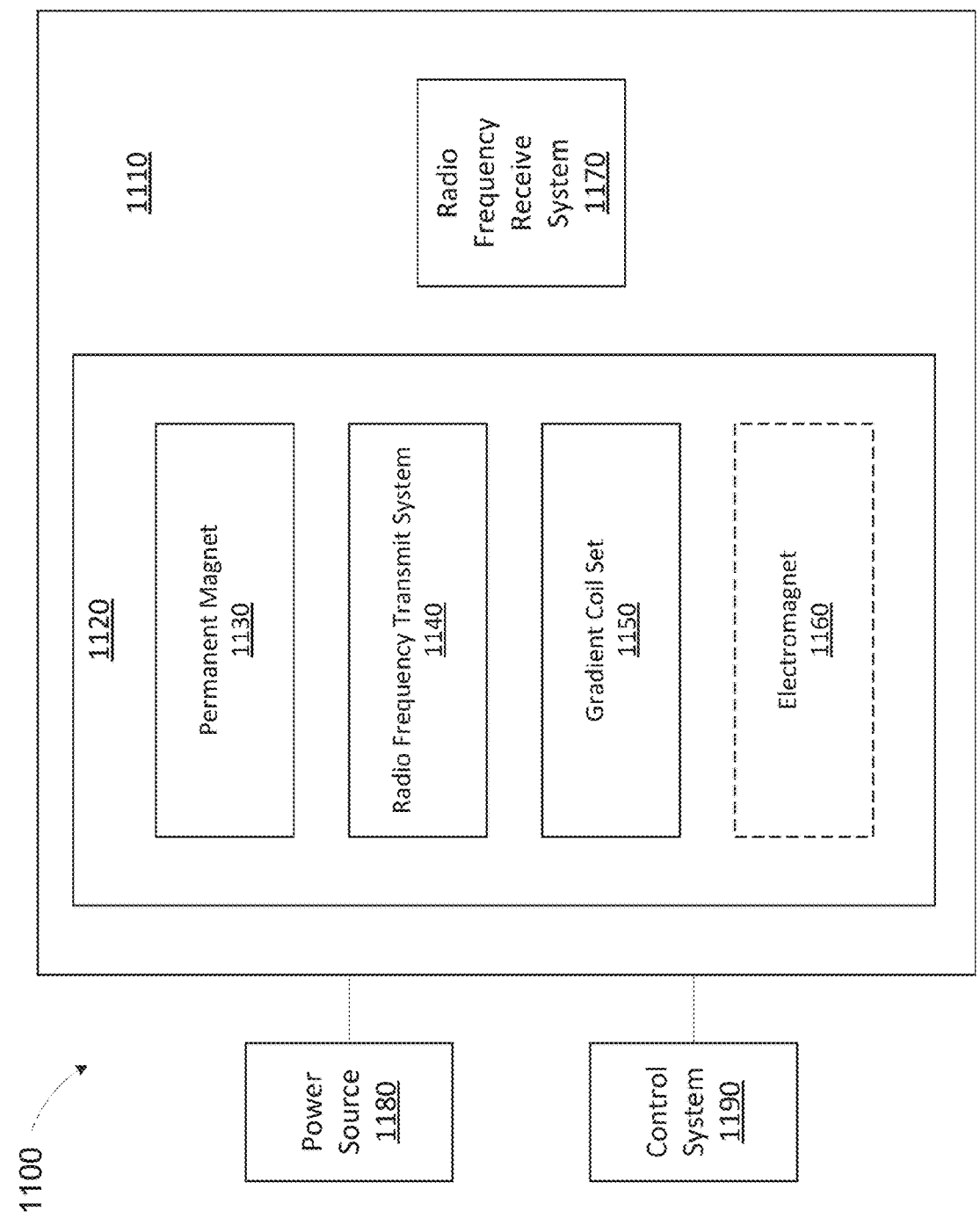
FIG. 11 is a schematic illustration of an example magnetic resonance imaging system, in accordance with various embodiments.

FIG. 11 is a schematic illustration of an example magnetic resonance imaging system 1100, in accordance with various embodiments. The system 1100 includes an imaging system 1110, a power source 1180, and a control system 1190. As shown in FIG. 11, the imaging system 1110 includes a housing 1120 and a radio frequency receive system 1170. As shown in FIG. 11, the housing 1120 includes a permanent magnet 1130, a radio frequency transmit system 1140, a gradient coil set 1150, and an optional electromagnet 1160. In accordance with various embodiments, the system 1100 can include various electronic components, such as for example, but not limited to a varactor, a PIN diode, a capacitor, or a switch, including a micro-electro-mechanical system (MEMS) switch, a solid state relay, or a mechanical relay. In accordance with various embodiments, the various electronic components listed above can be configured with the radio frequency transmit system 1140.

In accordance with various embodiments, since the example system 1100 as shown and described with respect to FIG. 11 is similar to, or include similar components of, the example system 100 as shown and described with respect to FIG. 1, each of the components will not be described in further detail unless specified otherwise. For example, the radio frequency transmit system 1140 can include a radio frequency transmit coil that can be identical, or substantially identical, to the radio frequency transmit coil 140, in accordance with various embodiments. Similarly, the radio frequency receive system 1170 can include a radio frequency receive coil that can be identical, or substantially identical, to the radio frequency receive coil 170, in accordance with various embodiments.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Figure 12:
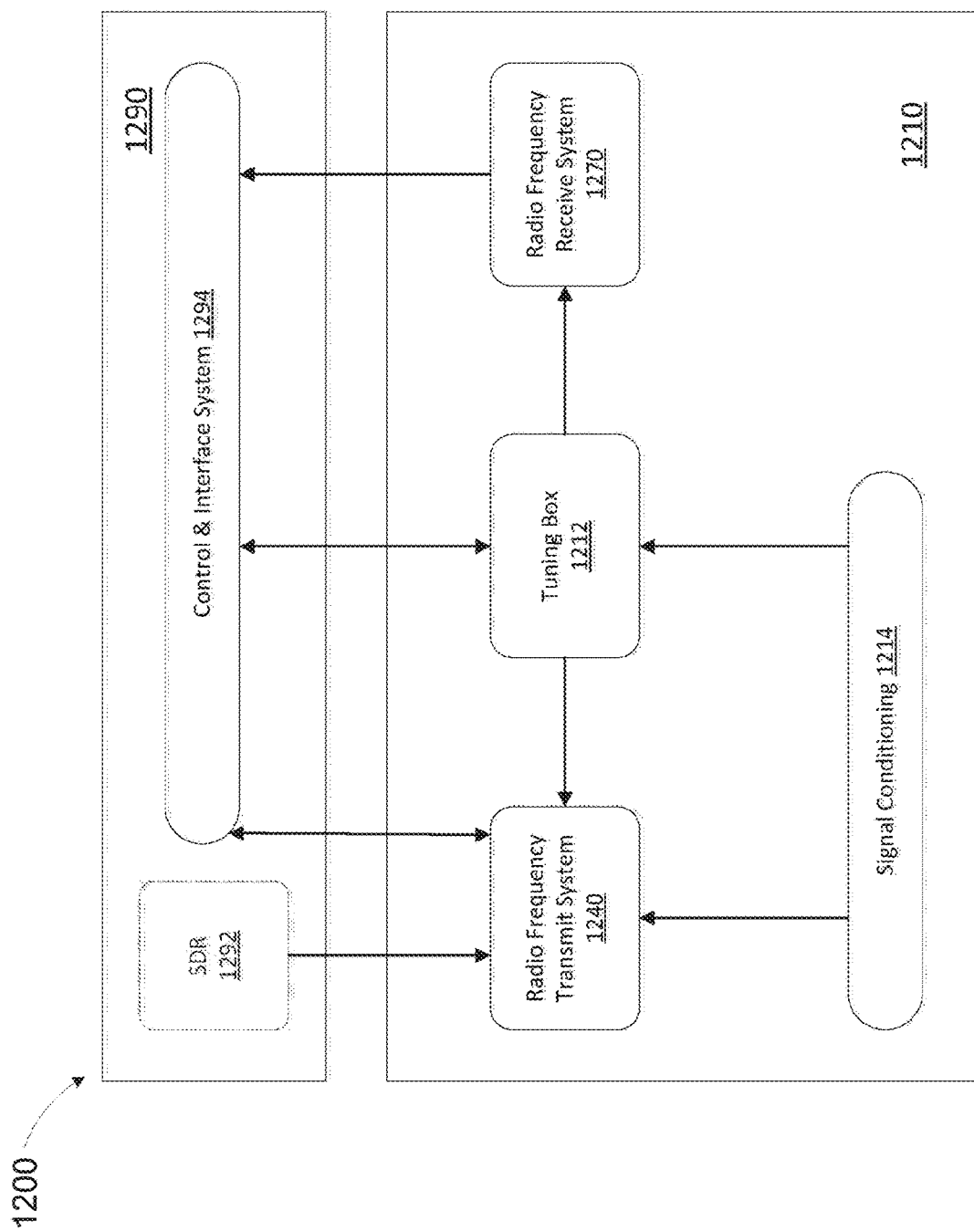
FIG. 12 is a schematic illustration of an example magnetic resonance imaging system, in accordance with various embodiments.

FIG. 12 is a schematic illustration of an example magnetic resonance imaging system 1200, in accordance with various embodiments. As shown in FIG. 12, the imaging system 1200 includes an imaging system 1210 and a control system 1290. The imaging system 1210 includes a radio frequency transmit system (RF-TX) 1240, a radio frequency receive system (RF-RX) 1270, a tuning box 1212, and a signal conditioning box 1214. The control system 1290 includes a software design radio (SDR) 1292 and a control and interface system 1294. In accordance with various embodiments, each of the various components of the system 1200 are communicatively coupled to other components of the system 1200.

In accordance with various embodiments, the various arrows shown in FIG. 12 illustrate the interconnections of the various components in the system 1200 and the workflow thereof. For example, a workflow can begin at a computer resides within the control and interface system 1294. The example workflow includes calculation of a digital waveforms that are needed and in a particular order that they are needed to be applied. Then, the digital waveforms are sent to a SDR 1292, which generates an analog waveform that is sent to the radio frequency transmit system 1240, which includes a radio frequency amplifier and a transmit coil. This amplifies the waveform produced by the SDR 1292 and sends it out into a target subject, e.g., a body, patient or phantom. The properties of this system are adjusted with the signal conditioning box 1214, which turns the imaging system 1210 on and off with a blanking signal, and the tuning box 1212, which adjusts the frequency response of the system. In accordance with various embodiments, the tuning box 1212 is an optional component in the imaging system 1210.

Upon receiving the waveform, the radio frequency transmit system 1240 causes the spins in the target subject to generate a signal, which is detected by the radio frequency receive system 1270. This radio frequency receive system 1270 is also activated and manipulated with a blanking and tuning signal. Like the transmit system 1240, the receive system 1270 does not necessarily require the tuning signal. Once activated and after receiving a signal, the receive system 1270 sends the signal to the imaging system 1210, where it is digitized.

As shown in FIG. 12, the signal conditioning box is configured to set control signals sent to the various components of the system 1200 to values that those components will accept. In accordance with various embodiments, in order to activate an RF amplifier, it requires a high voltage signal that is higher than the SDR 1292 can produce. In such instances, the SDR 1292 can be configured to send a signal to the signal conditioning box 1214, which then amplifies it to a level that the RF amplifier will recognize.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Figure 13:
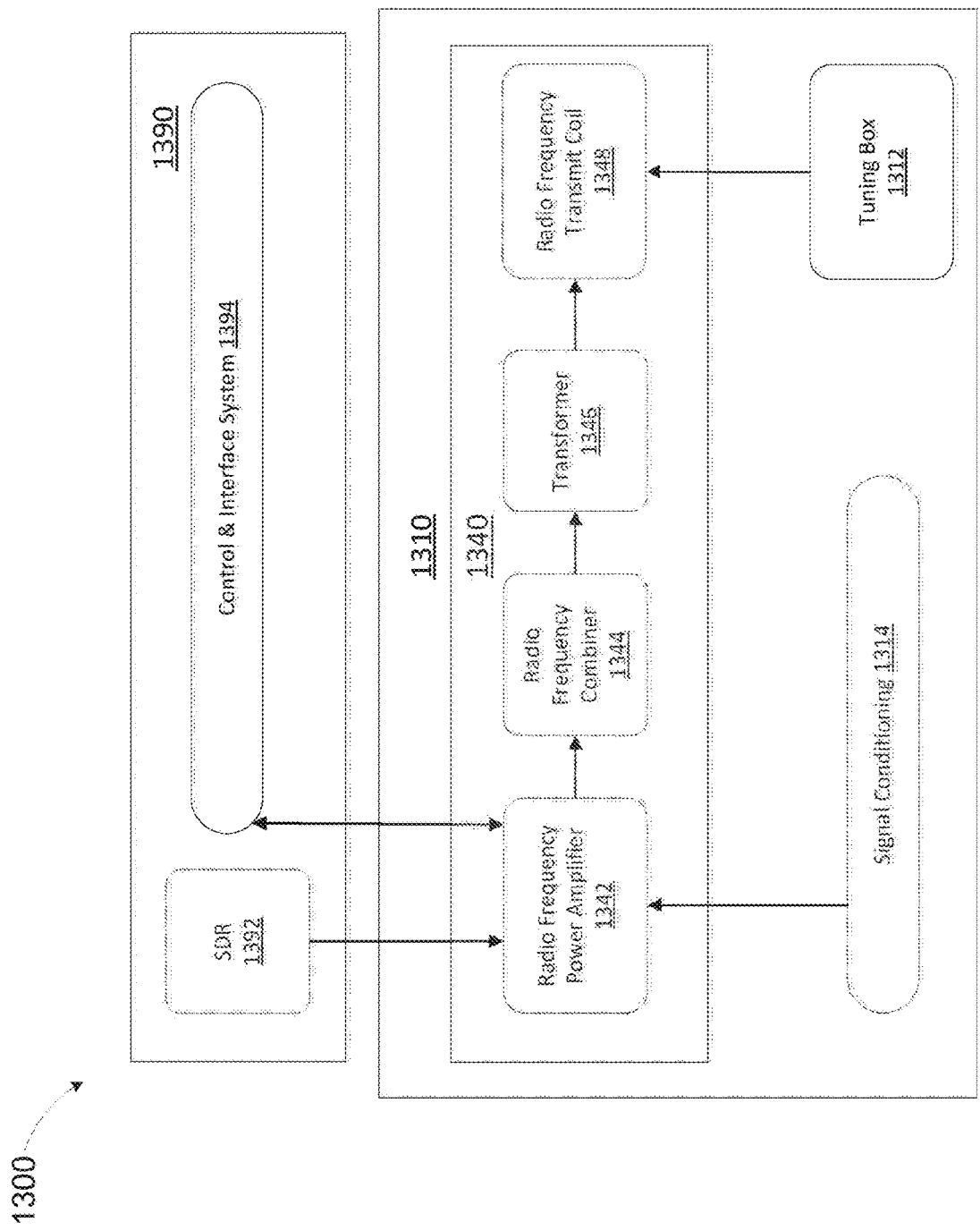
FIG. 13 is a schematic illustration of an example magnetic resonance imaging system, in accordance with various embodiments.

FIG. 13 is a schematic illustration of an example magnetic resonance imaging system 1300, in accordance with various embodiments. As shown in FIG. 13, the imaging system 1300 includes an imaging system 1310 and a control system 1390. The imaging system 1310 includes a radio frequency transmit system 1340, a tuning box 1312, and a signal conditioning box 1314. The control system 1390 includes a SDR 1392 and a control and interface system 1394. As shown in FIG. 13, the radio frequency transmit system 1340 includes a radio frequency power amplifier 1342, a radio frequency combiner 1344, a transformer (such as, a balun) 1346, and a radio frequency transmit coil 1348. In accordance with various embodiments, each of the various components of the system 1300 are communicatively coupled to other components of the system 1300.

In accordance with various embodiments, the various arrows shown in FIG. 13 illustrate the interconnections of the various components in the system 1300 and the workflow thereof. For example, a workflow can begin at a computer resides within the control and interface system 1394. The example workflow includes when an analog waveform is generated in the SDR 1392 and sent to the radio frequency power amplifier 1342. The waveform generated can be a chirped waveform, in accordance with various embodiments. A control signal is also sent to the amplifier 1342 to both turn it on and also to enable it only when the SDR 1392 is sending out a transmission (transmit) pulse. This waveform is amplified and sent to the radio frequency combiner 1344, which splits the wave into two waves 90 degrees out of phase, in accordance with various embodiments. In accordance with various embodiments, the wave is not split into two waves 90 degrees out of phase, but can be instead sent directly to a single port of the transmit coil 1348. These waves are sent to two ports of the transmit coil 1348, which then produces an RF pulse that generates a signal that is detected by a receive system, such as receive systems 1170 or 1270. In accordance with various embodiments, the waves are sent to the transmit coil 1348 via the transformer 1346. In accordance with various embodiments, the system is controlled by the tuning box 1312, which alters the frequency response of the transmit coil 1348 and the signal conditioning box 1314, which enables and disables the amplifier 1342. In accordance with various embodiments, the tuning box 1312 and the transformers or baluns 1346 are optional components in imaging the imaging system 1310.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Figure 14:
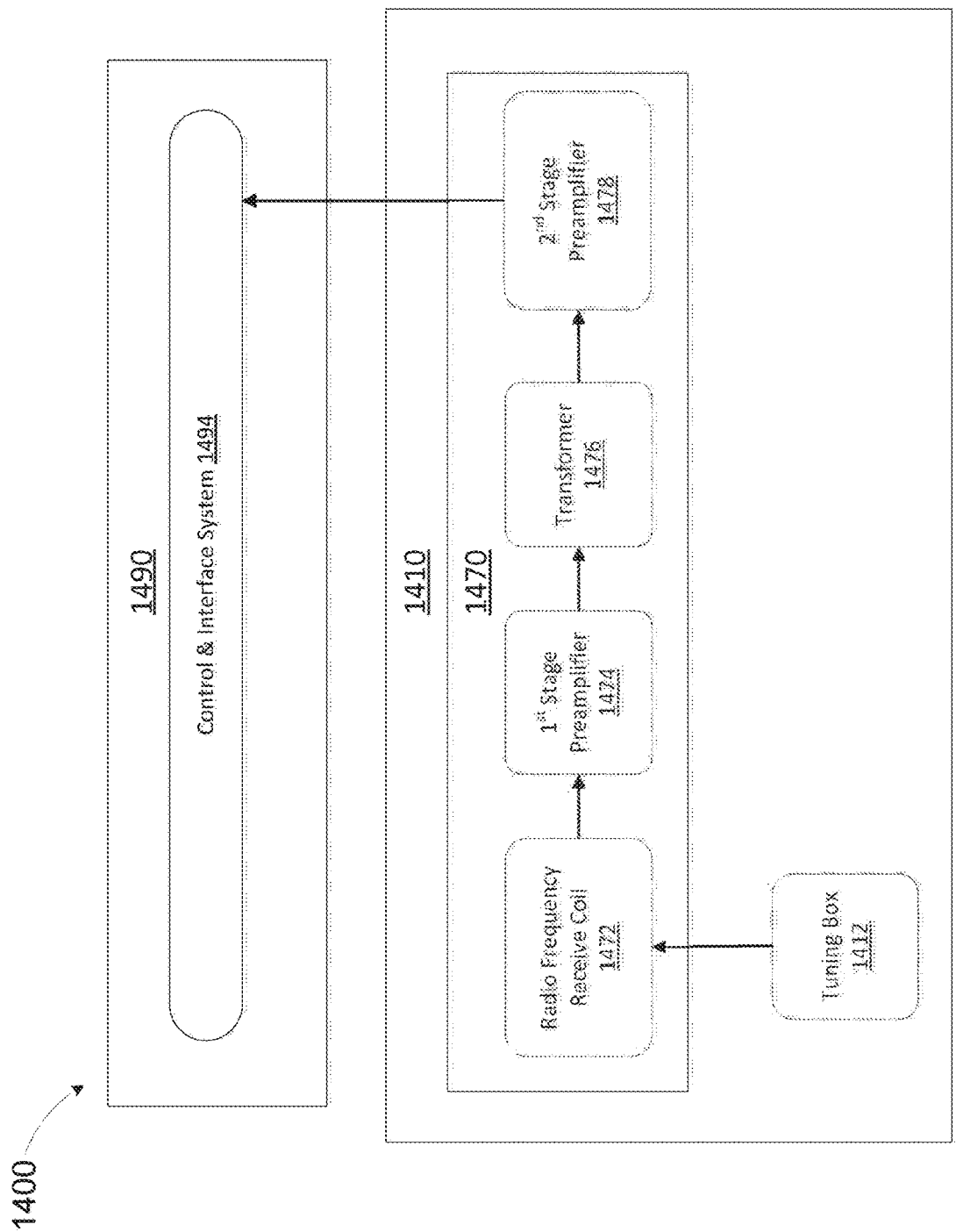
FIG. 14 is a schematic illustration of an example magnetic resonance imaging system, in accordance with various embodiments.

FIG. 14 is a schematic illustration of an example imaging system 1400, in accordance with various embodiments. As shown in FIG. 14, the imaging system 1400 includes an imaging system 1410 and a control system 1490. The control system 1490 includes a control and interface system 1494. The imaging system 1410 includes a radio frequency receive system 1470, and a tuning box 1412. As shown in FIG. 14, the radio frequency receive system 1470 includes a radio frequency receive coil 1472, a first stage preamplifier 1474, a transformer (such as, a balun) 1476, and a second stage preamplifier 1478. In accordance with various embodiments, each of the various components of the system 1400 are communicatively coupled to other components of the system 1400.

In accordance with various embodiments, the various arrows shown in FIG. 14 illustrate the interconnections of the various components in the system 1400 and the workflow thereof. For example, a workflow can begin at a computer resides within the control and interface system 1494. The example workflow includes when radio frequency signals generated by the target subject are detected at the receive system 1470. These signals are induced by an transmit system, such as transmit systems 1140, 1240, or 1340. In accordance with various embodiments, the tuning box 1412 is configured to set the frequencies that the receive coil 1472 is sensitive to. Upon detecting or receiving the signals at the receive coil 1472 at the frequencies that the receive coil 1472 is tuned to, their signals are sent to the first stage preamplifier 1474, which amplifies the received signals. In accordance with various embodiments, the system 1400 becomes less vulnerable to noise by amplification via the first stage preamplifier 1474. The amplified signal is then sent through the transformer 1476 and into another stage of amplification at the second stage preamplifier 1478, to further improve the signal's resistance to noise. From the second stage, the now fully amplified signal is sent to the control and interface system 1494, where it is digitized and processed. The amount of coils may vary depending on the application.

It should be understood that any use of subheadings herein are for organizational purposes, and should not be read to limit the application of those subheaded features to the various embodiments herein. Each and every feature described herein is applicable and usable in all the various embodiments discussed herein and that all features described herein can be used in any contemplated combination, regardless of the specific example embodiments that are described herein. It should further be noted that exemplary description of specific features are used, largely for informational purposes, and not in any way to limit the design, subfeature, and functionality of the specifically described feature.

Workflow Embodiments

In accordance with various embodiments, the various systems, and various combinations of features that make up the various system components and embodiments of the disclosed magnetic resonance imaging system are disclosed herein.

Figure 15:
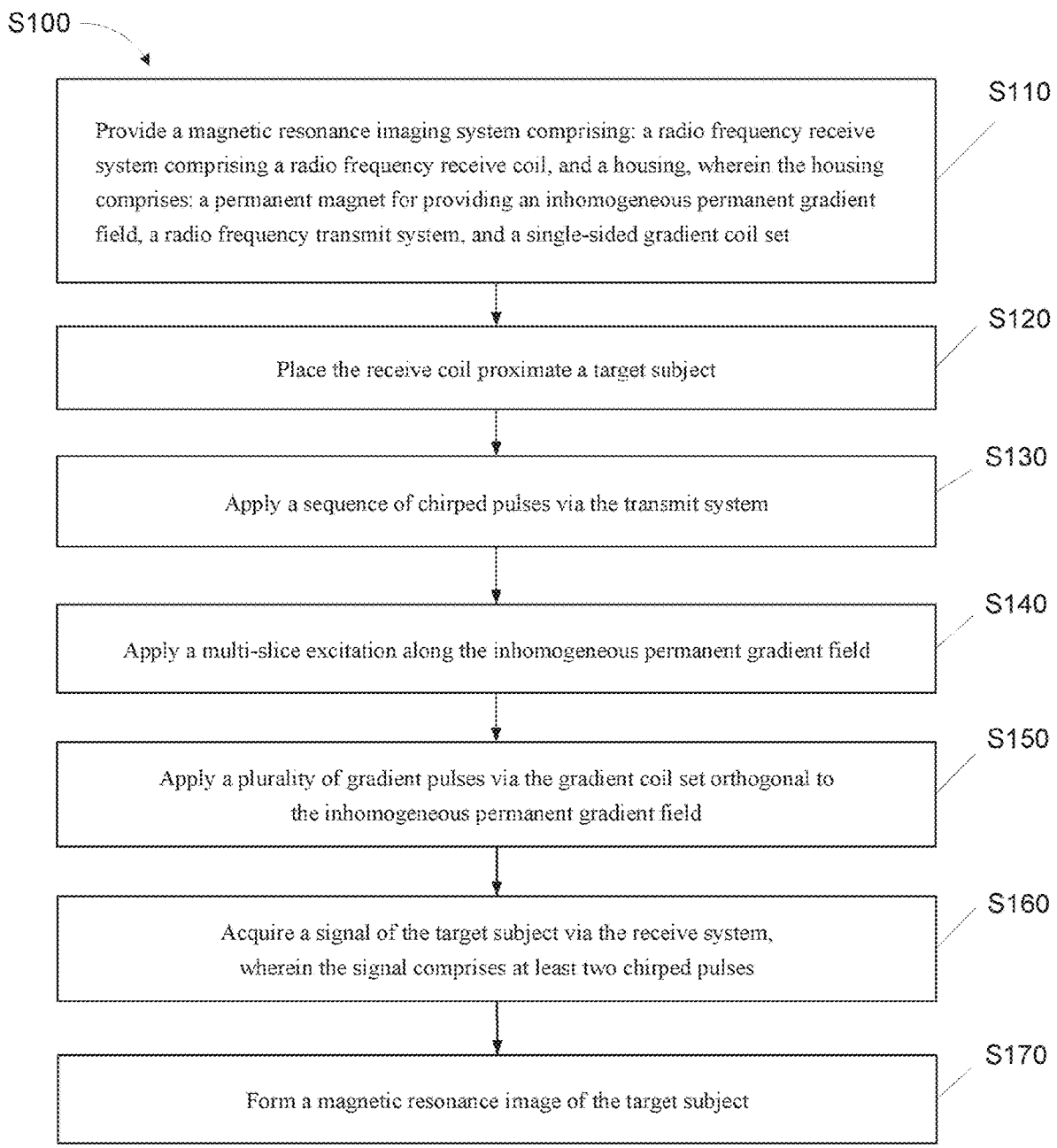
FIG. 15 is a flowchart for a method for performing magnetic resonance imaging, according to various embodiments.

FIG. 15 is a flowchart for a method S100 for performing magnetic resonance imaging, according to various embodiments. The method S100 includes at step S110 providing a magnetic resonance imaging system. The system includes a radio frequency receive system comprising a radio frequency receive coil, and a housing, wherein the housing includes a permanent magnet for providing an inhomogeneous permanent gradient field, a radio frequency transmit system, and a single-sided gradient coil set.

As shown in FIG. 15, the method S100 includes placing the receive coil proximate a target subject, at step S120. The method S100 includes applying a sequence of chirped pulses via the transmit system, at step S130.

As shown in FIG. 15, the method S100 includes applying a multi-slice excitation along the inhomogeneous permanent gradient field, at step S140. The method S100 includes applying a plurality of gradient pulses via the gradient coil set orthogonal to the inhomogeneous permanent gradient field, at step S150.

As shown in FIG. 15, the method S100 includes acquiring a signal of the target subject via the receive system, wherein the signal comprises at least two chirped pulses, at step S160. The method S100 includes forming a magnetic resonance image of the target subject, at step S170.

In accordance with various embodiments, application of the chirped pulses, multi-slice excitation, and gradient pulses are timed so that each magnetization refocuses at a time of acquisition of the signal at the receive system. In accordance with various embodiments, the system further includes a power source, wherein the power source is configured to flow current through at least one of the radio frequency transmit coil, and the single-sided gradient coil set, to generate an electromagnetic field in a region of interest, wherein the region of interest encompasses the target subject. In accordance with various embodiments, the region of interest has a diameter of 4 to 12 inches.

In accordance with various embodiments, the multi-slice excitation includes exciting multiple slices along an axis of the inhomogeneous permanent gradient field, wherein each of the multiple slices has a bandwidth that is similar to the broad bandwidth of the chirped pulses. In accordance with various embodiments, the chirped pulses comprise identical bandwidths and differing durations. In accordance with various embodiments, the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

In accordance with various embodiments, the chirped pulses are configured to produce a 1-dimensional signal along an axis of the inhomogeneous permanent gradient field. In accordance with various embodiments, the 1-dimensional signal is the first 1-dimensional signal, the gradient pulses are configured to produce a second 1-dimensional signal and a third 1-dimensional signal that are orthogonal to each other and to the axis of the inhomogeneous permanent gradient field.

In accordance with various embodiments, the gradient pulses are configured for encoding spatial information to the signal. In accordance with various embodiments, the combination of the inhomogeneous permanent gradient field and the chirped pulses are configured for slice selection in the inhomogeneous permanent gradient and a frequency encoding gradient.

In accordance with various embodiments, the target subject is an anatomical portion of a body. In accordance with various embodiments, the receive coil comprises an array of receive coils and each of the array of receive coils is configured for specific anatomical portion of the body.

In accordance with various embodiments, the chirped pulses induce a signal in the target subject, and the signal is received by the receive coil. In accordance with various embodiments, each of the at least two chirped pulses are split into two components that are 90 degrees out of phase. In accordance with various embodiments, each of the at least two chirped pulses are split into two components that are sent to two separate ports of the transmit system.

In accordance with various embodiments, the magnetic resonance imaging system further comprises a signal conditioning box and a control system, wherein the signal conditioning box is configured to turn the control system on and off with a blanking signal. In accordance with various embodiments, turning the system on and off with the blanking signal respectively enables and disables a radio frequency amplifier.

In accordance with various embodiments, the radio frequency transmit system comprises a transmit coil that is non-planar and oriented to partially surround the region of interest. In accordance with various embodiments, the magnetic resonance imaging system further comprises a tuning box, wherein the tuning box is configured to alter frequency response of the transmit coil.

In accordance with various embodiments, the gradient coil set is non-planar and oriented to partially surround the region of interest, and wherein the gradient coil set is configured to project a magnetic field gradient to the region of interest. In accordance with various embodiments, the receive coil is a flexible coil configured to be affixed to an anatomical portion of a patient for imaging within the region of interest. In accordance with various embodiments, the receive coil is in one of a single-loop coil configuration, figure-8 coil configuration, or butterfly coil configuration, wherein the receive coil is smaller than the region of interest.

In accordance with various embodiments, the transmit coil and the gradient coil set are concentric about the region of interest.

Figure 16:
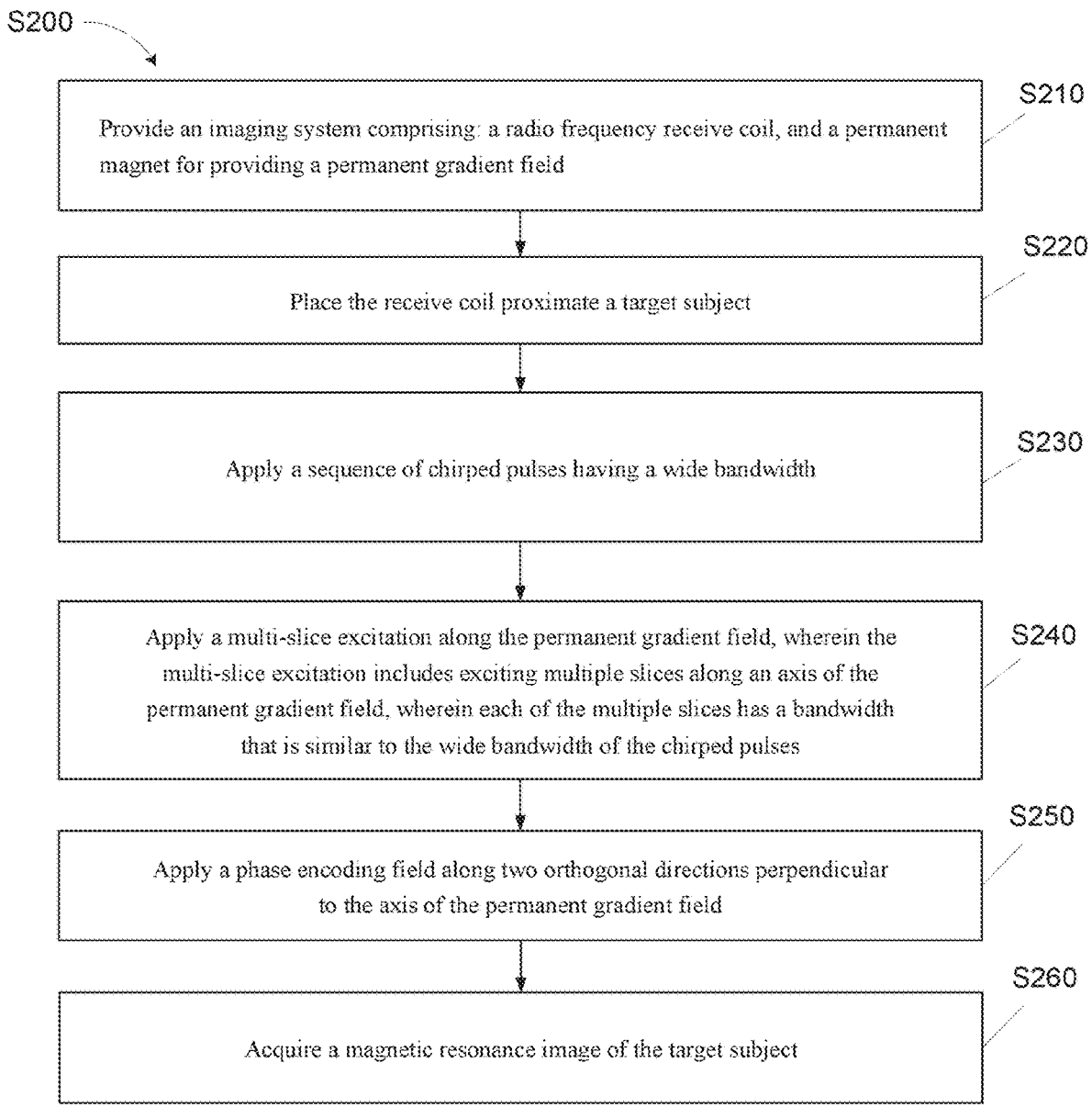
FIG. 16 is a flowchart for another method for performing magnetic resonance imaging, according to various embodiments.

FIG. 16 is a flowchart for a method S200 for performing magnetic resonance imaging, according to various embodiments. The method S200 includes at step S210 providing an imaging system. The system includes a radio frequency receive coil, and a permanent magnet for providing a permanent gradient field.

As shown in FIG. 16, the method S200 includes placing the receive coil proximate a target subject, at step S220. The method S200 includes applying a sequence of chirped pulses having a wide bandwidth, at step S230.

As shown in FIG. 16, the method S200 includes applying a multi-slice excitation along the permanent gradient field, wherein the multi-slice excitation includes exciting multiple slices along an axis of the permanent gradient field, wherein each of the multiple slices has a bandwidth that is similar to the wide bandwidth of the chirped pulses, at step S240.

As shown in FIG. 16, the method S200 includes applying a phase encoding field along two orthogonal directions perpendicular to the axis of the permanent gradient field, at step S250. The method S200 includes acquiring a magnetic resonance image of the target subject, at step S260.

In accordance with various embodiments, application of the chirped pulses, multi-slice excitation, and gradient pulses are timed so that each magnetization refocuses at a time of acquisition of the signal. In accordance with various embodiments, each magnetization focuses in a region of interest, wherein the region of interest encompasses the target subject. In accordance with various embodiments, the region of interest has a diameter of 4 to 12 inches.

In accordance with various embodiments, the chirped pulses comprise identical bandwidths and differing durations. In accordance with various embodiments, the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

In accordance with various embodiments, the chirped pulses are configured to produce a 1-dimensional signal along an axis of the permanent gradient field. In accordance with various embodiments, the 1-dimensional signal is the first 1-dimensional signal, the gradient pulses are configured to produce a second 1-dimensional signal and a third 1-dimensional signal that are orthogonal to each other and to the axis of the permanent gradient field.

In accordance with various embodiments, the gradient pulses are configured for encoding spatial information to the signal. In accordance with various embodiments, the combination of the permanent gradient field and the chirped pulses are configured for slice selection in the permanent gradient and a frequency encoding gradient.

In accordance with various embodiments, the target subject is an anatomical portion of a body.

In accordance with various embodiments, the receive coil comprises an array of receive coils and each of the array of receive coils is configured for specific anatomical portion of the body. In accordance with various embodiments, the chirped pulses induce a signal in the target subject, and the signal is received by the receive coil.

In accordance with various embodiments, the magnetic resonance imaging system further comprises a signal conditioning box and a control system, wherein the signal conditioning box is configured to turn the control system on and off with a blanking signal. In accordance with various embodiments, turning the system on and off with the blanking signal respectively enables and disables a radio frequency amplifier.

In accordance with various embodiments, the imaging system further includes a tuning box and a radio frequency transmit coil, wherein the tuning box is configured to alter frequency response of the transmit coil. In accordance with various embodiments, the transmit coil is non-planar and oriented to partially surround the region of interest.

In accordance with various embodiments, the imaging system further comprises a single-sided gradient coil set, wherein the gradient coil set is non-planar and oriented to partially surround the region of interest, and wherein the gradient coil set is configured to project a magnetic field gradient to the region of interest.

In accordance with various embodiments, the receive coil is a flexible coil configured to be affixed to an anatomical portion of a patient for imaging within the region of interest. In accordance with various embodiments, the receive coil is in one of a single-loop coil configuration, figure-8 coil configuration, or butterfly coil configuration, wherein the receive coil is smaller than the region of interest.

Figure 17:
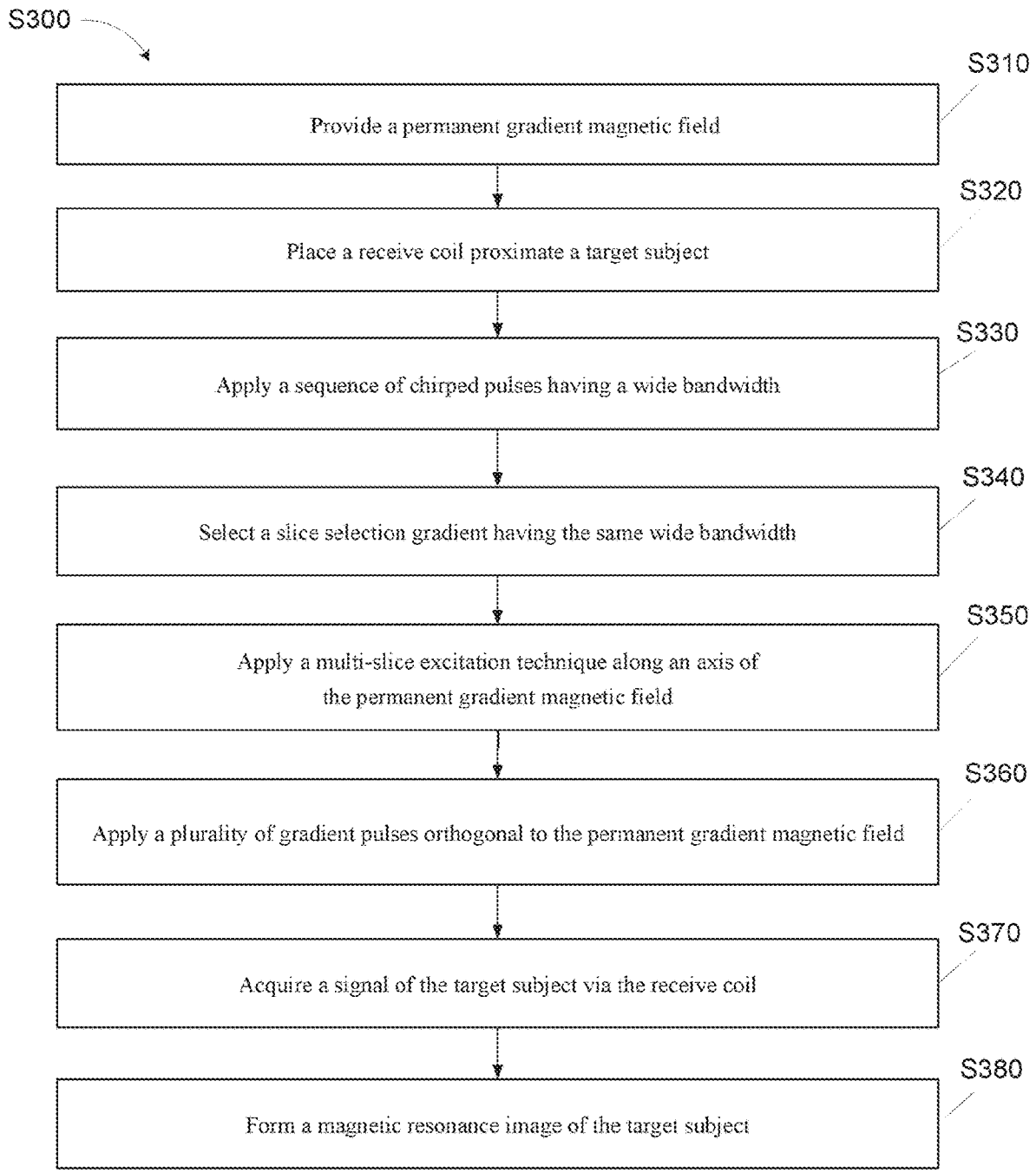
FIG. 17 is a flowchart for another method for performing magnetic resonance imaging, according to various embodiments.

FIG. 17 is a flowchart for a method S300 for performing magnetic resonance imaging, according to various embodiments. The method S300 includes at step S310 providing a permanent gradient magnetic field.

As shown in FIG. 17, the method S300 includes placing a receive coil proximate a target subject, at step S320. The method S300 includes applying a sequence of chirped pulses having a wide bandwidth, at step S330. The method S300 includes selecting a slice selection gradient having the same wide bandwidth, at step S340.

As shown in FIG. 17, the method S300 includes applying a multi-slice excitation technique along an axis of the permanent gradient magnetic field, at step S350. The method S300 includes applying a plurality of gradient pulses orthogonal to the permanent gradient magnetic field, at step S360. The method S300 includes acquiring a signal of the target subject via the receive coil, at step S370. The method S300 includes forming a magnetic resonance image of the target subject, at step S380.

In accordance with various embodiments, application of the chirped pulses, multi-slice excitation technique, and gradient pulses are timed so that each magnetization refocuses at a time of acquisition of the signal. In accordance with various embodiments, each magnetization focuses in a region of interest, wherein the region of interest encompasses the target subject. In accordance with various embodiments, the region of interest has a diameter of 4 to 12 inches.

In accordance with various embodiments, the chirped pulses comprise identical bandwidths and differing durations. In accordance with various embodiments, the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

In accordance with various embodiments, the chirped pulses are configured to produce a 1-dimensional signal along an axis of the permanent gradient field. In accordance with various embodiments, the 1-dimensional signal is the first 1-dimensional signal, the gradient pulses are configured to produce a second 1-dimensional signal and a third 1-dimensional signal that are orthogonal to each other and to the axis of the permanent gradient field.

In accordance with various embodiments, the gradient pulses are configured for encoding spatial information to the signal. In accordance with various embodiments, the combination of the permanent gradient field and the chirped pulses are configured for slice selection in the permanent gradient and a frequency encoding gradient.

In accordance with various embodiments, the target subject is an anatomical portion of a body.

In accordance with various embodiments, the receive coil comprises an array of receive coils and each of the array of receive coils is configured for specific anatomical portion of the body. In accordance with various embodiments, the chirped pulses induce a signal in the target subject, and the signal is received by the receive coil.

In accordance with various embodiments, the magnetic resonance imaging system further comprises a signal conditioning box and a control system, wherein the signal conditioning box is configured to turn the control system on and off with a blanking signal. In accordance with various embodiments, turning the system on and off with the blanking signal respectively enables and disables a radio frequency amplifier.

In accordance with various embodiments, the imaging system further comprises a tuning box and a radio frequency transmit coil, wherein the tuning box is configured to alter frequency response of the transmit coil. In accordance with various embodiments, the transmit coil is non-planar and oriented to partially surround the region of interest.

In accordance with various embodiments, the imaging system further comprises a single-sided gradient coil set, wherein the gradient coil set is non-planar and oriented to partially surround the region of interest, and wherein the gradient coil set is configured to project a magnetic field gradient to the region of interest.

In accordance with various embodiments, the receive coil is a flexible coil configured to be affixed to an anatomical portion of a patient for imaging within the region of interest. In accordance with various embodiments, the receive coil is in one of a single-loop coil configuration, figure-8 coil configuration, or butterfly coil configuration, wherein the receive coil is smaller than the region of interest.

Computer-Implemented System

Figure 18:
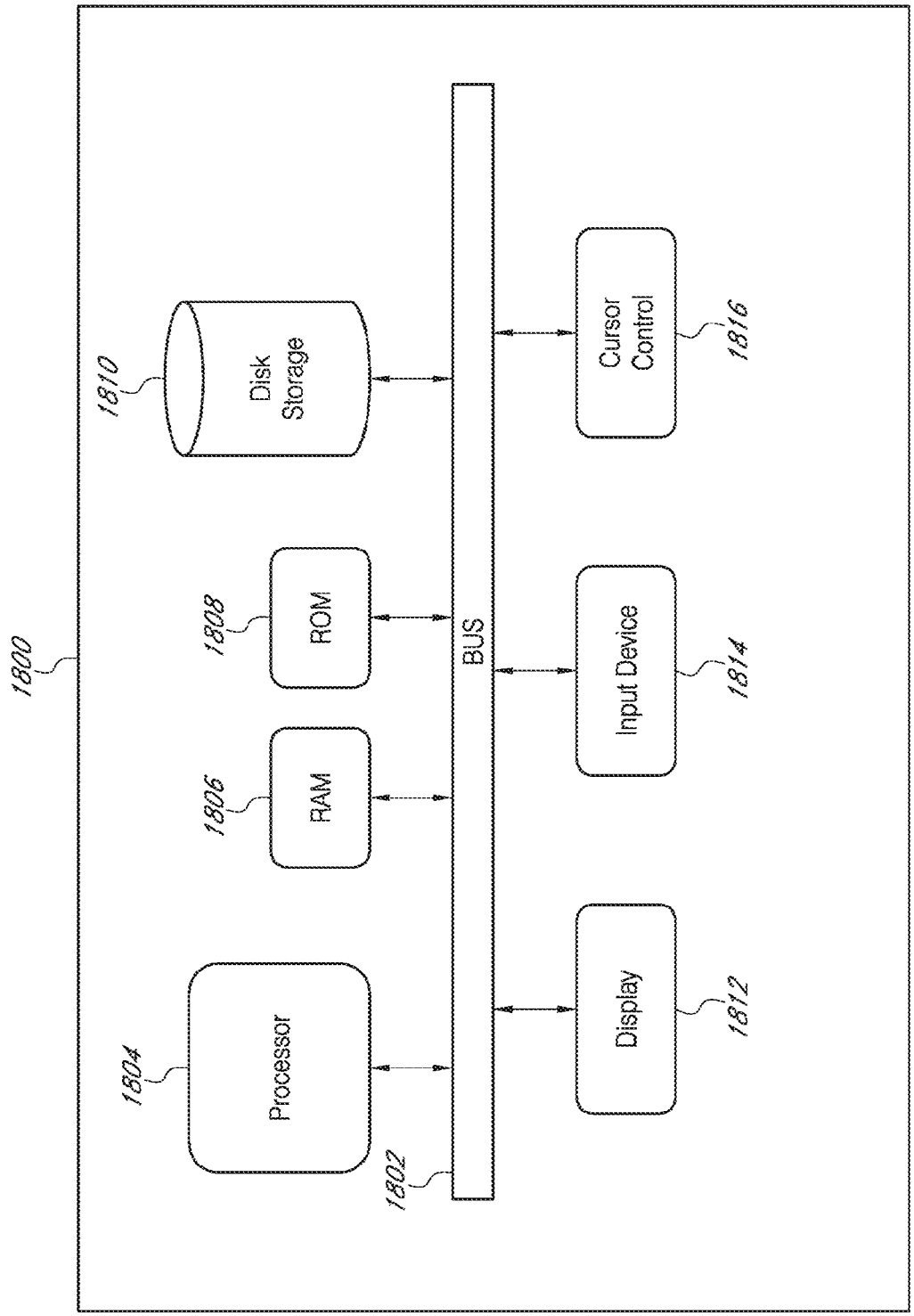
FIG. 18 is a block diagram that illustrates a computer system, in accordance with various embodiments.

FIG. 18 is a block diagram that illustrates a computer system 1800, in accordance with various embodiments. In accordance with various embodiments, the methods S100, S200, and S300 for performing magnetic resonance imaging can be implemented via computer software or hardware. In accordance with various embodiments, the control systems, such as control systems 1190, 1290, 1390, and 1490, or the control and interface systems, such as systems 1294, 1394, and 1494 can be communicatively connected to the computer system 1800 via a network connection that can be either a "hardwired" physical network connection (e.g., Internet, LAN, WAN, VPN, etc.) or a wireless network connection (e.g., Wi-Fi, WLAN, etc.). In various embodiments, the computer system 1800 can be a workstation, mainframe computer, distributed computing node (part of a "cloud computing" or distributed networking system), personal computer, mobile device, etc.

In accordance with various embodiments, the computer system 1800 can include a bus 1802 or other communication mechanism for communicating information, and a processor 1804 coupled with bus 1802 for processing information. In various embodiments, computer system 1800 can also include a memory, which can be a random access memory (RAM) 1806 or other dynamic storage device, coupled to bus 1802 for determining instructions to be executed by processor 1804. Memory also can be used for storing temporary variables or other intermediate information during execution of instructions to be executed by processor 1804. In various embodiments, computer system 1800 can further include a read only memory (ROM) 1808 or other static storage device coupled to bus 1802 for storing static information and instructions for processor 1804. A storage device 1810, such as a magnetic disk or optical disk, can be provided and coupled to bus 1802 for storing information and instructions.

In various embodiments, computer system 1800 can be coupled via bus 1802 to a display 1812, such as a cathode ray tube (CRT) or liquid crystal display (LCD), for displaying information to a computer user. An input device 1814, including alphanumeric and other keys, can be coupled to bus 1802 for communicating information and command selections to processor 1804. Another type of user input device is a cursor control 1816, such as a mouse, a trackball or cursor direction keys for communicating direction information and command selections to processor 1804 and for controlling cursor movement on display 1812. This input device 1814 typically has two degrees of freedom in two axes, a first axis (i.e., x) and a second axis (i.e., y), that allows the device to specify positions in a plane. However, it should be understood that input devices 1814 allowing for 3 dimensional (x, y and z) cursor movement are also contemplated herein.

Consistent with certain implementations of the present teachings, results can be provided by computer system 1800 in response to processor 1804 executing one or more sequences of one or more instructions contained in memory 1806. Such instructions can be read into memory 1806 from another computer-readable medium or computer-readable storage medium, such as storage device 1810. Execution of the sequences of instructions contained in memory 1806 can cause processor 1804 to perform the processes described herein. Alternatively hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 1804 for execution. Such a medium can take many forms, including but not limited to, non-volatile media, volatile media, and transmission media. Examples of non-volatile media can include, but are not limited to, optical, solid state, magnetic disks, such as storage device 1810. Examples of volatile media can include, but are not limited to, dynamic memory, such as memory 1806. Examples of transmission media can include, but are not limited to, coaxial cables, copper wire, and fiber optics, including the wires that comprise bus 1802.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 1804 of computer system 1800 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein flow charts, diagrams and accompanying disclosure can be implemented using computer system 1800 as a standalone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 1800, whereby processor 1804 would execute the analyses and determinations provided by these engines, subject to instructions provided by any one of, or a combination of, memory components 1806/1808/1810 and user input provided via input device 1814.

In accordance with various embodiments, a non-transitory computer-readable medium in which a program is stored for causing a computer to perform a method for performing magnetic resonance imaging is provided. In accordance with various embodiments, the method includes providing a magnetic resonance imaging system. In accordance with various embodiments, the system includes a radio frequency receive system comprising a radio frequency receive coil, and a housing. In accordance with various embodiments, the housing includes a permanent magnet for providing an inhomogeneous permanent gradient field, a radio frequency transmit system, and a single-sided gradient coil set. In accordance with various embodiments, the method further includes placing the receive coil proximate a target subject; applying a sequence of chirped pulses via the transmit system; applying a multi-slice excitation along the inhomogeneous permanent gradient field; applying a plurality of gradient pulses via the gradient coil set orthogonal to the inhomogeneous permanent gradient field; acquiring a signal of the target subject via the receive system, wherein the signal comprises at least two chirped pulses; and forming a magnetic resonance image of the target subject.

In accordance with various embodiments, application of the chirped pulses, multi-slice excitation, and gradient pulses are timed so that each magnetization refocuses at a time of acquisition of the signal at the receive system. In accordance with various embodiments, the system further includes a power source, wherein the power source is configured to flow current through at least one of the radio frequency transmit system, and the single-sided gradient coil set, to generate an electromagnetic field in a region of interest, wherein the region of interest encompasses the target subject. In accordance with various embodiments, the region of interest has a diameter of 4 to 12 inches.

In accordance with various embodiments, the multi-slice excitation includes exciting multiple slices along an axis of the inhomogeneous permanent gradient field, wherein each of the multiple slices has a bandwidth that is similar to the broad bandwidth of the chirped pulses. In accordance with various embodiments, the chirped pulses comprise identical bandwidths and differing durations. In accordance with various embodiments, the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

In accordance with various embodiments, the chirped pulses are configured to produce a 1-dimensional signal along an axis of the inhomogeneous permanent gradient field. In accordance with various embodiments, the 1-dimensional signal is the first 1-dimensional signal, the gradient pulses are configured to produce a second 1-dimensional signal and a third 1-dimensional signal that are orthogonal to each other and to the axis of the inhomogeneous permanent gradient field.

In accordance with various embodiments, the gradient pulses are configured for encoding spatial information to the signal. In accordance with various embodiments, the combination of the inhomogeneous permanent gradient field and the chirped pulses are configured for slice selection in the inhomogeneous permanent gradient and a frequency encoding gradient. In accordance with various embodiments, the target subject is an anatomical portion of a body.

In accordance with various embodiments, the receive coil includes an array of receive coils and each of the array of receive coils is configured for specific anatomical portion of a body. In accordance with various embodiments, the chirped pulses induce a signal in the target subject, and the signal is received by the receive coil. In accordance with various embodiments, each of the at least two chirped pulses are split into two components that are 90 degrees out of phase. In accordance with various embodiments, each of the at least two chirped pulses are split into two components that are sent to two separate ports of the transmit system.

In accordance with various embodiments, the magnetic resonance imaging system further includes a signal conditioning box and a control system, wherein the signal conditioning box is configured to turn the control system on and off with a blanking signal. In accordance with various embodiments, turning the control system on and off with the blanking signal respectively enables and disables a radio frequency amplifier.

In accordance with various embodiments, the radio frequency transmit system includes a transmit coil that is non-planar and oriented to partially surround the region of interest. In accordance with various embodiments, the magnetic resonance imaging system further includes a tuning box, wherein the tuning box is configured to alter the frequency response of the transmit coil. In accordance with various embodiments, the gradient coil set is non-planar and oriented to partially surround the region of interest, and wherein the gradient coil set is configured to project a magnetic field gradient to the region of interest.

In accordance with various embodiments, the receive coil is a flexible coil configured to be affixed to an anatomical portion of a patient for imaging within the region of interest. In accordance with various embodiments, the receive coil is in one of a single-loop coil configuration, figure-8 coil configuration, or butterfly coil configuration, wherein the receive coil is smaller than the region of interest. In accordance with various embodiments, the transmit coil and the gradient coil set are concentric about the region of interest.

In accordance with various embodiments, a non-transitory computer-readable medium in which a program is stored for causing a computer to perform a method for performing magnetic resonance imaging is provided. In accordance with various embodiments, the method includes providing an imaging system comprising a radio frequency receive coil, and a permanent magnet for providing a permanent gradient field. In accordance with various embodiments, the method further includes placing the receive coil proximate a target subject; applying a sequence of chirped pulses having a wide bandwidth; applying a multi-slice excitation along the permanent gradient field, wherein the multi-slice excitation includes exciting multiple slices along an axis of the permanent gradient field, wherein each of the multiple slices has a bandwidth that is similar to the wide bandwidth of the chirped pulses; applying a phase encoding field along two orthogonal directions perpendicular to the axis of the permanent gradient field; and acquiring a magnetic resonance image of the target subject.

In accordance with various embodiments, application of the chirped pulses, multi-slice excitation, and gradient pulses are timed so that each magnetization refocuses at a time of acquisition of a signal. In accordance with various embodiments, each magnetization focuses in a region of interest, wherein the region of interest encompasses the target subject. In accordance with various embodiments, the region of interest has a diameter of 4 to 12 inches.

In accordance with various embodiments, the chirped pulses comprise identical bandwidths and differing durations. In accordance with various embodiments, the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

In accordance with various embodiments, the chirped pulses are configured to produce a 1-dimensional signal along an axis of the permanent gradient field. In accordance with various embodiments, the method further includes applying a plurality of gradient pulses via a gradient coil set orthogonal to the inhomogeneous permanent gradient field, wherein the 1-dimensional signal is the first 1-dimensional signal, the gradient pulses are configured to produce a second 1-dimensional signal and a third 1-dimensional signal that are orthogonal to each other and to the axis of the permanent gradient field.

In accordance with various embodiments, the method further includes applying a plurality of gradient pulses via a gradient coil set orthogonal to the inhomogeneous permanent gradient field, wherein the gradient pulses are configured for encoding spatial information to the signal. In accordance with various embodiments, the combination of the permanent gradient field and the chirped pulses are configured for slice selection in the permanent gradient and a frequency encoding gradient. In accordance with various embodiments, the target subject is an anatomical portion of a body.

In accordance with various embodiments, the receive coil includes an array of receive coils and each of the array of receive coils is configured for a specific anatomical portion of a body. In accordance with various embodiments, the chirped pulses induce a signal in the target subject, and the signal is received by the receive coil.

In accordance with various embodiments, the magnetic resonance imaging system further includes a signal conditioning box and a control system, wherein the signal conditioning box is configured to turn the control system on and off with a blanking signal. In accordance with various embodiments, turning the system on and off with the blanking signal respectively enables and disables a radio frequency amplifier.

In accordance with various embodiments, the imaging system further includes a tuning box and a radio frequency transmit coil, wherein the tuning box is configured to alter the frequency response of the transmit coil. In accordance with various embodiments, the transmit coil is non-planar and oriented to partially surround the region of interest.

In accordance with various embodiments, the imaging system further includes a single-sided gradient coil set, wherein the gradient coil set is non-planar and oriented to partially surround the region of interest, and wherein the gradient coil set is configured to project a magnetic field gradient to the region of interest.

In accordance with various embodiments, the receive coil is a flexible coil configured to be affixed to an anatomical portion of a patient for imaging within the region of interest. In accordance with various embodiments, the receive coil is in one of a single-loop coil configuration, figure-8 coil configuration, or butterfly coil configuration, wherein the receive coil is smaller than the region of interest.

In accordance with various embodiments, a non-transitory computer-readable medium in which a program is stored for causing a computer to perform a method for performing magnetic resonance imaging is provided. In accordance with various embodiments, the method includes providing a permanent gradient magnetic field; placing a receive coil proximate a target subject; applying a sequence of chirped pulses having a wide bandwidth; selecting a slice selection gradient having the same wide bandwidth; applying a multi-slice excitation technique along an axis of the permanent gradient magnetic field; applying a plurality of gradient pulses orthogonal to the permanent gradient magnetic field; acquiring a signal of the target subject via the receive coil; and forming a magnetic resonance image of the target subject.

In accordance with various embodiments, application of the chirped pulses, multi-slice excitation technique, and gradient pulses are timed so that each magnetization refocuses at a time of acquisition of the signal. In accordance with various embodiments, each magnetization focuses in a region of interest, wherein the region of interest encompasses the target subject. In accordance with various embodiments, the region of interest has a diameter of 4 to 12 inches.

In accordance with various embodiments, the chirped pulses comprise identical bandwidths and differing durations. In accordance with various embodiments, the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

In accordance with various embodiments, the chirped pulses are configured to produce a 1-dimensional signal along an axis of the permanent gradient field. In accordance with various embodiments, the 1-dimensional signal is the first 1-dimensional signal, the gradient pulses are configured to produce a second 1-dimensional signal and a third 1-dimensional signal that are orthogonal to each other and to the axis of the permanent gradient field.

In accordance with various embodiments, the gradient pulses are configured for encoding spatial information to the signal. In accordance with various embodiments, the combination of the permanent gradient field and the chirped pulses are configured for slice selection in the permanent gradient and a frequency encoding gradient. In accordance with various embodiments, the target subject is an anatomical portion of a body.

In accordance with various embodiments, the receive coil comprises an array of receive coils and each of the array of receive coils is configured for specific anatomical portion of a body. In accordance with various embodiments, the chirped pulses induce a signal in the target subject, and the signal is received by the receive coil.

In accordance with various embodiments, the magnetic resonance imaging system further includes a signal conditioning box and a control system, wherein the signal conditioning box is configured to turn the control system on and off with a blanking signal. In accordance with various embodiments, turning the system on and off with the blanking signal respectively enables and disables a radio frequency amplifier.

In accordance with various embodiments, the imaging system further includes a tuning box and a radio frequency transmit coil, wherein the tuning box is configured to alter frequency response of the transmit coil. In accordance with various embodiments, the transmit coil is non-planar and oriented to partially surround the region of interest.

In accordance with various embodiments, the imaging system further includes a single-sided gradient coil set, wherein the gradient coil set is non-planar and oriented to partially surround the region of interest, and wherein the gradient coil set is configured to project a magnetic field gradient to the region of interest.

In accordance with various embodiments, the receive coil is a flexible coil configured to be affixed to an anatomical portion of a patient for imaging within the region of interest. In accordance with various embodiments, the receive coil is in one of a single-loop coil configuration, figure-8 coil configuration, or butterfly coil configuration, wherein the receive coil is smaller than the region of interest.

RECITATION OF EMBODIMENTS

EMBODIMENT 1. A method for performing magnetic resonance imaging comprising providing a magnetic resonance imaging system comprising a radio frequency receive system comprising a radio frequency receive coil, and a housing, wherein the housing comprises a permanent magnet for providing an inhomogeneous permanent gradient field, a radio frequency transmit system, and a single-sided gradient coil set. The method further comprises placing the receive coil proximate a target subject; applying a sequence of chirped pulses via the transmit system; applying a multi-slice excitation along the inhomogeneous permanent gradient field; applying a plurality of gradient pulses via the gradient coil set orthogonal to the inhomogeneous permanent gradient field; acquiring a signal of the target subject via the receive system, wherein the signal comprises at least two chirped pulses; and forming a magnetic resonance image of the target subject.

EMBODIMENT 2. The method of embodiment 1, wherein application of the chirped pulses, multi-slice excitation, and gradient pulses are timed so that each magnetization refocuses at a time of acquisition of the signal at the receive system.

EMBODIMENT 3. The method of any preceding embodiment, further comprising a power source, wherein the power source is configured to flow current through at least one of the radio frequency transmit system, and the single-sided gradient coil set, to generate an electromagnetic field in a region of interest, wherein the region of interest encompasses the target subject.

EMBODIMENT 4. The method of embodiment 3, wherein the region of interest has a diameter of 4 to 12 inches.

EMBODIMENT 5. The method of any preceding embodiment, wherein the multi-slice excitation includes exciting multiple slices along an axis of the inhomogeneous permanent gradient field, wherein each of the multiple slices has a bandwidth that is similar to the broad bandwidth of the chirped pulses.

EMBODIMENT 6. The method of any preceding embodiment, wherein the chirped pulses comprise identical bandwidths and differing durations.

EMBODIMENT 7. The method of any preceding embodiment, wherein the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

EMBODIMENT 8. The method of any preceding embodiment, wherein the chirped pulses are configured to produce a 1-dimensional signal along an axis of the inhomogeneous permanent gradient field.

EMBODIMENT 9. The method of embodiment 8, wherein the 1-dimensional signal is the first 1-dimensional signal, the gradient pulses are configured to produce a second 1-dimensional signal and a third 1-dimensional signal that are orthogonal to each other and to the axis of the inhomogeneous permanent gradient field.

EMBODIMENT 10. The method of any preceding embodiment, wherein the gradient pulses are configured for encoding spatial information to the signal.

EMBODIMENT 11. The method of any preceding embodiment, wherein the combination of the inhomogeneous permanent gradient field and the chirped pulses are configured for slice selection in the inhomogeneous permanent gradient and a frequency encoding gradient.

EMBODIMENT 12. The method of any preceding embodiment, wherein the target subject is an anatomical portion of a body.

EMBODIMENT 13. The method of any preceding embodiment, wherein the receive coil comprises an array of receive coils and each of the array of receive coils is configured for specific anatomical portion of a body.

EMBODIMENT 14. The method of any preceding embodiment, wherein the chirped pulses induce a signal in the target subject, and the signal is received by the receive coil.

EMBODIMENT 15. The method of any preceding embodiment, wherein each of the at least two chirped pulses are split into two components that are 90 degrees out of phase.

EMBODIMENT 16. The method of any preceding embodiment, wherein each of the at least two chirped pulses are split into two components that are sent to two separate ports of the transmit system.

EMBODIMENT 17. The method of any preceding embodiment, wherein the magnetic resonance imaging system further comprises a signal conditioning box and a control system, wherein the signal conditioning box is configured to turn the control system on and off with a blanking signal.

EMBODIMENT 18. The method of embodiment 17, wherein turning the control system on and off with the blanking signal respectively enables and disables a radio frequency amplifier.

EMBODIMENT 19. The method of embodiment 3, wherein the radio frequency transmit system comprises a transmit coil that is non-planar and oriented to partially surround the region of interest.

EMBODIMENT 20. The method of embodiment 19, wherein the magnetic resonance imaging system further comprises a tuning box, wherein the tuning box is configured to alter the frequency response of the transmit coil.

EMBODIMENT 21. The method of embodiment 3, wherein the gradient coil set is non-planar and oriented to partially surround the region of interest, and wherein the gradient coil set is configured to project a magnetic field gradient to the region of interest.

EMBODIMENT 22. The method of embodiment 3, wherein the receive coil is a flexible coil configured to be affixed to an anatomical portion of a patient for imaging within the region of interest.

EMBODIMENT 23. The method of embodiment 3, wherein the receive coil is in one of a single-loop coil configuration, figure-8 coil configuration, or butterfly coil configuration, wherein the receive coil is smaller than the region of interest.

EMBODIMENT 24. The method of embodiment 19, wherein the transmit coil and the gradient coil set are concentric about the region of interest.

EMBODIMENT 25. A method for performing magnetic resonance imaging comprising providing an imaging system comprising a radio frequency receive coil, and a permanent magnet for providing a permanent gradient field. The method further comprises placing the receive coil proximate a target subject; applying a sequence of chirped pulses having a wide bandwidth; applying a multi-slice excitation along the permanent gradient field, wherein the multi-slice excitation includes exciting multiple slices along an axis of the permanent gradient field, wherein each of the multiple slices has a bandwidth that is similar to the wide bandwidth of the chirped pulses; applying a phase encoding field along two orthogonal directions perpendicular to the axis of the permanent gradient field; and acquiring a magnetic resonance image of the target subject.

EMBODIMENT 26. The method of embodiment 25, wherein application of the chirped pulses, multi-slice excitation, and gradient pulses are timed so that each magnetization refocuses at a time of acquisition of a signal.

EMBODIMENT 27. The method of embodiment 26, wherein each magnetization focuses in a region of interest, wherein the region of interest encompasses the target subject.

EMBODIMENT 28. The method of embodiment 27, wherein the region of interest has a diameter of 4 to 12 inches.

EMBODIMENT 29. The method of any of embodiments 25 to 28, wherein the chirped pulses comprise identical bandwidths and differing durations.

EMBODIMENT 30. The method of embodiment 29, wherein the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

EMBODIMENT 31. The method of any of embodiments 25 to 30, wherein the chirped pulses are configured to produce a 1-dimensional signal along an axis of the permanent gradient field.

EMBODIMENT 32. The method of embodiment 31, further comprising applying a plurality of gradient pulses via a gradient coil set orthogonal to the inhomogeneous permanent gradient field, wherein the 1-dimensional signal is the first 1-dimensional signal, the gradient pulses are configured to produce a second 1-dimensional signal and a third 1-dimensional signal that are orthogonal to each other and to the axis of the permanent gradient field.

EMBODIMENT 33. The method of any of embodiments 25 to 32, further comprising applying a plurality of gradient pulses via a gradient coil set orthogonal to the inhomogeneous permanent gradient field, wherein the gradient pulses are configured for encoding spatial information to the signal.

EMBODIMENT 34. The method of any of embodiments 25 to 33, wherein the combination of the permanent gradient field and the chirped pulses are configured for slice selection in the permanent gradient and a frequency encoding gradient.

EMBODIMENT 35. The method of any of embodiments 25 to 34, wherein the target subject is an anatomical portion of a body.

EMBODIMENT 36. The method of any of embodiments 25 to 35, wherein the receive coil comprises an array of receive coils and each of the array of receive coils is configured for a specific anatomical portion of a body.

EMBODIMENT 37. The method of any of embodiments 25 to 36, wherein the chirped pulses induce a signal in the target subject, and the signal is received by the receive coil.

EMBODIMENT 38. The method of any of embodiments 25 to 37, wherein the magnetic resonance imaging system further comprises a signal conditioning box and a control system, wherein the signal conditioning box is configured to turn the control system on and off with a blanking signal.

EMBODIMENT 39. The method of embodiment 38, wherein turning the system on and off with the blanking signal respectively enables and disables a radio frequency amplifier.

EMBODIMENT 40. The method of embodiment 27, wherein the imaging system further comprises a tuning box and a radio frequency transmit coil, wherein the tuning box is configured to alter the frequency response of the transmit coil.

EMBODIMENT 41. The method of embodiment 40, wherein the transmit coil is non-planar and oriented to partially surround the region of interest.

EMBODIMENT 42. The method of embodiment 27, wherein the imaging system further comprises a single-sided gradient coil set, wherein the gradient coil set is non-planar and oriented to partially surround the region of interest, and wherein the gradient coil set is configured to project a magnetic field gradient to the region of interest.

EMBODIMENT 43. The method of embodiment 27, wherein the receive coil is a flexible coil configured to be affixed to an anatomical portion of a patient for imaging within the region of interest.

EMBODIMENT 44. The method of embodiment 27, wherein the receive coil is in one of a single-loop coil configuration, figure-8 coil configuration, or butterfly coil configuration, wherein the receive coil is smaller than the region of interest.

EMBODIMENT 45. A method for performing magnetic resonance imaging comprising providing a permanent gradient magnetic field; placing a receive coil proximate a target subject; applying a sequence of chirped pulses having a wide bandwidth; selecting a slice selection gradient having the same wide bandwidth; applying a multi-slice excitation technique along an axis of the permanent gradient magnetic field; applying a plurality of gradient pulses orthogonal to the permanent gradient magnetic field; acquiring a signal of the target subject via the receive coil; and forming a magnetic resonance image of the target subject.

EMBODIMENT 46. The method of embodiment 45, wherein application of the chirped pulses, multi-slice excitation technique, and gradient pulses are timed so that each magnetization refocuses at a time of acquisition of the signal.

EMBODIMENT 47. The method of embodiment 46, wherein each magnetization focuses in a region of interest, wherein the region of interest encompasses the target subject.

EMBODIMENT 48. The method of embodiment 47, wherein the region of interest has a diameter of 4 to 12 inches.

EMBODIMENT 49. The method of any of embodiments 45 to 48, wherein the chirped pulses comprise identical bandwidths and differing durations.

EMBODIMENT 50. The method of embodiment 49, wherein the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

EMBODIMENT 51. The method of any of embodiments 45 to 50, wherein the chirped pulses are configured to produce a 1-dimensional signal along an axis of the permanent gradient field.

EMBODIMENT 52. The method of embodiment 51, wherein the 1-dimensional signal is the first 1-dimensional signal, the gradient pulses are configured to produce a second 1-dimensional signal and a third 1-dimensional signal that are orthogonal to each other and to the axis of the permanent gradient field.

EMBODIMENT 53. The method of any of embodiments 45 to 52, wherein the gradient pulses are configured for encoding spatial information to the signal.

EMBODIMENT 54. The method of any of embodiments 45 to 53, wherein the combination of the permanent gradient field and the chirped pulses are configured for slice selection in the permanent gradient and a frequency encoding gradient.

EMBODIMENT 55. The method of any of embodiments 45 to 54, wherein the target subject is an anatomical portion of a body.

EMBODIMENT 56. The method of any of embodiments 45 to 55, wherein the receive coil comprises an array of receive coils and each of the array of receive coils is configured for specific anatomical portion of a body.

EMBODIMENT 57. The method of any of embodiments 45 to 56, wherein the chirped pulses induce a signal in the target subject, and the signal is received by the receive coil.

EMBODIMENT 58. The method of any of embodiments 45 to 57, wherein the magnetic resonance imaging system further comprises a signal conditioning box and a control system, wherein the signal conditioning box is configured to turn the control system on and off with a blanking signal.

EMBODIMENT 59. The method of embodiment 58, wherein turning the system on and off with the blanking signal respectively enables and disables a radio frequency amplifier.

EMBODIMENT 60. The method of embodiment 47, wherein the imaging system further comprises a tuning box and a radio frequency transmit coil, wherein the tuning box is configured to alter frequency response of the transmit coil.

EMBODIMENT 61. The method of embodiment 60, wherein the transmit coil is non-planar and oriented to partially surround the region of interest.

EMBODIMENT 62. The method of embodiment 47, wherein the imaging system further comprises a single-sided gradient coil set, wherein the gradient coil set is non-planar and oriented to partially surround the region of interest, and wherein the gradient coil set is configured to project a magnetic field gradient to the region of interest.

EMBODIMENT 63. The method of embodiment 47, wherein the receive coil is a flexible coil configured to be affixed to an anatomical portion of a patient for imaging within the region of interest.

EMBODIMENT 64. The method of embodiment 47, wherein the receive coil is in one of a single-loop coil configuration, figure-8 coil configuration, or butterfly coil configuration, wherein the receive coil is smaller than the region of interest.

EMBODIMENT 65. A magnetic resonance imaging system comprising a radio frequency receive system comprising a radio frequency receive coil configured to be placed proximate a target subject, wherein the receive system is configured to deliver a signal of a target subject for forming a magnetic resonance image of the target subject, wherein the signal comprises at least two chirped pulses, and a housing, wherein the housing comprises a permanent magnet for providing an inhomogeneous permanent gradient field, wherein the imaging system is configured to apply a multi-slice excitation along the inhomogeneous permanent gradient field, a radio frequency transmit system configured to deliver a sequence of chirped pulses, and a single-sided gradient coil set configured to deliver a plurality of gradient pulses orthogonal to the inhomogeneous permanent gradient field.

EMBODIMENT 66. The system of embodiment 65, further comprising a power source, wherein the power source is configured to flow current through at least one of the radio frequency transmit system, and the single-sided gradient coil set, to generate an electromagnetic field in a region of interest, wherein the region of interest encompasses the target subject.

EMBODIMENT 67. The system of embodiment 66, wherein the region of interest has a diameter of 4 to 12 inches.

EMBODIMENT 68. The method of any of embodiments 65 to 67, wherein the imaging system is configured to apply a multi-slice excitation comprising exciting multiple slices along an axis of the inhomogeneous permanent gradient field, wherein each of the multiple slices has a bandwidth that is similar to the broad bandwidth of the chirped pulses.

EMBODIMENT 69. The system of any of embodiments 65 to 68, wherein the chirped pulses comprise identical bandwidths and differing durations.

EMBODIMENT 70. The system of any of embodiments 65 to 69, wherein the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

EMBODIMENT 71. The system of any of embodiments 65 to 70, wherein the chirped pulses are configured to produce a 1-dimensional signal along an axis of the inhomogeneous permanent gradient field.

EMBODIMENT 72. The system of embodiment 71, wherein the 1-dimensional signal is the first 1-dimensional signal, and the gradient pulses are configured to produce a second 1-dimensional signal and a third 1-dimensional signal that are orthogonal to each other and to the axis of the inhomogeneous permanent gradient field.

EMBODIMENT 73. The system of any of embodiments 65 to 72, wherein the gradient pulses are configured for encoding spatial information to the signal.

EMBODIMENT 74. The system of any of embodiments 65 to 73, wherein the combination of the inhomogeneous permanent gradient field and the chirped pulses are configured for slice selection in the inhomogeneous permanent gradient and a frequency encoding gradient.

EMBODIMENT 75. The system of any of embodiments 65 to 74, wherein the target subject is an anatomical portion of a body.

EMBODIMENT 76. The system of any of embodiments 65 to 75, wherein the receive coil comprises an array of receive coils and each of the array of receive coils is configured for specific anatomical portion of a body.

EMBODIMENT 77. The system of any of embodiments 65 to 76, wherein the chirped pulses induce a signal in the target subject, and the receive coil is configured to receive the signal.

EMBODIMENT 78. The system of any of embodiments 65 to 77, wherein each of the at least two chirped pulses are split into two components that are 90 degrees out of phase.

EMBODIMENT 79. The system of any of embodiments 65 to 78, wherein the transmit system further comprises two separate ports configured to generate the at least two chirped pulses.

EMBODIMENT 80. The system of any of embodiments 65 to 79, wherein the magnetic resonance imaging system further comprises a signal conditioning box and a control system, wherein the signal conditioning box is configured to turn the control system on and off with a blanking signal.

EMBODIMENT 81. The system of embodiment 80, further comprising a radio frequency amplifier, the amplifier enabled and disabled when the control system is turned on and off with the blanking signal.

EMBODIMENT 82. The system of embodiment 66, wherein the radio frequency transmit system comprises a transmit coil that is non-planar and oriented to partially surround the region of interest.

EMBODIMENT 83. The system of embodiment 82, wherein the magnetic resonance imaging system further comprises a tuning box, wherein the tuning box is configured to alter the frequency response of the transmit coil.

EMBODIMENT 84. The system of embodiment 66, wherein the gradient coil set is non-planar and oriented to partially surround the region of interest, and wherein the gradient coil set is configured to project a magnetic field gradient to the region of interest.

EMBODIMENT 85. The system of embodiment 66, wherein the receive coil is a flexible coil configured to be affixed to an anatomical portion of a patient for imaging within the region of interest.

EMBODIMENT 86. The system of embodiment 66, wherein the receive coil is in one of a single-loop coil configuration, figure-8 coil configuration, or butterfly coil configuration, wherein the receive coil is smaller than the region of interest.

EMBODIMENT 87. The system of embodiment 82, wherein the transmit coil and the gradient coil set are concentric about the region of interest.

EMBODIMENT 88. A non-transitory computer-readable medium in which a program is stored for causing a computer to perform a method for performing magnetic resonance imaging, the method comprising providing a magnetic resonance imaging system comprising a radio frequency receive system comprising a radio frequency receive coil, and a housing, wherein the housing comprises a permanent magnet for providing an inhomogeneous permanent gradient field, a radio frequency transmit system, and a single-sided gradient coil set. The method further comprises placing the receive coil proximate a target subject; applying a sequence of chirped pulses via the transmit system; applying a multi-slice excitation along the inhomogeneous permanent gradient field; applying a plurality of gradient pulses via the gradient coil set orthogonal to the inhomogeneous permanent gradient field; acquiring a signal of the target subject via the receive system, wherein the signal comprises at least two chirped pulses; and forming a magnetic resonance image of the target subject.

EMBODIMENT 89. The method of embodiment 88, wherein application of the chirped pulses, multi-slice excitation, and gradient pulses are timed so that each magnetization refocuses at a time of acquisition of the signal at the receive system.

EMBODIMENT 90. The method of any of embodiments 88 and 89, further comprising a power source, wherein the power source is configured to flow current through at least one of the radio frequency transmit system, and the single-sided gradient coil set, to generate an electromagnetic field in a region of interest, wherein the region of interest encompasses the target subject.

EMBODIMENT 91. The method of embodiment 90, wherein the region of interest has a diameter of 4 to 12 inches.

EMBODIMENT 92. The method of any of embodiments 88 to 91, wherein the multi-slice excitation includes exciting multiple slices along an axis of the inhomogeneous permanent gradient field, wherein each of the multiple slices has a bandwidth that is similar to the broad bandwidth of the chirped pulses.

EMBODIMENT 93. The method of any of embodiments 88 to 92, wherein the chirped pulses comprise identical bandwidths and differing durations.

EMBODIMENT 94. The method of any of embodiments 88 to 93, wherein the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

EMBODIMENT 95. The method of any of embodiments 88 to 94, wherein the chirped pulses are configured to produce a 1-dimensional signal along an axis of the inhomogeneous permanent gradient field.

EMBODIMENT 96. The method of embodiment 95, wherein the 1-dimensional signal is the first 1-dimensional signal, the gradient pulses are configured to produce a second 1-dimensional signal and a third 1-dimensional signal that are orthogonal to each other and to the axis of the inhomogeneous permanent gradient field.

EMBODIMENT 97. The method of any of embodiments 88 to 96, wherein the gradient pulses are configured for encoding spatial information to the signal.

EMBODIMENT 98. The method of any of embodiments 88 to 97, wherein the combination of the inhomogeneous permanent gradient field and the chirped pulses are configured for slice selection in the inhomogeneous permanent gradient and a frequency encoding gradient.

EMBODIMENT 99. The method of any of embodiments 88 to 98, wherein the target subject is an anatomical portion of a body.

EMBODIMENT 100. The method of any of embodiments 88 to 98, wherein the receive coil comprises an array of receive coils and each of the array of receive coils is configured for specific anatomical portion of a body.

EMBODIMENT 101. The method of any of embodiments 88 to 100, wherein the chirped pulses induce a signal in the target subject, and the signal is received by the receive coil.

EMBODIMENT 102. The method of any of embodiments 88 to 101, wherein each of the at least two chirped pulses are split into two components that are 90 degrees out of phase.

EMBODIMENT 103. The method of any of embodiments 88 to 102, wherein each of the at least two chirped pulses are split into two components that are sent to two separate ports of the transmit system.

EMBODIMENT 104. The method of any of embodiments 88 to 103, wherein the magnetic resonance imaging system further comprises a signal conditioning box and a control system, wherein the signal conditioning box is configured to turn the control system on and off with a blanking signal.

EMBODIMENT 105. The method of embodiment 104, wherein turning the control system on and off with the blanking signal respectively enables and disables a radio frequency amplifier.

EMBODIMENT 106. The method of embodiment 90, wherein the radio frequency transmit system comprises a transmit coil that is non-planar and oriented to partially surround the region of interest.

EMBODIMENT 107. The method of embodiment 106, wherein the magnetic resonance imaging system further comprises a tuning box, wherein the tuning box is configured to alter the frequency response of the transmit coil.

EMBODIMENT 108. The method of embodiment 90, wherein the gradient coil set is non-planar and oriented to partially surround the region of interest, and wherein the gradient coil set is configured to project a magnetic field gradient to the region of interest.

EMBODIMENT 109. The method of embodiment 90, wherein the receive coil is a flexible coil configured to be affixed to an anatomical portion of a patient for imaging within the region of interest.

EMBODIMENT 110. The method of embodiment 90, wherein the receive coil is in one of a single-loop coil configuration, figure-8 coil configuration, or butterfly coil configuration, wherein the receive coil is smaller than the region of interest.

EMBODIMENT 111. The method of embodiment 106, wherein the transmit coil and the gradient coil set are concentric about the region of interest.

EMBODIMENT 112. A non-transitory computer-readable medium in which a program is stored for causing a computer to perform a method for performing magnetic resonance imaging, the method comprising providing an imaging system comprising a radio frequency receive coil, and a permanent magnet for providing a permanent gradient field. The method further comprises placing the receive coil proximate a target subject; applying a sequence of chirped pulses having a wide bandwidth; applying a multi-slice excitation along the permanent gradient field, wherein the multi-slice excitation includes exciting multiple slices along an axis of the permanent gradient field, wherein each of the multiple slices has a bandwidth that is similar to the wide bandwidth of the chirped pulses; applying a phase encoding field along two orthogonal directions perpendicular to the axis of the permanent gradient field; and acquiring a magnetic resonance image of the target subject.

EMBODIMENT 113. The method of embodiment 112, wherein application of the chirped pulses, multi-slice excitation, and gradient pulses are timed so that each magnetization refocuses at a time of acquisition of a signal.

EMBODIMENT 114. The method of embodiment 113, wherein each magnetization focuses in a region of interest, wherein the region of interest encompasses the target subject.

EMBODIMENT 115. The method of embodiment 114, wherein the region of interest has a diameter of 4 to 12 inches.

EMBODIMENT 116. The method of any of embodiments 112 to 115, wherein the chirped pulses comprise identical bandwidths and differing durations.

EMBODIMENT 117. The method of embodiment 116, wherein the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

EMBODIMENT 118. The method of any of embodiments 112 to 117, wherein the chirped pulses are configured to produce a 1-dimensional signal along an axis of the permanent gradient field.

EMBODIMENT 119. The method of embodiment 118, further comprising applying a plurality of gradient pulses via a gradient coil set orthogonal to the inhomogeneous permanent gradient field, wherein the 1-dimensional signal is the first 1-dimensional signal, the gradient pulses are configured to produce a second 1-dimensional signal and a third 1-dimensional signal that are orthogonal to each other and to the axis of the permanent gradient field.

EMBODIMENT 120. The method of any of embodiments 112 to 119, further comprising applying a plurality of gradient pulses via a gradient coil set orthogonal to the inhomogeneous permanent gradient field, wherein the gradient pulses are configured for encoding spatial information to the signal.

EMBODIMENT 121. The method of any of embodiments 112 to 120, wherein the combination of the permanent gradient field and the chirped pulses are configured for slice selection in the permanent gradient and a frequency encoding gradient.

EMBODIMENT 122. The method of any of embodiments 112 to 121, wherein the target subject is an anatomical portion of a body.

EMBODIMENT 123. The method of any of embodiments 112 to 122, wherein the receive coil comprises an array of receive coils and each of the array of receive coils is configured for a specific anatomical portion of a body.

EMBODIMENT 124. The method of any of embodiments 112 to 123, wherein the chirped pulses induce a signal in the target subject, and the signal is received by the receive coil.

EMBODIMENT 125. The method of any of embodiments 112 to 124, wherein the magnetic resonance imaging system further comprises a signal conditioning box and a control system, wherein the signal conditioning box is configured to turn the control system on and off with a blanking signal.

EMBODIMENT 126. The method of embodiment 125, wherein turning the system on and off with the blanking signal respectively enables and disables a radio frequency amplifier.

EMBODIMENT 127. The method of embodiment 114, wherein the imaging system further comprises a tuning box and a radio frequency transmit coil, wherein the tuning box is configured to alter the frequency response of the transmit coil.

EMBODIMENT 128. The method of embodiment 127, wherein the transmit coil is non-planar and oriented to partially surround the region of interest.

EMBODIMENT 129. The method of embodiment 114, wherein the imaging system further comprises a single-sided gradient coil set, wherein the gradient coil set is non-planar and oriented to partially surround the region of interest, and wherein the gradient coil set is configured to project a magnetic field gradient to the region of interest.

EMBODIMENT 130. The method of embodiment 114, wherein the receive coil is a flexible coil configured to be affixed to an anatomical portion of a patient for imaging within the region of interest.

EMBODIMENT 131. The method of embodiment 114, wherein the receive coil is in one of a single-loop coil configuration, figure-8 coil configuration, or butterfly coil configuration, wherein the receive coil is smaller than the region of interest.

EMBODIMENT 132. A non-transitory computer-readable medium in which a program is stored for causing a computer to perform a method for performing magnetic resonance imaging, the method comprising providing a permanent gradient magnetic field; placing a receive coil proximate a target subject; applying a sequence of chirped pulses having a wide bandwidth; selecting a slice selection gradient having the same wide bandwidth; applying a multi-slice excitation technique along an axis of the permanent gradient magnetic field; applying a plurality of gradient pulses orthogonal to the permanent gradient magnetic field; acquiring a signal of the target subject via the receive coil; and forming a magnetic resonance image of the target subject.

EMBODIMENT 133. The method of embodiment 132, wherein application of the chirped pulses, multi-slice excitation technique, and gradient pulses are timed so that each magnetization refocuses at a time of acquisition of the signal.

EMBODIMENT 134. The method of embodiment 133, wherein each magnetization focuses in a region of interest, wherein the region of interest encompasses the target subject.

EMBODIMENT 135. The method of embodiment 134, wherein the region of interest has a diameter of 4 to 12 inches.

EMBODIMENT 136. The method of any of embodiments 132 to 135, wherein the chirped pulses comprise identical bandwidths and differing durations.

EMBODIMENT 137. The method of embodiment 136, wherein the chirped pulses have a bandwidth ranging from 1 kHz to 10 kHz, 10 kHz to 40 kHz, 40 kHz to 100 kHz, 100 kHz to 400 kHz, 400 kHz to 1 MHz, or any ranges of bandwidth thereof.

EMBODIMENT 138. The method of any of embodiments 132 to 137, wherein the chirped pulses are configured to produce a 1-dimensional signal along an axis of the permanent gradient field.

EMBODIMENT 139. The method of embodiment 138, wherein the 1-dimensional signal is the first 1-dimensional signal, the gradient pulses are configured to produce a second 1-dimensional signal and a third 1-dimensional signal that are orthogonal to each other and to the axis of the permanent gradient field.

EMBODIMENT 140. The method of any of embodiments 132 to 139, wherein the gradient pulses are configured for encoding spatial information to the signal.

EMBODIMENT 141. The method of any of embodiments 132 to 140, wherein the combination of the permanent gradient field and the chirped pulses are configured for slice selection in the permanent gradient and a frequency encoding gradient.

EMBODIMENT 142. The method of any of embodiments 132 to 141, wherein the target subject is an anatomical portion of a body.

EMBODIMENT 143. The method of any of embodiments 132 to 142, wherein the receive coil comprises an array of receive coils and each of the array of receive coils is configured for specific anatomical portion of a body.

EMBODIMENT 144. The method of any of embodiments 132 to 143, wherein the chirped pulses induce a signal in the target subject, and the signal is received by the receive coil.

EMBODIMENT 145. The method of any of embodiments 132 to 144, wherein the magnetic resonance imaging system further comprises a signal conditioning box and a control system, wherein the signal conditioning box is configured to turn the control system on and off with a blanking signal.

EMBODIMENT 146. The method of embodiment 145, wherein turning the system on and off with the blanking signal respectively enables and disables a radio frequency amplifier.

EMBODIMENT 147. The method of embodiment 134, wherein the imaging system further comprises a tuning box and a radio frequency transmit coil, wherein the tuning box is configured to alter frequency response of the transmit coil.

EMBODIMENT 148. The method of embodiment 147, wherein the transmit coil is non-planar and oriented to partially surround the region of interest.

EMBODIMENT 149. The method of embodiment 134, wherein the imaging system further comprises a single-sided gradient coil set, wherein the gradient coil set is non-planar and oriented to partially surround the region of interest, and wherein the gradient coil set is configured to project a magnetic field gradient to the region of interest.

EMBODIMENT 150. The method of embodiment 134, wherein the receive coil is a flexible coil configured to be affixed to an anatomical portion of a patient for imaging within the region of interest.

EMBODIMENT 151. The method of embodiment 134, wherein the receive coil is in one of a single-loop coil configuration, figure-8 coil configuration, or butterfly coil configuration, wherein the receive coil is smaller than the region of interest.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

What is claimed:

1. A magnetic resonance imaging system configured to provide a permanent gradient magnetic field defining an axis, the magnetic resonance imaging system comprising:
   a receive coil positionable adjacent to a target subject;
   a control circuit configured to:
      apply a sequence of chirped pulses having a wide bandwidth;
      select a slice selection gradient having the same wide bandwidth;
      apply a multi-slice excitation technique along the axis;
      apply a plurality of gradient pulses orthogonal to the axis;
      acquire a signal of the target subject, wherein application of the sequence of chirped pulses, multi-slice excitation technique, and gradient pulses are timed to refocus a magnetization of the permanent gradient magnetic field at a time of acquisition of the signal within a region of interest encompassing the target subject; and
      form a magnetic resonance image of the target subject; and
   a single-sided gradient coil set that is non-planar and oriented to partially surround the region of interest, wherein the single-sided gradient coil set is configured to project the plurality of gradient pulses into the region of interest.

2. The magnetic resonance imaging system of claim 1, wherein the receive coil comprises a flexible coil configured to be affixed to an anatomical portion of a patient for imaging within the region of interest.

3. The magnetic resonance imaging system of claim 1, further comprising a tuning box and a radio frequency transmit coil, wherein the tuning box is configured to alter the frequency response of the radio frequency transmit coil.

4. The magnetic resonance imaging system of claim 3, wherein the radio frequency transmit coil is non-planar and oriented to partially surround the region of interest.

5. The magnetic resonance imaging system of claim 1, wherein the sequence of chirped pulses comprises identical bandwidths and differing durations.

6. The magnetic resonance imaging system of claim 1, wherein the sequence of chirped pulses configured to produce a one-dimensional signal along the axis of the permanent gradient magnetic field.

7. The magnetic resonance imaging system of claim 6, wherein the one-dimensional signal comprises a first one-dimensional signal, and wherein the gradient pulses are further configured to produce a second one-dimensional signal and a third one-dimensional signal that are orthogonal to each other and to the axis of the permanent gradient magnetic field.

8. The magnetic resonance imaging system of claim 1, wherein the gradient pulses are configured for encoding spatial information to the signal.

9. The magnetic resonance imaging system of claim 1, wherein the combination of the permanent gradient field and the sequence of chirped pulses is configured for slice selection in the inhomogeneous permanent gradient and a frequency encoding gradient.

10. The magnetic resonance imaging system of claim 1, wherein the sequence of chirped pulses is configured to induce a signal in the target subject, and wherein the receive coil is configured to receive the signal.

11. The magnetic resonance imaging system of claim 1, further comprising:
a signal conditioning box; and
a radio frequency transmit system, wherein the radio frequency transmit system comprises a radio frequency amplifier and a transmit coil, and wherein the signal conditioning box is configured to enable and disable the radio frequency amplifier.

12. A magnetic resonance imaging system, comprising:
a radio frequency receive system comprising a radio frequency receive coil positionable adjacent to a target subject;
a permanent magnet configured to provide an inhomogeneous permanent gradient field;
a radio frequency transmit system;
a single-sided gradient coil set; and
a control circuit communicably coupled to the radio frequency receive system, the radio frequency transmit system, and the single-sided gradient coil set, wherein the control circuit is configured to:
apply, by the radio frequency transmit system, a sequence of chirped pulses;
apply a multi-slice excitation pulse along the inhomogeneous permanent gradient field;
apply, by the single-sided gradient coil set, a plurality of gradient pulses orthogonal to the inhomogeneous permanent gradient field;
acquire, by the radio frequency receive system, a signal of the target subject; and
form a magnetic resonance image of the target subject.

13. The magnetic resonance imaging system of claim 12, further comprising a power source, wherein the power source is configured to flow current through at least one of the radio frequency transmit system and the single-sided gradient coil set to generate an electromagnetic field in a region of interest, and wherein the region of interest is configured to receive the target subject.

14. The magnetic resonance imaging system of claim 12, wherein the multi-slice excitation pulse comprises exciting multiple slices along an axis of the inhomogeneous permanent gradient field.

15. A magnetic resonance imaging system, comprising:
a radio frequency receive coil configured to be placed adjacent to a target subject positioned in a region of interest;
a permanent magnet configured to provide an inhomogeneous permanent gradient field in the region of interest;
a single-sided gradient coil set that is non-planar and oriented to partially surround the region of interest, wherein the single-sided gradient coil set is configured to project a magnetic field gradient into the region of interest;
a radio frequency transmit system; and
a control circuit communicably coupled to the radio frequency receive system and the radio frequency transmit system, wherein the control circuit is configured to:
apply a sequence of chirped pulses having a wide bandwidth;
apply a multi-slice excitation along the inhomogeneous permanent gradient field, wherein the multi-slice excitation comprises exciting multiple slices along an axis of the permanent gradient field in the region of interest, and wherein each of the multiple slices comprises the wide bandwidth;
apply a phase encoding field along axes perpendicular to the axis of the inhomogeneous permanent gradient field; and
acquire a magnetic resonance image of the target subject.

16. The magnetic resonance imaging system of claim 15, wherein application of the sequence of chirped pulses, multi-slice excitation, and gradient pulses are timed to refocus a magnetization of the inhomogeneous permanent gradient magnetic field at a time of acquisition of a signal.

17. The magnetic resonance imaging system of claim 15, wherein the radio frequency receive coil is configured to abut an anatomical portion of a patient.

* * * * *